US011865195B2

(12) United States Patent
Sinusas et al.

(10) Patent No.: US 11,865,195 B2
(45) Date of Patent: Jan. 9, 2024

(54) EVALUATION OF PRESENCE OF AND VULNERABILITY TO ATRIAL FIBRILLATION AND OTHER INDICATIONS USING MATRIX METALLOPROTEINASE-BASED IMAGING

(71) Applicants: Lantheus Medical Imaging, Inc., North Billerica, MA (US); Yale University, New Haven, CT (US)

(72) Inventors: Albert J. Sinusas, Guilford, CT (US); Joseph G. Akar, New Haven, CT (US); Richard R. Cesati, Pepperell, MA (US); Heike S. Radeke, South Grafton, MA (US); Stephen B. Haber, Westford, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 49 days.

(21) Appl. No.: 16/881,182

(22) Filed: May 22, 2020

(65) Prior Publication Data

US 2020/0390912 A1 Dec. 17, 2020

Related U.S. Application Data

(63) Continuation of application No. 15/722,958, filed on Oct. 2, 2017, now abandoned, which is a continuation of application No. 14/357,555, filed as application No. PCT/US2012/062863 on Oct. 31, 2012, now abandoned.

(60) Provisional application No. 61/658,531, filed on Jun. 12, 2012, provisional application No. 61/559,587, filed on Nov. 14, 2011, provisional application No. 61/558,677, filed on Nov. 11, 2011.

(51) Int. Cl.
*A61K 51/04* (2006.01)
*A61K 51/08* (2006.01)

(52) U.S. Cl.
CPC ........ *A61K 51/044* (2013.01); *A61K 51/0459* (2013.01); *A61K 51/0476* (2013.01); *A61K 51/0478* (2013.01); *A61K 51/0497* (2013.01); *A61K 51/08* (2013.01); *A61B 2576/023* (2013.01)

(58) Field of Classification Search
CPC ............ A61K 2123/00; A61K 2121/00; A61K 51/00; A61K 51/04; A61K 51/044; A61K 51/08; A61K 51/0459; A61K 51/0476; A61K 51/0478; A61K 51/0497; A61B 2576/023; G16H 30/40
USPC .... 424/1.11, 1.65, 1.69, 9.1, 9.2; 514/1, 1.1, 514/19.2, 19.3, 19.4, 19.5, 19.6; 534/7, 534/10–16
See application file for complete search history.

(56) References Cited

U.S. PATENT DOCUMENTS

| | | |
|---|---|---|
| 5,230,883 A | 7/1993 | Kornguth et al. |
| 6,511,648 B2 | 1/2003 | Harris et al. |
| 6,656,448 B1 | 12/2003 | Carpenter et al. |
| 6,989,139 B2 | 1/2006 | Decicco et al. |
| 7,842,279 B2 | 11/2010 | McBride et al. |
| 8,506,499 B2 * | 8/2013 | Mukherjee ......... G01N 33/6893 600/508 |
| 2005/0287074 A1 | 12/2005 | Carpenter et al. |
| 2008/0279769 A1 | 11/2008 | Solbakken et al. |
| 2011/0009861 A1 | 1/2011 | Mukherjee et al. |
| 2012/0237445 A1 | 9/2012 | Castner et al. |
| 2013/0338194 A1 | 12/2013 | Mukherjee et al. |
| 2015/0023873 A1 | 1/2015 | Sinusas et al. |
| 2018/0177901 A1 | 6/2018 | Sinusas et al. |

FOREIGN PATENT DOCUMENTS

| | | |
|---|---|---|
| RU | 2 303 266 C1 | 7/2007 |
| WO | WO 01/060416 A2 | 8/2001 |
| WO | WO 02/067761 A2 | 9/2002 |
| WO | WO 2004/069365 A1 | 8/2004 |
| WO | WO 2005/023314 A1 | 3/2005 |
| WO | WO 2006/032911 A2 | 3/2006 |
| WO | WO 2007/005491 A1 | 1/2007 |
| WO | WO 2008/085895 A2 | 7/2008 |
| WO | WO 2011/005322 A2 | 1/2011 |
| WO | WO 2011/097649 A2 | 8/2011 |
| WO | WO 2011/143360 A2 | 11/2011 |

OTHER PUBLICATIONS

Su et al, Circulation, vol. 112, pp. 3157-3167 (Year: 2005).*
Nakano et al, Journal of the American College of Cardiology, vol. 43, No. 5, pp. 818-825 (Year: 2004).*
Extended European Search Report for EP12847031.7 dated Jun. 17, 2015.
International Search Report and Written Opinion for PCT/US2012/062863 dated Feb. 14, 2013.
International Preliminary Report on Patentability for PCT/US2012/062863 dated May 22, 2014.
[No Author Listed], Triphenylphosphine-3,3',3"-trisulfonic acid trisodium salt. Chemical Book Data Sheet. 2016. Last accessed Feb. 23, 2017 from <http://www.chemicalbook.com/ChemicalProductProperty_EN_CB5171996.htm>. 2 pages.

(Continued)

*Primary Examiner* — D. L. Jones
(74) *Attorney, Agent, or Firm* — Wolf, Greenfield & Sacks, P.C.

(57) ABSTRACT

The invention provides, in some embodiments, methods relating to assessing increased risk of developing atrial fibrillation (AF), and/or the likelihood of responding to particular AF therapies using imaging agents comprising an MMP inhibitor linked to an imaging moiety. The invention further provides methods for evaluating the presence of the risk of developing other cardiovascular conditions and assessing the effectiveness of treatment or other intervention for such conditions by determining MMP levels.

16 Claims, 11 Drawing Sheets

(56) References Cited

OTHER PUBLICATIONS

Akar et al., Regional Heterogeneity in Matrix Proteases and Inhibitors Occurs Within the Atrium Following Myocardial Infarction; Relation to Fibrillation Vulnerability. Circulation, Meeting Abstract. 2013;128:A15848.
Ashikaga et al., Effects of amiodarone on electrical and structural remodeling induced in a canine rapid pacing-induced persistent atrial fibrillation model. Eur J Pharmacol. Apr. 24, 2006;536(1-2):148-53. Epub Mar. 6, 2006.
Bhatia et al., Atrial Fibrillation Post-Myocardial Infarction: Frequency, Consequences, and Management. Current Heart Failure Reports. 2004;1:149-55.
Chan et al., End-expiration respiratory gating for a high-resolution stationary cardiac SPECT system. Phys Med Biol. Oct. 21, 2014;59(20):6267-87. doi: 10.1088/0031-9155/59/20/6267.
Chan et al., Noise suppressed partial volume correction for cardiac SPECT/CT. Med Phys. Sep. 2016;43(9):5225-39. doi: 10.1118/1.4961391.
Chen et al., Upregulation of matrix metalloproteinase-9 and tissue inhibitors of metalloproteinases in rapid atrial pacing-induced atrial fibrillation. J Mol Cell Cardiol. Dec. 2008;45(6):742-53. doi: 10.1016/j.yjmcc.2008.07.007. Epub Jul. 23, 2008.
Dobrucki et al., Angiotensin-receptor blockade reduces matrix metalloproteinase activation as assessed with targeted micro SPECT-CT imaging in rodent model of myocardial infarction. ICNC9—Nuclear Cardiology & Cardiac CT. May 11, 2009. Barcelona, Spain; Oral Abstract Session: S22.
Golestani et al., Imaging vessel wall biology to predict outcome in abdominal aortic aneurysm. Circ Cardiovasc Imaging. Dec. 30, 2014;8(1). pii:e002471. doi:10.1161/CIRCIMAGING.114.002471.
Harrison, Atrial Fibrillation in Acute Myocardial Infarction. Chest. Jul. 1976;70(1):3-4.
Helmers et al., Atrial Fibrillation in Acute Myocardial Infarction. Acta Med. Scand. 1973;193:39-44.
Hoffman et al., Quantitation in positron emission computed tomography: 1. Effect of object size. J Comput Assist Tomogr. Jun. 1979;3(3):299-308.
Hunt et al., Effects of atrial fibrillation on prognosis of acute myocardial infarction. British Heart Journal. 1978;40:303-7.
Jaffer et al., Molecular imaging of myocardial infarction. J Mol Cell Cardiol. Dec. 2006;41(6):921-33. Epub Oct. 24, 2006.
Jung et al., Multimodality and molecular imaging of matrix metalloproteinase activation in calcific aortic valve disease. J Nucl Med. Jun. 2015;56(6):933-8. doi: 10.2967/jnumed.114.152355. Epub Apr. 23, 2015.
Kallergis et al., Extracellular matrix alterations in patients with paroxysmal and persistent atrial fibrillation: biochemical assessment of collagen type-I turnover. J Am Coll Cardiol. Jul. 15, 2008;52(3):211-5. doi:10.1016/j.jacc.2008.03.045.
Kato et al., Impact of matrix metalloproteinase-2 levels on long-term outcome following pharmacological or electrical cardioversion in patients with atrial fibrillation. Europace. Mar. 2009;11(3):332-7. doi: 10.1093/europace/eun389. Epub Jan. 15, 2009.
Klass et al., Atrial fibrillation associated with acute myocardial infarction: A study of 34 cases. American Heart Journal. Jun. 1970;79(6):752-60.
Kojima et al., Effect of spatial resolution on SPECT quantification values. J Nucl Med. Apr. 1989;30(4):508-14.
Kuppahally et al., Left atrial strain and strain rate in patients with paroxysmal and persistent atrial fibrillation: relationship to left atrial structural remodeling detected by delayed-enhancement MRI. Circ Cardiovasc Imaging. May 2010;3(3):231-9. doi:10.1161/CIRCIMAGING.109.865683. Epub Feb. 4, 2010.
Lin et al., Acute Embolic Myocardial Infarction in a Patient with Paroxysmal Atrial Fibrillation Receiving Direct-current Cardioversion. J. Chin. Med. Assoc. Mar. 2009;72(3):146-9.
Lin et al., Dual isotope hybrid SPECT/CT imaging permits serial quantitative assessment of matrix metalloproteinase activity following myocardial infarction. J Nucl Med. Apr. 1, 2012;53(4):669. Abstract 15.
Lin et al., Evaluation of Atrial Remodeling and Fibrillation Vulnerability Using Molecular Imaging of Matrix Metalloproteinases. Circulation, Meeting Abstract. 2011;124:A8449.
Lin et al., Increased expression of extracellular matrix proteins in rapid atrial pacing-induced atrial fibrillation. Heart Rhythm. Jul. 2007;4(7):938-49. Epub Apr. 6, 2007.
Liu et al., Accuracy and reproducibility of absolute quantification of myocardial focal tracer uptake from molecularly targeted SPECT/CT: a canine validation. J Nucl Med. Mar. 2011;52(3):453-60. doi: 10.2967/jnumed.110.082214. Epub Feb. 14, 2011.
Liu et al., Anatomical-based partial volume correction for low-dose dedicated cardiac SPECT/CT. Phys Med Biol. Sep. 7, 2015;60(17):6751-73. doi: 10.1088/0031-9155/60/17/6751.
Mahnkopf et al., Evaluation of the left atrial substrate in patients with lone atrial fibrillation using delayed-enhanced MRI: implications for disease progression and response to catheter ablation. Heart Rhythm. Oct. 2010;7(10):1475-81. doi: 10.1016/j.hrthm.2010.06.030. Epub Jul. 1, 2010.
Matusiak et al., Probes for non-invasive matrix metalloproteinase-targeted imaging with PET and SPECT. Curr Pharm Des. 2013;19(25):4647-72.
Mcbride et al., A novel method of 18F radiolabeling for Pet. J Nucl Med. Jun. 2009;50(6):991-8. doi: 10.2967/jnumed.108.060418. Epub May 14, 2009.
Mekkaoui et al., Regional matrix metalloproteinase activation correlates with microstructure diffusion tensor indices post myocardial infarction. 13th Annual SCMR Scientific Sessions. Jan. 21-24, 2010, Phoenix Arizona. Poster Presentation.
Moe et al., Matrix metalloproteinase inhibition attenuates atrial remodeling and vulnerability to atrial fibrillation in a canine model of heart failure. J Card Fail. Nov. 2008;14(9):768-76. doi: 10.1016/j.cardfail.2008.07.229. Epub Aug. 22, 2008.
Mukherjee et al., Selective induction of matrix metalloproteinases and tissue inhibitor of metalloproteinases in atrial and ventricular myocardium in patients with atrial fibrillation. Am J Cardiol. Feb. 15, 2006;97(4):532-7. Epub Jan. 4, 2006.
Nakano et al., Matrix metalloproteinase-9 contributes to human atrial remodeling during atrial fibrillation. J Am Coll Cardiol. Mar. 3, 2004;43(5):818-25.
Pedersen et al., The occurrence and prognostic significance of atrial fibrillation/-flutter following acute myocardial infarction. European Heart Journal. 1999;20:748-54.
Pizzetti et al., Incidence and prognostic significance of atrial fibrillation in acute myocardial infarction: the GISSI-3 data. Heart. 2001;86:527-32.
Rahmim et al., PET versus SPECT: strengths, limitations and challenges. Nucl Med Commun. Mar. 2008;29(3):193-207. doi: 10.1097/MNM.0b013e3282f3a515.
Razavian et al., Atherosclerosis plaque heterogeneity and response to therapy detected by in vivo molecular imaging of matrix metalloproteinase activation. J Nucl Med. Nov. 2011;52(11):1795-802. doi: 10.2967/jnumed.111.092379. Epub Oct. 3, 2011.
Razavian et al., Hypertension and MMP imaging in atherosclerosis. J Nucl Med. May 1, 2015,56: Abstract 1477.
Razavian et al., Lipid lowering and imaging protease activation in atherosclerosis. J Nucl Cardiol. Apr. 2014;21(2):319-28. doi: 10.1007/s12350-013-9843-7. Epub Dec. 25, 2013.
Razavian et al., Molecular imaging of matrix metalloproteinase activation to predict murine aneurysm expansion in vivo. J Nucl Med. Jul. 2010;51(7):1107-15. doi: 10.2967/jnumed.110.075259. Epub Jun. 16, 2010.
Sahul et al., Targeted imaging of the spatial and temporal variation of matrix metalloproteinase activity in a porcine model of postinfarct remodeling: relationship to myocardial dysfunction. Circ Cardiovasc Imaging. Jul. 2011;4(4):381-91. doi:10.1161/CIRCIMAGING.110.961854. Epub Apr. 19, 2011.
Schmitt et al., Atrial fibrillation in acute myocardial infarction: a systematic review of the incidence, clinical features and prognostic implications. European Heart Journal. 2009;30:1038-45.
Sheppard, Practical Cardiovascular Pathology. Chapter 1—Autopsy Cardiac Examination. Second Edition. CRC Press. London. Aug. 26, 2011:1-23.

(56) References Cited

OTHER PUBLICATIONS

Sinusas, Beyond Infarction: Molecular Imaging Markers of Ventricular Remodeling. Society of Nuclear Medicine 2009 Annual Meeting—Toronto.

Sinusas, Multi-Modality and Molecular Imaging of Cardiac Remodeling. Yale Translation Research Imaging Center. Feb. 2015 Presentation.

Spinale et al., Cardiac restricted overexpression of membrane type-1 matrix metalloproteinase causes adverse myocardial remodeling following myocardial infarction. J Biol Chem. Sep. 24, 2010;285(39):30316-27. doi: 10.1074/jbc.M110.158196. Epub Jul. 19, 2010.

Spinale, Myocardial matrix remodeling and the matrix metalloproteinases: influence on cardiac form and function. Physiol Rev. Oct. 2007;87(4):1285-342.

Stacy et al., Targeted imaging of matrix metalloproteinase activity in the evaluation of remodeling tissue-engineered vascular grafts implanted in a growing lamb model. J Thorac Cardiovasc Surg. Nov. 2014;148(5):2227-33. doi:10.1016/j.jtcvs.2014.05.037. Epub May 21, 2014.

Su et al., Noninvasive targeted imaging of matrix metalloproteinase activation in a murine model of postinfarction remodeling. Circulation. Nov. 15, 2005;112(20):3157-67. Epub Nov. 7, 2005.

Tavakoli et al., Matrix metalloproteinase activation predicts amelioration of remodeling after dietary modification in injured arteries. Arterioscler Thromb Vasc Biol. Jan. 2011;31(1):102-9. doi:10.1161/ATVBAHA.110.216036. Epub Oct. 14, 2010.

Tekabe et al., Noninvasive monitoring the biology of atherosclerotic plaque development with radiolabeled annexin V and matrix metalloproteinase inhibitor in spontaneous atherosclerotic mice. J Nucl Cardiol. Dec. 2010;17(6):1073-81. doi:10.1007/s12350-010-9276-5. Epub Aug. 11, 2010.

Thorn et al., In vivo non-invasive evaluation of therapeutic hydrogels for modulation of post infarction remodeling: role of MMP-targeted SPECT myocardial imaging in a chronic porcine model. 12th International Conference on Nuclear Cardiology and Cardiac CT. May 3, 2015;16(1): Abstract 219.

Vatutin et al., Ectopic myocardial activity as a risk factor for recurrence atrial fibrillation. Ukrainskiy Kardiologicheskiy Zhurnal. Feb. 2010, No. 1, 3 pages.

Visse et al., Matrix metalloproteinases and tissue inhibitors of metalloproteinases: structure, function, and biochemistry. Circ Res. May 2, 2003;92(8):827-39.

Wisenberg et al., In vivo quantitation of regional myocardial blood flow by positron-emission computed tomography. Circulation. Jun. 1981;63(6):1248-58.

Won et al., Noninvasive imaging of myocardial extracellular matrix for assessment of fibrosis. Curr Opin Cardiol. May 2013;28(3):282-9. doi: 10.1097/HCO.0b013e32835f5a2b.

Xu et al., Atrial extracellular matrix remodeling and the maintenance of atrial fibrillation. Circulation. Jan. 27, 2004;109(3):363-8. Epub Jan. 19, 2004.

Xue et al., Design, synthesis, and structure-activity relationships of macrocyclic hydroxamic acids that inhibit tumor necrosis factor alpha release in vitro and in vivo. J Med Chem. Aug. 2, 2001;44(16):2636-60.

Yancy et al., 2013 ACCF/AHA guideline for the management of heart failure: a report of the American College of Cardiology Foundation/American Heart Association Task Force on practice guidelines. Circulation. Oct. 15, 2013;128(16):e240-327. doi: 10.1161/CIR.0b013e31829e8776. Epub Jun. 5, 2013.

Zhang et al., Matrix metalloproteinase-9/tissue inhibitors of metalloproteinase-1 expression and atrial structural remodeling in a dog model of atrial fibrillation: inhibition with angiotensin converting enzyme. Cardiovasc Pathol. Nov.-Dec. 2008;17(6):399-409. doi:10.1016/j.carpath.2008.02.008. Epub Aug. 15, 2008.

Zhang et al., Molecular imaging of activated matrix metalloproteinases in vascular remodeling. Circulation. Nov. 4, 2008;118(19):1953-60. doi: 10.1161/CIRCULATIONAHA.108.789743. Epub Oct. 20, 2008.

\* cited by examiner

EVALUATION OF PRESENCE OF AND VULNERABILITY TO ATRIAL FIBRILLATION AND OTHER INDICATIONS USING MATRIX METALLOPROTEINASE-BASED IMAGING

RELATED APPLICATIONS

The present application is a continuation of U.S. Ser. No. 15/722,958, filed on Oct. 2, 2017, which is a continuation of U.S. Ser. No. 14/357,555, filed on May 9, 2014, which is a national stage filing under 35 U.S.C. § 371 of International Application No. PCT/US2012/062863, filed on Oct. 31, 2012, which claims priority under 35 U.S.C. § 119(e) to U.S. provisional application Ser. No. 61/658,531 filed on Jun. 12, 2012, U.S. Ser. No. 61/559,587, filed on Nov. 14, 2011, and U.S. Ser. No. 61/558,677, filed on Nov. 11, 2011, each of which are incorporated herein by reference.

BACKGROUND OF INVENTION

Atrial fibrillation (AF) is a disturbance in the rhythmic beating (or arrhythmia) of the upper chambers of the heart. AF is the most common sustained cardiac arrhythmia, responsible for almost 50% of hospitalizations for arrhythmias (Benjamin E J, et al. 1998; Wyse D G, et al. 2002; Benjamin E J, et al. 1997; Allessie M A, et al. 2001). Consequently, AF is a significant cause of morbidity and mortality and treatment of AF has been hampered by the ineffectiveness of available drugs. Moreover, attempts to terminate AF with electrical shocks, using a process termed "cardioversion" works for only about one-half of the patients during the first 6-12 months. Therefore, a "simple" means to identify patients in whom cardioversion would effectively terminate AF would be beneficial in terms of saved time and money. Moreover, a means to identify patients that may or may not benefit from an implantable pacer, pharmacological rate and/or rhythm control therapy and/or ablation would also be beneficial.

SUMMARY OF INVENTION

The invention is broadly based on the use of matrix metalloproteinase (MMP) based imaging to detect the presence of (including early detection of) and/or the risk of developing certain cardiovascular conditions and to evaluate the efficacy of therapies and/or other interventions directed towards such conditions. MMP levels (and thus activity) can be detected using in vivo medial imaging techniques. In accordance with the invention, MMP activation is an indicator of tissue (e.g., vascular) remodeling, and such remodeling is an indicator of certain conditions or an indicator of developing certain conditions.

Thus, the invention is premised, in part, on the surprising finding that MMP levels (and activity) can be detected at early time periods, including prior to the onset of certain cardiovascular conditions such as but not limited to myocardial fibrosis, AF, calcific aortic valve disease (CAVD), and atherosclerosis. It has not been heretofore known that MMP levels could be detected at such early time points and that detection at these early time points correlated with increased risk of, for example, AF and CAVD. The invention therefore provides, inter alia, methods for determining increased risk (or likelihood, as the terms are used interchangeably herein) of developing, for example, AF or CAVD based on detection and/or quantification of MMP levels, and more specifically localized MMP levels such as cardiac MMP levels.

In one aspect, the invention provides a method for evaluating the risk of developing AF comprising administering to a subject an imaging agent comprising a matrix metalloproteinase (MMP) inhibitor linked to an imaging moiety and obtaining a cardiac image.

In some embodiments, the subject has experienced a cardiovascular insult such as, but not limited to, a myocardial infarction and/or heart surgery and/or has been diagnosed as having a cardiovascular disease such as but not limited to coronary artery disease, heart valve disease, cardiomyopathy, and/or congenital heart disease. If the subject has experienced a cardiovascular insult, the method may be performed within days, or within a week, or within 2 weeks, or within a month, or within 2 months of the cardiovascular insult. In some embodiments, the method may be performed within 10 days of the cardiovascular insult. In some embodiments, the subject does not have a history of AF (i.e., the subject has not been heretofore diagnosed as having AF), although the subject may have been diagnosed with other cardiovascular diseases as stated above. In some embodiments, the subject may have a familial history of AF and/or the subject may present with certain risk factors that are associated with an increased risk of developing AF. Such risk factors include high blood pressure and chronic lung disease.

In these and other aspects of the invention, the method may be performed once on the subject or it may be performed repeatedly on the subject in order to monitor the subject over a period of time.

In another aspect, the invention provides a method for evaluating the risk of AF recurrence (e.g., following cardioversion therapy). The method comprises administering to a subject previously diagnosed with AF and treated with an AF therapy an imaging agent of the invention, and obtaining an image of the heart of the subject, in whole or in part. In some embodiments, the above-normal levels (including in some instances mere presence) of MMP following cardioversion therapy indicate an increased risk of AF recurrence (e.g., following cardioversion). In some embodiments, the AF therapy may be cardioversion, pharmacological rate and/or rhythm control, an implantable pacer, and the like.

In another aspect, the invention provides a method for identifying in a subject having a history of AF the likelihood of responding to treatment with an implantable pacer. The method comprises administering to a subject previously diagnosed with AF an imaging agent of the invention, and obtaining an image of the heart of the subject, in whole or in part. The above-normal levels (including in some instances mere presence) of MMP identify the subject as one to be treated with an implantable pacer.

In another aspect, the invention provides a method for identifying in a subject having a history of AF the likelihood of responding to pharmacological rate control therapy. The method comprises administering to a subject previously diagnosed with AF an imaging agent of the invention, and obtaining an image of the heart of the subject, in whole or in part. The above-normal levels (including in some instances mere presence) of MMP identify the subject as one to be treated using pharmacological rate control therapy. Such therapies include beta-blockers, calcium antagonists, and digoxin.

In another aspect, the invention provides a method for identifying in a subject having a history of AF the likelihood of responding to pharmacological rhythm control therapy.

The method comprises administering to a subject previously diagnosed with AF an imaging agent of the invention, and obtaining an image of the heart of the subject, in whole or in part. The above-normal levels (including in some instances mere presence) of MMP identify the subject as one to be treated using pharmacological rhythm control therapy. Such therapies include beta-blockers, amiodarone, class Ic agents, and sotalol.

In another aspect, the invention provides a method for identifying in a subject having a history of AF the likelihood of responding to ablation therapy. The method comprises administering to a subject previously diagnosed with AF an imaging agent of the invention, and obtaining an image of the heart of the subject, in whole or in part. The above-normal levels (including in some instances the mere presence) of MMP identify the subject as one to be treated using ablation therapy.

In some embodiments, the subject having a history of AF is a subject that has experienced an AF event. In some embodiments, the subject having a history of AF is a subject that has experienced recurrent AF.

The image indicates the presence or absence of imaging agent in the heart of the subject which in turn indicates the level (or amount of MMP) in the heart of the subject. In some embodiments, the image indicates the amount of the imaging agent in the heart of the subject, in whole or in part. In some embodiments, the image comprises atrial myocardium, including the left atrial myocardium, of the subject.

In some embodiments, the MMP inhibitor has an inhibitory constant $K_i$ of <1000 nM. In some embodiments, the MMP inhibitor has an inhibitory constant $K_i$ of <100 nM. In some embodiments, the MMP inhibitor is an inhibitor of one or more matrix metalloproteinases selected from the group consisting of MMP-2, MMP-9 and MMP-14.

In some embodiments, the imaging agent is

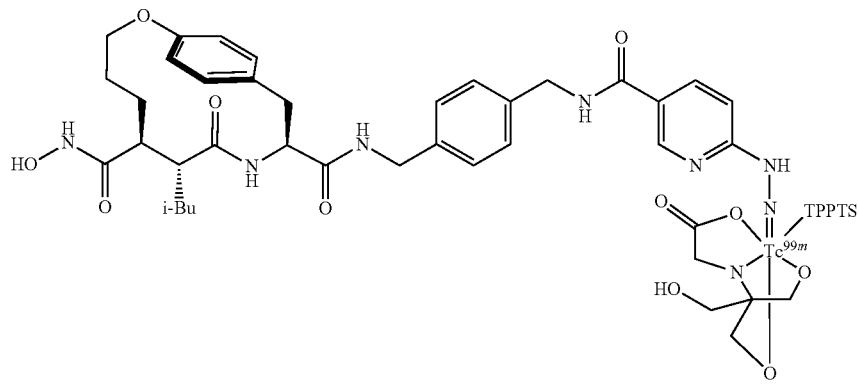

(referred to herein as $^{99m}$Tc-RP805).

In some embodiments, the imaging agent is

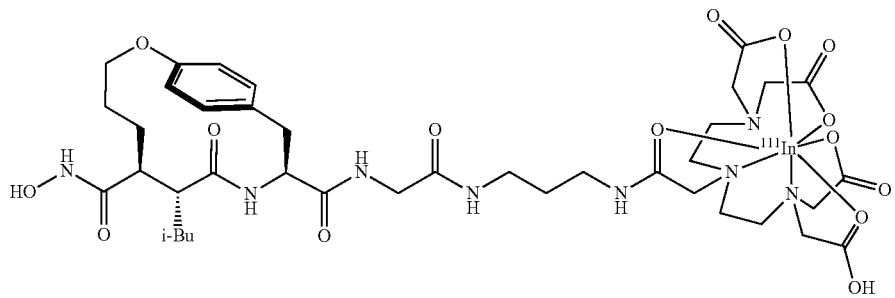

(referred to herein as $^{111}$In-RP782).

In some embodiments, the imaging agent of the invention is selected from the group consisting of:

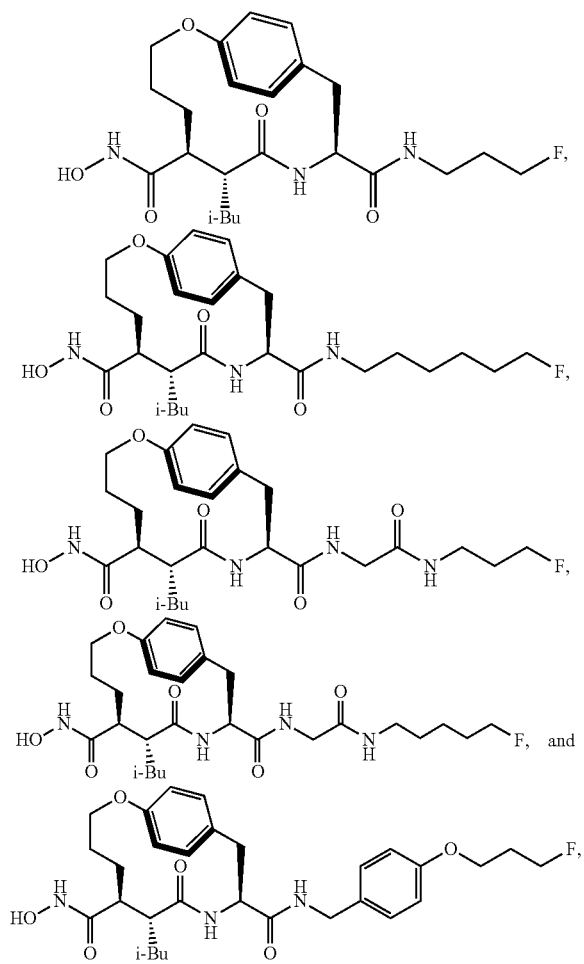

wherein F represents an isotopically-enriched population of $^{18}$F, and variants thereof comprising, instead of F, an isotopically-enriched imaging moiety selected from the group consisting of $^{11}$C, $^{13}$N, $^{123}$I, $^{125}$I, $^{99m}$Tc, $^{95}$Tc, $^{111}$In, $^{62}$Cu, $^{64}$Cu, $^{67}$Ga, and $^{68}$Ga. That is, in some embodiments, F is replaced with an isotopically-enriched imaging moiety or a chelator associated with an isotopically-enriched imaging moiety, wherein the imaging moiety is selected from the group consisting of $^{11}$C, $^{13}$N, $^{123}$I, $^{125}$I, $^{99m}$Tc, $^{95}$Tc, $^{111}$In, $^{62}$Cu, $^{64}$Cu, $^{67}$Ga, and $^{68}$Ga.

Other suitable imaging agents for MMP detection and quantitation are described herein.

In some embodiments, the method further comprises determining myocardial perfusion in the subject. Myocardial perfusion may be determined by obtaining an image of the heart, in whole or in part, using a myocardial perfusion imaging agent. Suitable myocardial perfusion imaging agents include flurpiridaz F 18 injection (4-chloro-2-(1,1-dimethylethyl)-5-({4-[(2-[$^{18}$F]fluoroethoxy)methyl]phenyl}methoxy)pyridazin-3(2H)-one), $^{99m}$Tc sestamibi (Tc99m[MIBI]$_6$, where MIBI is 2-methoxy isobutyl isonitrile), $^{201}$Thallium, and the like. In some embodiments, myocardial perfusion is quantitated. In some embodiments, an index is determined that comprises a measure of myocardial perfusion and a measure of MMP level based on the obtained images. In some embodiments, the index derives from a logisitic regression analysis of the summed rest score and the MMP level. In some embodiments, the measure of myocardial perfusion is the summed stress score. In some embodiments, the measure of perfusion is the summed rest score. In some embodiments, the measure of perfusion is the summed difference score.

In some embodiments, the MMP image and/or the myocardial perfusion image is obtained before the subject exhibits any signs of myocardial fibrosis. The presence of myocardial fibrosis may be determined using, for example, delayed enhancement MRI of the heart in whole or in part.

In another aspect, the invention provides a compound having a structure selected from the group consisting of

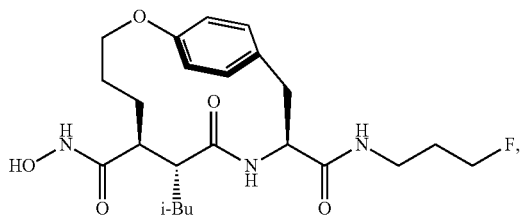

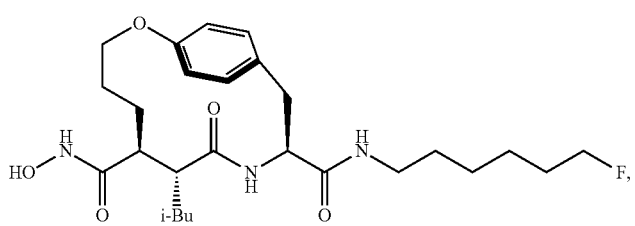

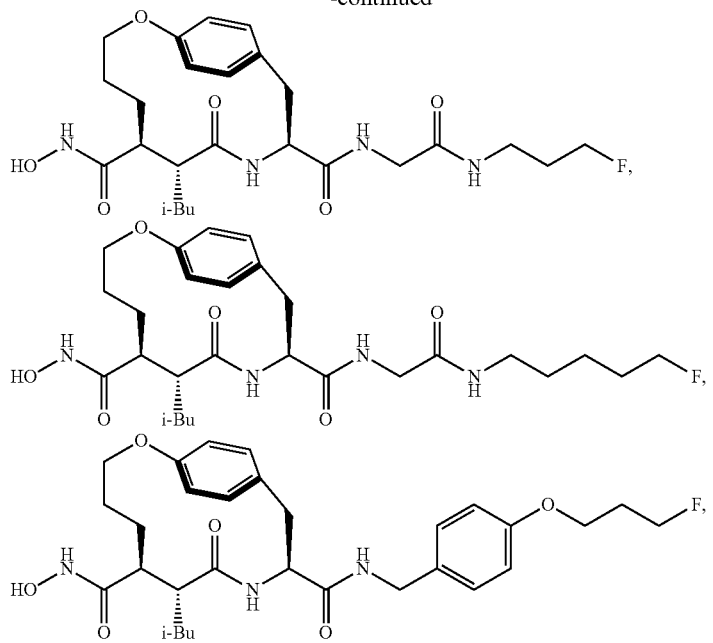

wherein F represents an isotopically-enriched population of $^{18}F$, and variants thereof comprising, instead of F, an isotopically enriched imaging moiety selected from the group consisting of $^{11}C$, $^{13}N$, $^{123}I$, $^{125}I$, $^{99m}Tc$, $^{95}Tc$, $^{111}In$, $^{62}Cu$, $^{64}Cu$, $^{67}Ga$, and $^{68}Ga$.

In another aspect, the invention provides a composition comprising any of the foregoing compounds, and a pharmaceutically acceptable carrier.

In another aspect, the invention provides use or methods of use of the foregoing compounds in medical imaging techniques.

In another aspect, the invention provides methods for determining the presence of an atherosclerotic plaque in a subject comprising administering to a subject an imaging agent comprising an MMP inhibitor linked to an imaging moiety and acquiring an image of a portion of the subject (e.g., an image of the cardiovasculature); and determining the presence of an atherosclerotic plaque at least in part based on the presence of an increased amount of imaging agent in the imaged portion of the subject (for example, as compared to a region that does not contain an atherosclerotic plaque).

In another aspect, the invention provides methods for determining the effectiveness of an anti-lipid therapy on atherosclerosis (e.g., on atherosclerotic plaque biology or morphology) in a subject comprising administering to a subject a first dose of an imaging agent comprising an MMP inhibitor linked to an imaging moiety and acquiring at least one first image of a portion of the subject; administering an anti-lipid therapy to the subject; administering a second dose of an imaging agent comprising an MMP inhibitor linked to an imaging moiety to the subject and acquiring at least one second image of a portion of the subject; determining the change in the amount of imaging agent in the portion of the subject between the at least one first image and the at least one second image; and determining the effectiveness of the anti-lipid therapy based at least in part on the change in the amount of the imaging agent in the portion of the subject between the first image and the second image. The portion of the subject being imaged is typically the cardiovasculature such as the coronary arteries and the like.

In another aspect, the invention provides methods of determining the presence of calcific aortic valve disease (CAVD) in a subject and/or determining a subject's risk of developing CAVD comprising administering to a subject an imaging agent comprising an MMP inhibitor linked to an imaging moiety and acquiring a first cardiac image of the subject; and determining the presence of CAVD and/or a subject's risk of developing CAVD based at least in part on the first cardiac image. The cardiac image typically includes or is of the cardiac valve, optionally including the leaflets. In accordance with the invention, increased uptake of the imaging agent in the aortic valve region is indicative of the presence of CAVD or the increased risk of developing CAVD. In some embodiments, the subject being imaged does not have atherosclerosis (e.g., the subject does not manifest symptoms associated with atherosclerosis, and is referred to as "asymptomatic" for this condition). The uptake of an MMP inhibitor linked to an imaging moiety in a particular portion of a subject can allow for the imaging of tissue remodeling characterized in part by macrophage infiltration, MMP activation, and the like, in a portion of the subject, as a diagnostic indicator of CAVD.

In another aspect, the invention provides methods of determining the progression of CAVD in a subject comprising administering to the subject a first dose of an imaging agent comprising an MMP inhibitor linked to an imaging moiety and acquiring at least one first cardiac image of the subject; administering a second dose of an imaging agent comprising an MMP inhibitor linked to an imaging moiety and acquiring at least one second cardiac image of the subject; determining the change in the amount of imaging agent in the heart or a portion of the heart between the first image and the second image; and determining the progression of CAVD in the subject based at least in part on the change in the amount of the imaging agent in the heart or the portion of the heart between the at least one first image and the at least one second image. In important embodiments, the image includes or is of the aortic valve, optionally including the leaflets. In some embodiments, the method comprises administering more than two doses of the imaging agent, obtaining more than two cardiac images, and determining the progression of CAVD based at least in part on the change in the amount of the imaging agent in the heart or the portion of the heart between the obtained images.

In another aspect, the invention provides methods of determining the effectiveness of a treatment for CAVD in a subject comprising administering to a subject a first dose of an imaging agent comprising an MMP inhibitor linked to an imaging moiety and acquiring at least one first cardiac image of the subject; administering a treatment for CAVD to the subject; administering a second dose of an imaging agent comprising an MMP inhibitor linked to an imaging moiety and acquiring at least one second cardiac image of the subject; determining the change in the amount of imaging agent in the heart or a portion of the heart between the first image and the second image; and determining the effectiveness of the treatment for CAVD based at least in part on the change in the amount of the imaging agent in the heart or a portion of the heart between the at least one first image and the at least one second image. In important embodiments, the image includes or is of the aortic valve, optionally including the leaflets. The invention contemplates that effectiveness of the treatment will be evidenced by a decreased amount (and in some instances a constant or unchanged amount) of imaging agent in the heart, and in particular in the aortic valve region, optionally including the leaflets.

In various imaging methods set forth herein, two or more images may be obtained from a subject. This may be the case where for example the subject is undergoing a treatment and/or other intervention between images or where it is desired to monitor the progression of or towards a condition in the absence of treatment or significant intervention. Treatment may be an anti-lipid therapy, although it is not so limited. Intervention may be a change in lifestyle, including for example weight loss, cessation of smoking, increased exercise, and the like, although it too is not so limited. When two or more images are obtained from a subject, the images may be randomly spaced or regularly spaced in time, including for example about weekly, biweekly, monthly, bimonthly, every 6 months, or yearly.

These and other aspects of the invention will be described in greater detail herein.

DETAILED DESCRIPTION OF INVENTION

Figure 1:
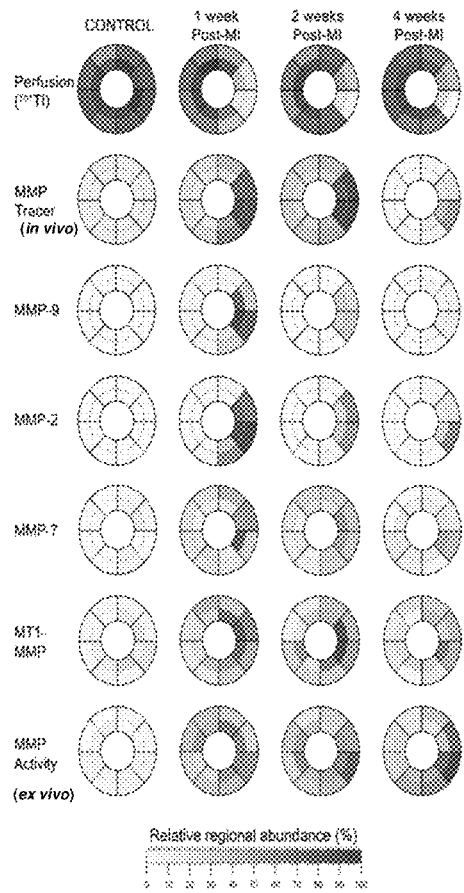
FIG. 1. Comparison of myocardial $^{201}$Tl and $^{99m}$Tc-RP805 activity with MMP zymography in pig hearts 1, 2, and 4 weeks post-MI. Shown are color coded spatial maps of relative myocardial $^{201}$Tl activity (top row), $^{99m}$Tc-RP805 activity (second row), MMP-9 activity assessed by zymography (third row), total and active MMP-2 activity assessed by zymography (fourth and fifth rows), MMP-7 levels (sixth row), MT1-MMP levels (seventh row), and MMP activity determined as a function of cleavage of a fluorescent substrate (seventh row). Images are oriented with the lateral wall on the right. Note the time dependent changes in regional $^{99m}$Tc-RP805 activity correlate with spatial and temporal changes in MMP levels/activity as assessed by zymography. Reference color bar is at the bottom. Relationship between in vivo and in vitro determination of MMP activity (upper right). In vivo MMP activity, determined as retention of $^{99m}$Tc-RP805, was significantly related to in vitro changes in levels of active MMP-2 ($y=1687e^{0.033x}$, r:0.89, p<0.05). (lower right) There was a significant relationship between the change in body mass indexed LV end-diastolic volume relative to control values and MMP activity within the MI region ($y=31.34e0.48x$, r=0.38, p=0.04).
Figure 1:
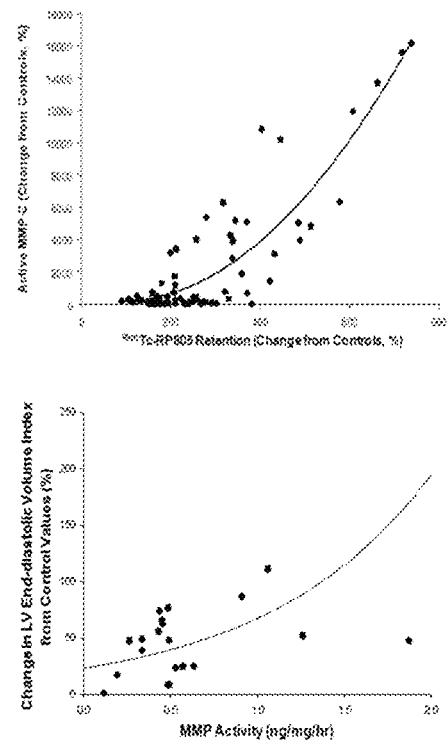

The invention is based, in part, on the unexpected finding that MMP levels, and in some instances more specifically cardiovascular MMP levels, aortic valve MMP levels, and/or cardiac MMP levels, can be observed using, for example, MMP inhibitors linked to imaging moieties, and that such MMP levels can be used to evaluate the presence of (including early detection of) or the likelihood of developing certain conditions, the progression of the condition, and the effectiveness of treatments and/or interventions directed towards such conditions including prophylactic or therapeutic treatments. The invection contemplates that increased MMP levels (and thus increased MMP activity) is indicative of tissue (e.g., vascular) remodeling observed in certain cardiovascular conditions and/or that predisposes certain cardiovascular conditions such as but not limited to AF.

Some aspects of the invention relate to determining the presence of or the risk of developing AF. In some embodiments, cardiac MMP levels are indicative of whether a subject is likely to develop AF, either as a primary event or as a recurrence. The methods of the invention can be used to identify subjects having an increased risk (as compared to the risk of control or "normal" subjects) of developing AF. Subjects identified in this manner may then be monitored more closely (including more regularly) or they may be treated at an earlier time point than previously contemplated in order to reduce the risk that AF will ultimately develop. In some embodiments, any increased MMP level relative to control is used to identify subjects at increased risk. In some embodiments, the MMP level (over control level) is used to quantify the risk of developing AF. In these latter instances, lower MMP levels may correlate with lower risk and higher MMP levels may correlate with higher risk of AF. It is to be understood that MMP levels may be indicated by retention levels of MMP imaging agents of the invention.

The invention also contemplates a method for determining a treatment regimen for a subject having AF as well as a method of determining the likelihood of response to a treatment in a subject having a history of AF. The method comprises administering to a subject (having AF and/or having a history of AF) an imaging agent of the invention and obtaining a heart (cardiac) image of the subject, wherein the MMP level in the subject indicates whether the subject should be treated using electrical cardioversion or an alternative treatment such as pharmacological rate or rhythm management, ablation and/or an implantable rate device. The invention thus provides, in some embodiments, methods to direct the clinical management strategy of such AF subjects between rate control (including pharmacological rate control) or rhythm control (including device-based and/or pharmacological rhythm control) treatments.

The invention further contemplates a method for determining the extent and complexity of ablation therapy that may be needed to treat AF in a subject.

MMPs and AF

Atrial fibrosis is a hallmark of structural remodeling that contributes to the AF substrate. Left atrial tissue has been shown in patients and in animal models of AF to contain deposits of fibrillar collagen and expansion of the extracellular matrix (ECM). Histologically determined extent of fibrosis and ECM expansion has been shown to correlate with AF persistence (Circ 2004; 109:363-368). Delayed enhancement MRI has been used to image left atrial fibrosis and has shown more fibrosis in patients with persistent AF compared to paroxysmal AF (Circ Cardiovasc Imaging 2010; 3:231-239). As significant fibrosis is relatively permanent, there would be greater clinical benefit to detecting the presence and extent of more proximate pathologies. The role that MMPs play in ECM remodeling suggests their utility in this context. Indeed, in a canine model of heart failure, administration of an MMP inhibitor attenuated the vulnerability to AF and reduced atrial fibrosis compared to control animals (J Cardiac Failure 2008; 14:768-776). In patients in whom pharmacologic or electrical cardioversion was attempted, refractory AF was significantly associated with elevated MMP-2 levels (Europace 2009; 11:332-337). US 2011/0009861 discloses methods of predicting AF recurrence comprising detecting specified amounts of MMPs in body fluids.

The methods of this invention provide non-invasive methods to evaluate levels of MMPs in the atria and in so doing ensure the relevant origin of the MMP. As MMPs play a role in numerous normal and pathologic processes, MMP levels measured in a body fluid cannot be assured to represent MMP levels in the atrium. Additionally, the spatial extent of MMP activity, as may be determined using the methods of this invention, will predict the spatial extent of fibrosis. Such spatial extent cannot be determined by a body fluid measure.

Provided are profiles of quantities, intensities, concentrations, spatial distribution and/or localization of an imaging agent comprising an MMP inhibitor that are an indication of increased risk of developing primary or recurrent AF. The profiles that are indication of higher risk of recurrence of AF in a subject can be relative to a normal value. A normal value of an imaging agent comprising an MMP inhibitor can be a reference value for an age matched subject that is confirmed to have no evidence of significant cardiovascular disease, or of AF. Thus, the normal value can be a population-based value derived from a significant number of healthy individuals. These reference normal values can be obtained from population based studies.

Methods are also provided for determining whether a subject with a history of AF should be treated with an implantable pacer. These methods can comprise measuring retention of an imaging agent comprising an MMP inhibitor in the subject to produce a retention profile (that acts as a surrogate for MMP levels). The produced profile can be used to determine, inter alia, whether the subject will have a recurrence of AF following a therapy such as a cardioversion procedure, a likely recurrence of AF indicating treatment with an implantable pacer.

Prognosis

Provided herein is a method of predicting recurrence of AF in a subject, comprising measuring retention of an imaging agent, comprising an MMP inhibitor in a subject and comparing said levels to reference values.

As used herein "recurrence" can include paroxysmal, persistent, and chronic episodes of AF in a subject that has experienced a prior episode of AF and may or may not have been treated (including successfully treated in the short term) for the prior episode of AF. Predicting recurrence of AF in a subject with a history of (including presenting with) AF can be done prior to administration of AF treatment and to determine if the selected AF treatment will likely be followed by recurrence of AF in that subject. For example, the recurrence of AF can be predicted prior to electrical cardioversion. If it is determined that electrical cardioversion will correct the AF without recurrence of AF then electrical cardioversion can be selected as the treatment modality of choice. If it is determined that electrical cardioversion will not result in sustained AF correction, then another treatment modality can be selected. For example, an implantable pacer device can be selected or pharmacological pacing can be used instead of electrical cardioversion if it is determined that there will be recurrence with electrical cardioversion. Moreover, retention level of an imaging agent comprising an MMP inhibitor can be used to select treatment with an implantable pacer device, ablation, or by pharmacological pacing.

The method of the invention can further comprise the steps of measuring a ventricular perfusion defect and measuring uptake of an imaging agent comprising an MMP inhibitor. Thus, the method can comprise performing a resting flurpiridaz F 18 perfusion study, determining the summed rest score from said study, quantifying atrial uptake of an imaging agent comprising an MMP inhibitor and determining risk of recurrent AF.

The invention further contemplates using cardiovascular MMP levels to evaluate conditions other than AF. In some embodiments, MMP levels may be useful for determining the presence of atherosclerotic plaques in a subject and/or the effectiveness of anti-lipid therapies (e.g., employed for the treatment of atherosclerosis) on plaque biology in a subject. In some embodiments, cardiac MMP levels (including levels in the aortic valve region) can be used to determine the presence of CAVD in a subject, to determine a subject's risk of developing CAVD, to determine progression of CAVD in a subject, and/or to determine the effectiveness of a treatment for CAVD in a subject. These and other aspects and embodiments of the invention will be described in greater detail herein.

MMPs and Atherosclerosis

Atherosclerosis, a major cause of morbidity and mortality in the US, is linked to hyperlipidemia. Pharmacologic treatment of hyperlipidemia is a common treatment for atherosclerotic diseases and is believed to be related at least in part to "stabilizing" effects on atherosclerotic plaque biology. The term "atherosclerosis" is given its ordinary meaning in the art and refers to a disease of the arterial wall in which the wall area thickens, causing narrowing of the channel and thus impairing blood flow. Atherosclerosis may occur in any area of the body, but can be most damaging to a subject when it occurs in the heart, brain, or blood vessels leading to the brain stem. Atherosclerosis includes thickening and hardening of arterial walls or the accumulation of fat, cholesterol and other substances that form atheromas or plaques. Atherosclerosis may also result from calcification, hemorrhage, ulceration, thrombosis, and/or trauma.

As noted above, in some embodiments, the invention provides non-invasive methods to evaluate levels of MMPs in a portion of a subject. In some embodiments, imaging of MMPs (e.g., MMP activation in vivo) may be used to determine the presence of an atherosclerotic plaque in a subject. In some embodiments, serial imaging of MMPs (e.g., MMP activation in vivo) may be used to determine the effectiveness of an anti-lipid therapy on plaque biology in a subject. For example, a series of images may be obtained during and/or following the course of administration of a treatment for atherosclerosis to a subject, and the images may be analyzed to determine effectiveness of the treatment. An efficacious treatment is indicated by a reduced level of MMP activation in the imaged region. An efficacious treatment may also be indicated by an unchanged level of MMP activation in the imaged region, in some instances. A non-efficacious treatment is indicated by an increased level of MMP activation in the imaged region, in some instances.

In some embodiments, a method of determining the presence of an atherosclerotic plaque in a subject comprises administering to the subject an imaging agent comprising an MMP inhibitor linked to an imaging moiety and acquiring at least one first image of a portion of the subject. The presence of an atherosclerotic plaque may be determined based on the amount of imaging agent present in the imaged portion of the subject. In some cases, the portion of the subject is the heart or a portion of the heart (e.g., the aortic arch).

In some embodiments, the location and/or concentration of MMPs determined from the images may be analyzed relative to a normal value. A normal value of an imaging agent of the invention can be a reference value for an age-matched subject that is confirmed to have no evidence of significant atherosclerosis. Thus, the normal value can be a population-based value derived from a significant number of healthy individuals. These reference normal values can be obtained from population-based studies. The normal value may be determined based on imaging agent uptake in the aortic arch.

In some embodiments, a method of determining the effectiveness of an anti-lipid therapy on plaque biology in a subject comprises administering to the subject a first dose of an imaging agent comprising an MMP inhibitor linked to an imaging moiety and acquiring at least one first image of a portion of the subject. An anti-lipid therapy may then be administered to the subject. Following and/or concurrent to administration of the anti-lipid therapy, the subject may be administered a second dose of an imaging agent comprising an MMP inhibitor linked to an imaging moiety and at least one second image of a portion of the subject may be acquired. The change (e.g., decrease and/or increase) in the amount of imaging agent in the portion of the subject between the first image and the second image may be determined. The effectiveness of the anti-lipid therapy may be determined based at least in part on the change in the amount of the imaging agent in the portion of the subject between the first image and the second image. In some cases, a decrease in the amount of imaging agent in the portion of the subject indicates that the anti-lipid therapy is effective in reducing the amount of plaque in the subject. In some cases, the portion of the subject is the heart or a portion of the heart. In some cases, the change in the amount of imaging agent in the aortic arch may be analyzed/determined. In some cases, a lack of an increase in the amount of imaging agent in the imaged portion of the subject (i.e., a constant level or a decreased level) may also indicate an effective anti-lipid therapy.

In some embodiments, the subject may be administered additional doses of an imaging agent comprising an MMP inhibitor linked to an imaging moiety and additional images of a portion of the subject may be acquired. The change in the amount of imaging agent in the portion of the subject between two images, or more than two images, may be used to determine the effectiveness of the anti-lipid therapy.

Those of ordinary skill in the art will be aware of anti-lipid therapies which may be used to treat atherosclerosis in a subject, for example, statins (e.g., rosuvastatin), fibrates (e.g., gemfibrozil, fenofibrate), dietary changes, etc.

In some important embodiments, the imaging agent comprises the structure:

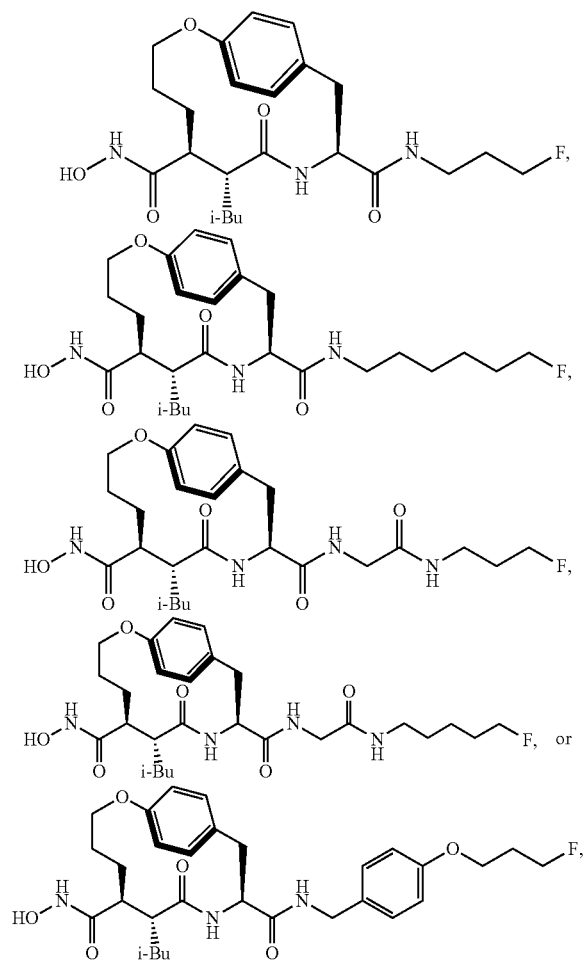

wherein F represents an isotopically-enriched population of $^{18}$F, and variants thereof comprising, instead of F, an isotopically enriched imaging moiety selected from the group consisting of $^{11}$C, $^{13}$N, $^{123}$I, $^{125}$I, $^{99m}$Tc, $^{95}$Tc, $^{111}$In, $^{62}$Cu, $^{64}$Cu, $^{67}$Ga, and $^{68}$Ga.

MMPs and Calcific Aortic Valve Disease (CAVD)

Calcific aortic valve disease (CAVD) is common among the elderly population. Inflammation and matrix remodeling play a central role in progression of CAVD to symptomatic aortic stenosis. MMPs are upregulated in CAVD. Generally, the term "calcific aortic valve disease" encompasses a disease spectrum from initial alterations in the cell biology of the leaflets to end-stage calcification resulting in left ventricular outflow obstruction. Disease progression is generally characterized by a process of thickening of the valve leaflets and the formation of calcium nodules—often including the formation of actual bone—and new blood vessels, which are concentrated near the aortic surface. End-stage disease, e.g., calcific aortic stenosis, is generally characterized pathologically by large nodular calcific masses within the aortic cusps that protrude along the aortic surface into the sinuses of Valsalva, interfering with opening of the cusps.

As noted above, in some embodiments, the invention provides non-invasive methods to evaluate levels of MMPs in a portion of the subject. In some embodiments, imaging of MMPs (e.g., MMP activation in vivo) can be used to determine the presence of CAVD in a subject (including early detection and/or diagnosis prior to irreversible injury), to determine a subject's risk of developing CAVD, to determine progression of CAVD in a subject, and/or to determine the effectiveness of a treatment for CAVD in subject. For example, a single image may be obtained of a subject, wherein the image may be analyzed to determine the presence of CAVD in a subject and/or the subject's risk of developing CAVD. As another example, a series of images may be obtained of a subject over a period of time, wherein the images may be analyzed to determining the progression of CAVD in the subject and/or the effectiveness of a treatment for CAVD.

In some embodiments, a method of determining the presence of CAVD in a subject and/or determining a subject's risk of developing CAVD comprises administering to the subject an imaging agent comprising an MMP inhibitor linked to an imaging moiety and acquiring a first cardiac image of the subject. The presence of CAVD in the subject and/or the subject's risk of developing CAVD may be based at least in part on the first cardiac image. In some cases, the amount of imaging agent in the aortic valve may be analyzed/determined. In some embodiments, the subject is asymptomatic for atherosclerosis.

The images and related MMP values may be analyzed relative to a normal value. A normal value of an imaging agent comprising an MMP inhibitor can be a reference value for an age-matched subject that is confirmed to have no evidence of significant CAVD. Thus, the normal value can be a population-based value derived from a significant number of healthy individuals. These reference normal values can be obtained from population-based studies. The normal value may be determined based on the level of imaging agent uptake in a portion of the heart (e.g., aortic valve).

In some embodiments, the images obtained of a portion of a subject (e.g., of a subject's aortic valve) may be analyzed in connection with and/or with reference to other images or data obtained from the subject. For example, in some cases, the images obtained of a subject's aortic valve indicating MMP levels may be analyzed in connection with and/or with reference to a CT scan of the subject's aortic valve, wherein the CT may indicate the presence or absence of calcification of the subject's aortic valve. Other non-limiting examples including a subject's cholesterol levels (e.g. LDL levels), blood pressure, and/or cardiac dysfunction (e.g., as determined by ultrasound or EKG). In some cases, the subject may have been diagnosed as having or as being at risk of developing CAVD and/or atherosclerosis. In other cases, the subject may be asymptomatic and/or may have not been diagnosed as having CAVD and/or atherosclerosis. In some instances, the images obtained using for example another imaging agent and/or another modality may provide no evidence of calcification and thus the subject may be one that manifests no calcification and yet is experiencing the early stages of CAVD (i.e., precalcification stages of CAVD).

In some embodiments, a method of determining the progression of CAVD in a subject comprises administering to the subject a first dose of an imaging agent comprising an MMP inhibitor linked to an imaging moiety and acquiring at least one first cardiac image of the subject. At a later time point, the subject may be administered a second dose of an imaging agent comprising an MMP inhibitor linked to an imaging moiety and at least one second cardiac image of the subject may be acquired. The change (e.g., decrease and/or increase) in the amount of imaging agent in the heart or a portion of the heart between the first image and the second image may be determined. The progression of CAVD in a subject may be determined based at least in part on the change in the amount of the imaging agent in the heart or a portion of the heart between the first image and the second image. In some cases, the change in the amount of imaging agent in the aortic valve may be analyzed/determined.

In some embodiments, a method of determining the effectiveness of a treatment for CAVD in a subject comprises administering to a subject a first dose of an imaging agent comprising an MMP inhibitor linked to an imaging moiety and acquiring at least one first cardiac image of the subject. The treatment for CAVD may then be administered to the subject. Following and/or concurrent to administration of the treatment for CAVD, the subject may be administered a second dose of an imaging agent comprising an MMP inhibitor linked to an imaging moiety and at least one second cardiac image of the subject may be acquired. The change (e.g., decrease and/or increase) in the amount of imaging agent in the heart or a portion of the heart between the first image and the second image may be determined. The effectiveness of the treatment for CAVD may be determined based at least in part on the change in the amount of the imaging agent in the heart or a portion of the heart between the first image and the second image. In some cases, the lack of an increase in the amount of the imaging agent in the imaged portions of the subject may indicate effectiveness of the treatment. In some cases, the change in the amount of imaging agent in the aortic valve may be analyzed/determined.

In some embodiments, the imaging agent is $^{99m}$Tc-RP805 or $^{111}$In-RP782. In some important embodiments, the imaging agent comprises the structure:

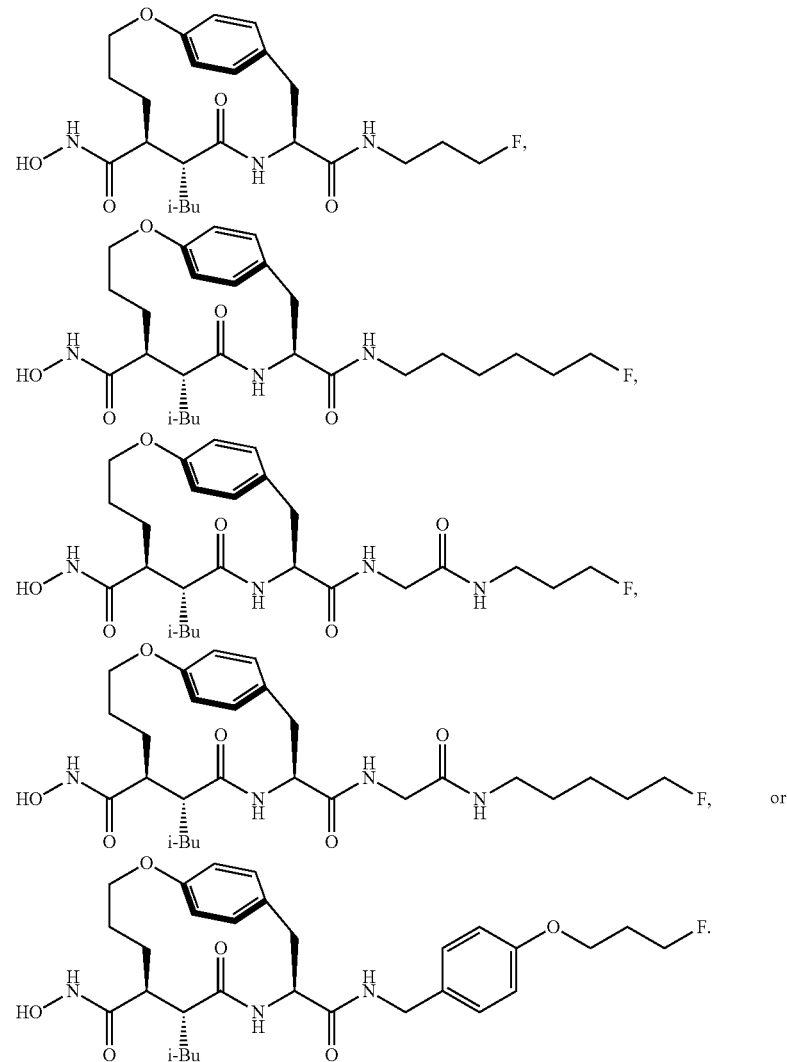

wherein F represents an isotopically-enriched population of $^{18}$F, and variants thereof comprising, instead of F, an isotopically-enriched imaging moiety selected from the group consisting of $^{11}$C, $^{13}$N, $^{123}$I, $^{125}$I, $^{99m}$Tc, $^{95}$Tc, $^{111}$In, $^{62}$Cu, $^{64}$Cu, $^{67}$Ga, and $^{68}$Ga.

Imaging Agents

The imaging agents of the invention comprise an MMP inhibitor linked to an imaging moiety. Localization of the MMP inhibitor (e.g., through binding to MMP resident in a tissue) is indicative of the MMP level which in turn is indicative of MMP activity. As will be understood, MMP inhibitor presence, location and/or amount is detected by virtue of the imaging moiety linked to the MMP inhibitor.

MMP inhibitors refer to agents that bind to one or more MMPs. The MMPs may be but are not limited to MMP-2, MMP-9 and/or MMP-14. Preferably, the MMP inhibitors bind to one or more MMPs for a period of time that is sufficient to detect their presence in the tissue being imaged.

As used herein, an "imaging moiety" refers to an atom or group of atoms that is capable of producing a detectable signal itself or upon exposure to an external source of energy (e.g., imaging agents comprising imaging moieties may allow for the detection, imaging, and/or monitoring of the presence and/or progression of a condition), pathological disorder, and/or disease. Nuclear medicine imaging agents can include $^{11}C$, $^{13}N$, $^{123}I$, $^{125}I$, $^{99m}Tc$, $^{95}Tc$, $^{111}In$, $^{62}Cu$, $^{64}Cu$, $^{67}Ga$, and $^{68}Ga$ as the imaging moiety. In some embodiments, the imaging moiety is $^{18}F$.

In some embodiments, a compound (e.g., an imaging agent, a fluoride species) may be isotopically-enriched with fluorine-18. "Isotopically-enriched" refers to a composition containing isotopes of an element such that the resultant isotopic composition is other than the natural isotopic composition of that element. With regard to the compounds provided herein, when a particular atomic position is designated as $^{18}F$, it is to be understood that the abundance of $^{18}F$ at that position is substantially greater than the natural abundance of $^{18}F$, which is essentially zero. In some embodiments, a fluorine designated as $^{18}F$ may have a minimum isotopic enrichment factor of about 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The isotopic enrichment of the compounds provided herein can be determined using conventional analytical methods known to one of ordinary skill in the art, including mass spectrometry and HPLC.

Imaging moieties include, without limitation, radioisotopes, paramagnetic metal atoms, gas-filled microspheres, and the like. It will be understood that the nature of the imaging moiety will depend in large part on the imaging modality to be used. As an example, imaging moieties that are radioisotopes are known to be useful for imaging by gamma scintigraphy or positron emission tomography (PET), and thus would be suitable if such imaging modalities were being used in the methods of the invention. As another example, the imaging moiety may be a metallic radioisotope or a paramagnetic metal atom suitable for magnetic resonance imaging (MRI). In these instances, the MMP inhibitor may be linked to one or more chelators, and the imaging moiety binds to the chelator(s). In these instances, the imaging moiety is non-covalently linked to the MMP inhibitor via the chelator. As yet another example, the MMP inhibitor may be linked to gas-filled microspheres when ultrasound is the imaging modality of choice. The MMP inhibitor may be linked to the material that encapsulates and/or stabilizes such microspheres. In an important embodiment, the imaging moiety is $^{18}F$.

Each MMP inhibitor may be linked to one or more imaging moieties. The MMP inhibitors may be directly or indirectly linked to an imaging moiety. Indirect linkage may involve the use of a linker or a spacer. Linkage may be covalent or non-covalent. In important embodiments, covalent linkage is preferred.

Imaging agents suitable for use in the methods of the invention are shown below along with their precursors:

| Imaging Agent Precursors | Imaging Agents |
| --- | --- |
| 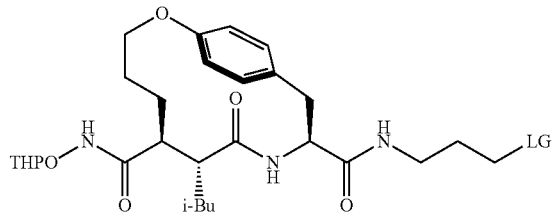 | 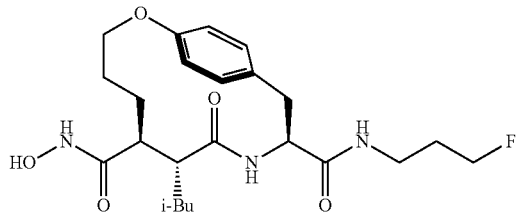 |
| 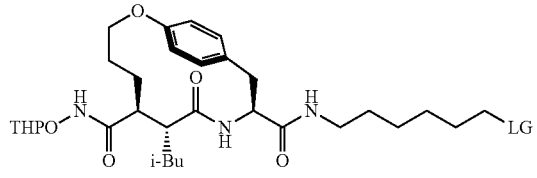 | 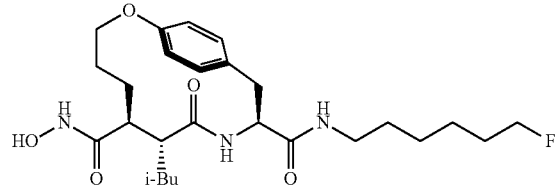 |
| 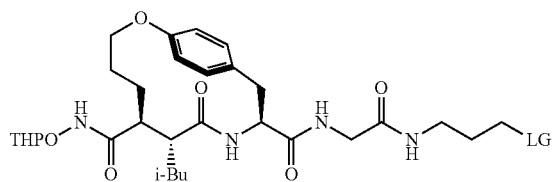 | 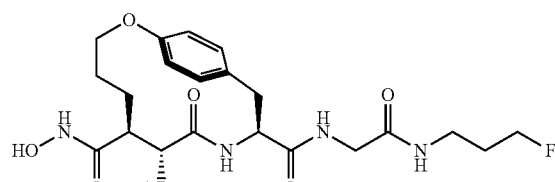 |

| Imaging Agent Precursors | Imaging Agents |
|---|---|
| 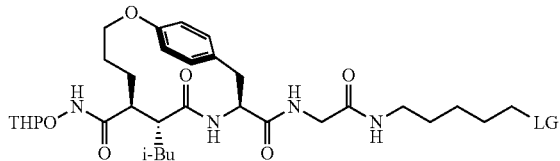 | 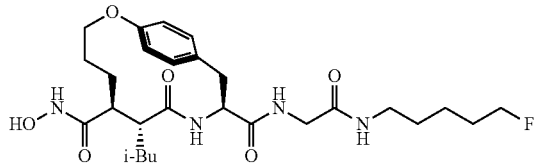 |
| 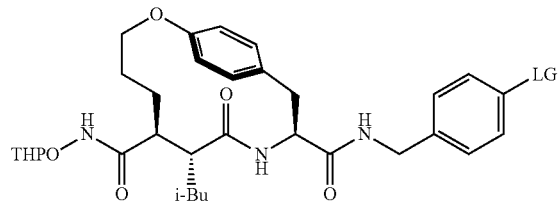 | 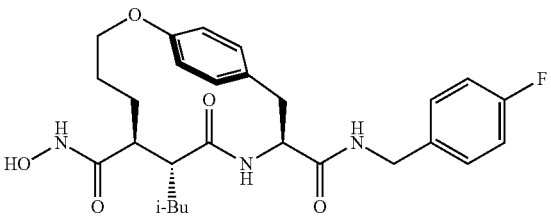 |
| 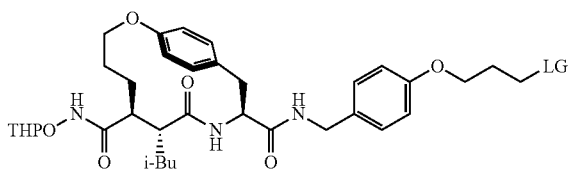 | 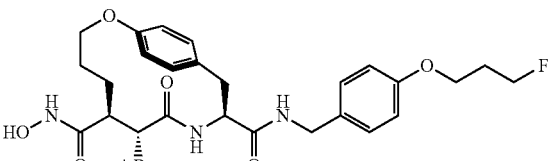 |

The imaging agents of Table 1 may be synthesized from the precursors also shown in Table 1. LG refers to the leaving group and may be but is not limited to tosylates and mesylates. Methods for synthesizing imaging agents from tosylate or other precursor forms are described in published PCT application WO 2011/097649.

Other imaging agents suitable for use in the methods of the invention include those described in U.S. Pat. No. 6,656,448 and in U.S. Pat. No. 6,989,139, the specific teachings of which are incorporated by reference herein.

Those of ordinary skill in the art will be aware of methods for synthesizing the imaging agents and imaging agent precursors described herein. For example, see the methods disclosed in the Examples section as well as those described in U.S. Pat. No. 6,656,448 and in U.S. Pat. No. 6,989,139, the specific teachings of which are incorporated by reference herein.

Some imaging agents suitable for use in the methods of the invention include those having one of the two following structures:

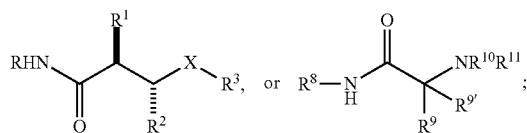

wherein, R is independently OH or —CH$_2$SH; R$^1$ is independently selected at each occurrence from the group: H, OH, C$_1$-C$_3$ alkyl, C$_2$-C$_3$ alkenyl, C$_2$-C$_3$ alkynyl, and heterocycle-S—CH$_2$—; R$^2$ is independently C$_1$-C$_{20}$ alkyl; X is independently C=O or SO$_2$ provided when X is C=O, R$^3$ is

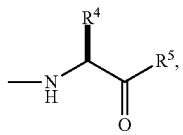

and when X is SO$_2$, R$^3$ is independently selected from the group: aryl substituted with 0-2 R$^6$, and heterocycle substituted with 0-2 R$^6$; R$^4$ is independently selected at each occurrence from the group: C$_1$-C$_6$ alkyl, phenyl, and benzyl; R$^5$ is independently at each occurrence from the group:
NH(C1-C6 alkyl), NH-phenyl, and NH-heterocycle; wherein said alkyl, phenyl and heterocycle groups are optionally substituted with a bond to the linking group or a bond to the chelator; R$^6$ is independently aryloxy substituted with 0-3 R$^7$; R$^7$ is independently halogen or methoxy;
or alternatively, R$^1$ and R$^4$ may be taken together to form a bridging group of the formula —(CH$_2$)$_3$—O-phenyl-CH$_2$—, optionally substituted with a bond to the linking group or a bond to the chelator; or alternatively, R$^1$ and R$^2$ may be taken together to form a bridging group of the formula —(CH$_2$)$_3$—NH—, optionally substituted with a bond to the linking group or a bond to the chelator; or R and R$^2$ taken together with the nitrogen and carbon atom through which they are attached form a C$_{5-7}$ atom saturated ring system substituted with one or more substituents selected from the group consisting of: a bond to L$_n$, where L$_n$ is a linking group between the matrix metalloproteinase inhibitor and chelator a bond to C$_h$, and —C=O—NR$^{29}$R$^{30}$; where C$_h$ is a chelator, R$^8$ is independently at each occurrence OH or phenyl, optionally substituted with a bond to the linking group or a bond to the chelator, provided that when R$^8$ is phenyl, R$^{10}$ is —C(=O)—CR$^{12}$—NH—CH(CH$_3$)—COOH; R$^9$ and R$^{9'}$ are independently H, C1-C6 alkyl optionally substituted with a bond to the linking group or a bond to the chelator, or are taken together with the carbon atom to which $R^9$ and $R^{9'}$ are attached to form a 5-7 atom saturated, partially unsaturated or aromatic ring system containing 0-3 heteroatoms selected from O, N, $SO_2$ and S, said ring system substituted with $R^6$ and optionally substituted with a bond to the linking group or a bond to the chelator; $R^{10}$ and $R^{11}$ are independently H, or C1-C6 alkyl optionally substituted with a bond to the linking group or a bond to the chelator, or are taken together with the nitrogen atom to which they are attached to form a 5-7 atom saturated, partially unsaturated or aromatic ring system containing 0-3 heteroatoms selected from O, N, $SO_2$ and S, said ring system optionally substituted with 0-3 $R^{27}$, a bond to the linking group or a bond to the chelator; or alternatively, $R^9$ and $R^{10}$ are taken together with the carbon atom to which they are attached to form a 5-7 atom saturated, partially unsaturated or aromatic ring system containing 0-3 heteroatoms selected from O, N, $SO_2$ and S, said ring system optionally substituted with a bond to the linking group or a bond to the chelator; and $R^2$ is independently C1-C20 alkyl; $R^{27}$ is =O, C1-4 alkyl, or phenyl substituted with $R^{28}$; $R^{28}$ is a phenoxy group substituted with 0-2 $OCH_3$ groups; $R^{29}$ and $R^{30}$ taken together with the nitrogen atom through which they are attached form a C5-7 atom saturated ring system substituted with $R^{31}$ and $R^{31}$ is a benzyloxy group substituted with C1-4 alkyl. In all of the foregoing embodiments, a metallic imaging moiety is chelated by the chelator.

Still other imaging agents comprise (a) an imaging moiety that is a diagnostic metal, and (b) a compound selected from 2-{[5-(3-{2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino}propylcarbamoyl)-pyridin-2-yl]-hydrazonomethyl}-benzenesulfonic acid;

2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzene sulfonic acid;

2-[7-({N-[3-(2-{[7-(N-hydroxycarbamoyl)(3S,6R,7S)-4-aza-6-(2-methylpropy 1)-11-oxa-5-oxobicyclo[10.2.2] hexadeca-1(15), 12(16), 13-trien-3-yl]carbonyl-amino}acetyl amino) propyl]carbamoyl}methyl)-1,4,7,10-tetraaza-4,10-bis(carboxymethyl)cyclododecyl]acetic acid;

2-{7-[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16), 13-trien-3-yl]-carbonyl-amino}methyl)phenyl]methyl}carbamoyl)methyl]-1,4,7,10-tetraaza-4,10-bis(carboxymethyl)cyclododecyl}acetic acid;

2-(7-{[N-(1-{N-[3-(2-{[7-(N-hydroxycarbamoyl)(3S,6R,7S)-4-aza-methylpropyl)-11-oxa-5-oxobicyclo[10.2.2]hexadeca-1(15), 12(16), 13-trien-3-yl]carbonyl-amino}acetylamino)propyl]carbamoyl}-2-sulfoethyl)carbamoyl]methyl}-1,4,7,10-tetraaza-4,10-bis(carboxymethyl)cyclododecyl)acetic acid;

2-[7-({N-[1-(N-{[4-({[7-(N-hydroxycarbamoyl)(3S,6R,7S)-4-aza-6-(2-methylpropyl)-11-oxa-5-oxobicyclo[10.2.2]hexadeca-1 (15),12(16),13-trien-3-yl]carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid;

2-({2-[({N-[3-(2-{[7-(N-hydroxycarbamoyl)(3S,6R,7S)-4-aza-6-(2-methyl propyl)-11-oxa-5-oxo bicyclo[10.2.2] hexadeca-1(15),12(16),13-trien-3-yl] carbonylamino}acetylamino)propyl]carbamoyl}methyl)(carboxymethyl)amino}ethyl){2-[bis(carboxymethyl)amino]ethyl}amino]acetic acid;

2-[(2-{[(N-{[4-({[7-(N-hydroxycarbamoyl)(3S,6R,7S)-4-aza-6-(2-methylpropyl)-11-oxa-5-oxo bicyclo[10.2.2] hexadeca-1(15),12(16),13-trien-3-yl] carbonylamino}methyl)phenyl]methyl}carbamoyl) methyl](carboxymethyl)amino}ethyl){2-[bis(carboxymethyl)amino]ethyl}amino]acetic acid;

N-[3-(2-{[7-(N-hydroxycarbamoyl)(3S,6R,7S)-4-aza-6-(2-methylpropyl)-11-oxa-5-oxo bicyclo[10.2.2]hexadeca-1(15), 12(16), 13-trien-3-yl]carbonyl-amino}acetylamino) propyl]-4,5-bis[2-(ethoxyethyl-thio)acetylamino]pentanamide;

N-{[4-({[7-(N-hydroxycarbamoyl)(3S,6R,7S)-4-aza-6-(2-methylpropyl)-11-oxa-5-oxo bicyclo[10.2.2]hexadeca-1(15),12(16),13-trien-3-yl]carbonylamino}methyl)-phenyl]methyl}-4,5-bis[2-(ethoxyethylthio)acetylamino]-pentanamide;

1-(1,2-Dipalmitoyl-sn-glycero-3-phosphoethanolamino)α,ω-dicarbonyl PEG3400-2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide;

1-(1,2-Dipalmitoyl-sn-glycero-3-phosphoethanolamino)α,ω-dicarbonyl PEG 3400-[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide conjugate;

2-[2-({5-[N-(5-(N-hydroxycarbamoyl)(5R)-5-{3-[4-(3,4-dimethoxyphenoxy)phenyl]-3 methyl-2-oxopyrrolidinyl}pentyl)carbamoyl](2-pyridyl)}amino)(1Z)-2-azavinyl]benzenesulfonic acid; and 2-(2-{[5-(N-{3-[3-(N-hydroxycarbamoyl)(4S)-4-({4-[(4-methylphenyl)methoxy]piperidyl}carbonyl)piperidyl]-3-oxopropyl}carbamoyl)(2-pyridyl)]amino}(1Z)-2-azavinyl)benzenesulfonic acid.

Still other examples of suitable imaging agents comprise an imaging moiety such as a diagnostic metal attached to a compound comprising either of the following structures:

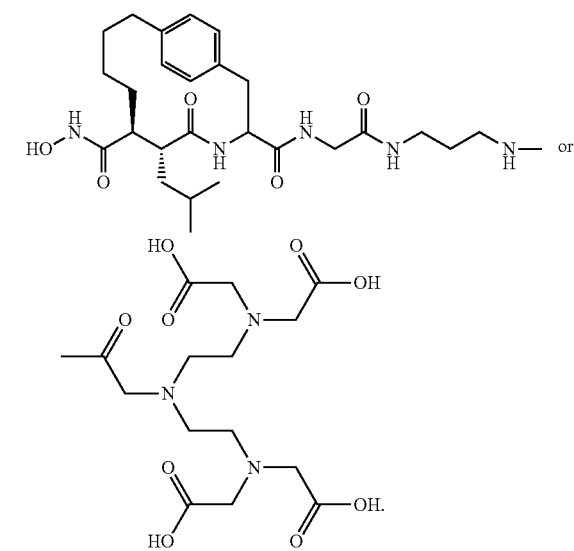

In still yet other embodiments, the imaging agent comprises the structure:

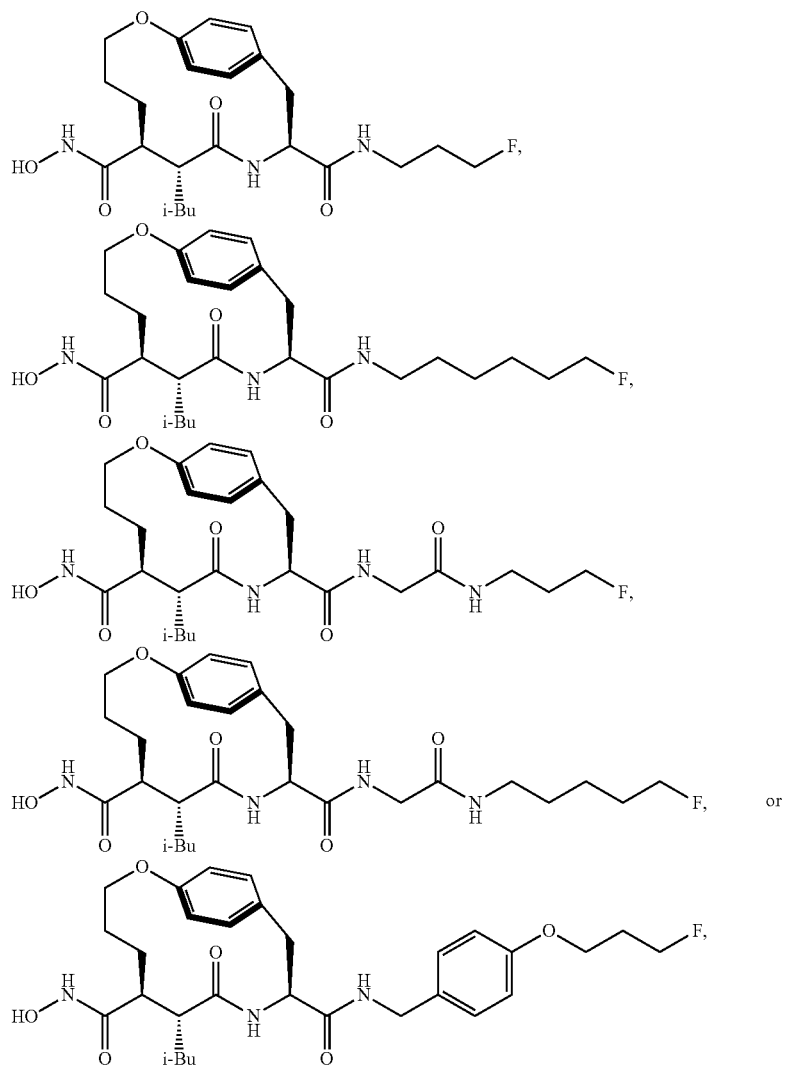

wherein F represents an isotopically-enriched population of $^{18}F$, and variants thereof comprising, instead of F, an isotopically-enriched imaging moiety selected from the group consisting of $^{11}C$, $^{13}N$, $^{123}I$, $^{125}I$, $^{99m}Tc$, $^{95}Tc$, $^{111}In$, $^{62}Cu$, $^{64}Cu$, $^{67}Ga$, and $^{68}Ga$. That is, wherein F is replaced with an isotopically-enriched imaging moiety or a chelator associated with an isotopically-enriched imaging moiety, wherein the imaging moiety is selected from the group consisting of $^{11}C$, $^{13}N$, $^{123}I$, $^{125}I$, $^{99m}Tc$, $^{95}Tc$, $^{111}In$, $^{62}Cu$, $^{64}Cu$, $^{67}Ga$, and $^{68}Ga$.

a. First Non-Limiting Set of Embodiments of Imaging Agents or Precursors Thereof This section provides non-limiting embodiments of compounds which may function as imaging agents and/or imaging agent precursors. In some embodiments, a compound is provided, wherein the compound may be associated with a radioisotope (e.g., a cytotoxic radioisotope), thereby forming an imaging agent.

(1) In some embodiments, the compound is of embodiment 1 of this first non-limiting set of embodiments, wherein the compound comprises:
a) 1-10 targeting moieties;
b) a chelator (Ch); and
c) 0-1 linking groups (Ln) between the targeting moiety and chelator;
wherein the targeting moiety is a matrix metalloproteinase inhibitor; and
wherein the chelator is capable of conjugating to a cytotoxic radioisotope.
(2) A compound according to embodiment 1, wherein the targeting moiety is a matrix metalloproteinase inhibitor having an inhibitory constant $K_1$ of <1000 nM.
(3) A compound according to embodiment 1, wherein the targeting moiety is a matrix metalloproteinase inhibitor having an inhibitory constant $K_1$ of <100 nM.
(4) A compound according to any one of embodiments 1-3, comprising 1-5 targeting moieties.
(5) A compound according to embodiment 1, comprising one targeting moiety.

(6) A compound according to any one of embodiments 1-5, wherein the targeting moiety is a matrix metalloproteinase inhibitor of the formulae (Ia) or (Ib):

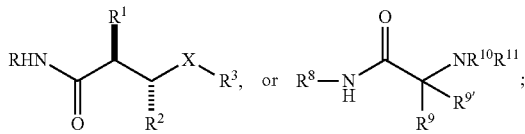

wherein,
R is independently OH or —$CH_2SH$;
$R^1$ is independently selected at each occurrence from the group: H, OH, $C_{1-3}$ alkyl, $C_{2-3}$ alkenyl, $C_{2-3}$ alkynyl, and heterocycle-S—$CH_2$—;
$R^2$ is independently $C_{1-20}$ alkyl;
X is independently C=O or $SO_2$, provided when K is C=O, $R^3$ is

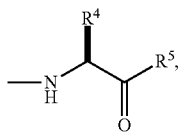

and when X is $SO_2$, $R^3$ is independently selected from the group: aryl substituted with 0-2 $R^6$, and heterocycle substituted with 0-2 $R^6$;
$R^4$ is independently selected at each occurrence from the group: $C_{1-6}$ alkyl, phenyl, and benzyl;
$R^5$ is independently at each occurrence from the group: NH($C_{1-6}$ alkyl), NH-phenyl, and NH-heterocycle; wherein said alkyl, phenyl and heterocycle groups are optionally substituted with a bond to the linking group or a bond to the chelator;
$R^6$ is independently aryloxy substituted with 0-3 $R^7$;
$R^7$ is independently halogen or methoxy;
or alternatively,
$R^1$ and $R^4$ may be taken together to form a bridging group of the formula —$(CH_2)_3$—O-phenyl-$CH_2$—, optionally substituted with a bond to the linking group or a bond to the chelator;
or alternatively,
$R^1$ and $R^2$ may be taken together to form a bridging group of the formula —$(CH_2)_3$—H—, optionally substituted with a bond to the linking group or a bond to the chelator; or
$R^1$ and $R^2$ taken together with the nitrogen and carbon atom through which they are attached form a $C_{5-7}$ atom saturated ring system substituted with one or more substituents selected from the group consisting of: a bond to Ln, a bond to Ch, and —C(=O)—$NR^{29}R^{30}$;
$R^8$ is independently at each occurrence OH or phenyl, optionally substituted with a bond to the linking group or a bond to the chelator, provided that when $R^8$ is phenyl, $R^{10}$ is —C(=O)—$CR^{12}$—NH—CH($CH_3$)—COOH;
$R^9$ and $R^{9'}$ are independently H, $C_{1-6}$ alkyl optionally substituted with a bond to the linking group or a bond to the chelator, or are taken together with the carbon atom to which $R^9$ and $R^{9'}$ are attached to form a 5-7 atom saturated, partially unsaturated or aromatic ring system containing 0-3 heteroatoms selected from O, N, $SO_2$ and S, said ring system substituted with $R^6$ and optionally substituted with a bond to the linking group or a bond to the chelator;
$R^{10}$ and $R^{11}$ are independently H, or $C_{1-6}$ alkyl optionally substituted with a bond to the linking group or a bond to the chelator, or are taken together with the nitrogen atom to which they are attached to form a 5-7 atom saturated, partially unsaturated or aromatic ring system containing 0-3 heteroatoms selected from O, N, $SO_2$ and S, said ring system optionally substituted with 0-3 $R^{27}$, a bond to the linking group or a bond to the chelator;
or alternatively,
$R^9$ and $R^{10}$ are taken together with the carbon atom to which they are attached to form a 5-7 atom saturated, partially unsaturated or aromatic ring system containing 0-3 heteroatoms selected from O, N, $SO_2$ and S, said ring system optionally substituted with a bond to the linking group or a bond to the chelator; and
$R^{12}$ is independently $C_{1-20}$ alkyl;
$R^{27}$ is =O, C1-4 alkyl, or phenyl substituted with $R^{28}$;
$R^{28}$ is a phenoxy group substituted with 0-2 $OCH_3$ groups;
$R^{29}$ and $R^{30}$ taken together with the nitrogen atom through which they are attached form a C5-7 atom saturated ring system substituted with $R^{31}$; and
$R^{31}$ is a benzyloxy group substituted with C1-4 alkyl.

(7) A compound according to any one of embodiments 1-6 wherein the targeting moiety is a matrix metalloproteinase inhibitor of the formulae (Ia) or (Ib):

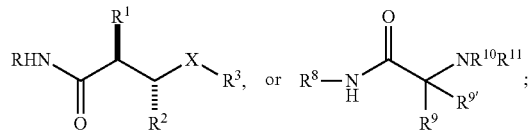

wherein,
R is OH;
$R^1$ is independently selected at each occurrence from the group: H, OH, $C_{1-3}$ alkyl, $C_{2-3}$ alkenyl, $C_{2-3}$ alkynyl, and heterocycle-S—$CH_2$—;
$R^2$ is independently $C_{1-6}$ alkyl;
X is C=O;
$R^4$ is independently selected at each occurrence from the group: $C_{1-6}$ alkyl, phenyl, and benzyl;
$R^5$ is independently at each occurrence from the group: H($C_{1-6}$ alkyl), NH-phenyl, and NH-heterocycle; wherein said alkyl, phenyl and heterocycle groups are optionally substituted with a bond to the linking group or a bond to the chelator;
$R^6$ is independently aryloxy substituted with 0-3 $R^7$;
$R^7$ is independently halogen or methoxy;
or alternatively,
$R^1$ and $R^4$ may be taken together to form a bridging group of the formula —$(CH_2)_3$—O-phenyl-$C_2$—, optionally substituted with a bond to the linking group or a bond to the chelator;
or alternatively,
$R^1$ and $R^2$ may be taken together to form a bridging group of the formula —$(CH_2)_3$—N—, optionally substituted with a bond to the linking group or a bond to the chelator; or
$R^1$ and $R^2$ taken together with the nitrogen and carbon atom through which they are attached form a $C_{5-7}$ atom saturated ring system substituted with one or more substituents selected from the group consisting of: a bond to Ln, a bond to Ch, and —C(=O)—NR$^{29}$R$^{30}$;

R$^8$ is OH:

R$^9$ and R$^{9'}$ are independently X, C$_{1-6}$ alkyl optionally substituted with a bond to the linking group or a bond to the chelator, or are taken together with the carbon atom to which R$^9$ and R$^{9'}$ are attached to form a 5-7 atom saturated, partially unsaturated or aromatic ring system containing 0-1 heteroatoms selected from O, N, said ring system optionally substituted with a bond to the linking group or a bond to the chelator;

R$^{10}$ and R$^{11}$ are independently H, or C$_{1-6}$ alkyl optionally substituted with a bond to the linking group or a bond to the chelator, or are taken together with the nitrogen atom to which they are attached to form a 5-7 atom saturated, partially unsaturated or aromatic ring system containing 0-1 heteroatoms selected from O, N, said ring system optionally substituted with 0-3 R$^{27}$, a bond to the linking group or a bond to the chelator;

or alternatively,

R$^9$ and R$^{10}$ are taken together with the carbon atom to which they are attached to form a 5-7 atom saturated, partially unsaturated or aromatic ring system containing 0-1 heteroatoms selected from O, N, said ring system optionally substituted with a bond to the linking group or a bond to the chelator; and R$^{12}$ is independently C$_{1-6}$ alkyl;

R$^{27}$ is =O, C1-4 alkyl, or phenyl substituted with R$^{28}$;

R$^{28}$ is a phenoxy group substituted with 0-2 OCH$_3$ groups;

R$^{29}$ and R$^{30}$ taken together with the nitrogen atom through which they are attached form a C5-7 atom saturated ring system substituted with R$^{31}$; and R$^{31}$ is a benzyloxy group substituted with C1-4 alkyl.

(8) A compound according to any one of embodiments 1-7 wherein:

R is —OH;

R$^2$ is C$_{1-6}$ alkyl;

X is C=O;

R$^3$ is

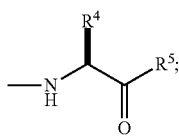

R$^1$ and R$^4$ are taken together to form a bridging group of formula —(CH$_2$)$_3$—O-phenyl-CH$_2$—;

R$^5$ is NH(C1-6alkyl), substituted with a bond to the linking group or a bond to the chelator.

A compound according to any one of embodiments 1-8, wherein:

R is —OH;

R$^9$ is C$_1$ alkyl substituted with a bond to Ln;

R$^{10}$ and R$^{11}$ taken together with the nitrogen atom to which they are attached form a 5 atom saturated ring system, said right system is substituted with 0-3 R$^{27}$;

R$^{27}$ is =O, C1-4 alkyl, or phenyl substituted with R$^{28}$; and

R$^{28}$ is a phenoxy group substituted with 0-2 OCH$_3$ groups.

(9) A compound according to any one of embodiments 1-8, wherein:

R is —OH;

R$^1$ and R$^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;

R$^{29}$ and R$^{30}$ taken together with the nitrogen atom through which they are attached form a C5-7 atom saturated ring system substituted with R$^{31}$; and R$^{31}$ is a benzyloxy group substituted with C1-4 alkyl.

(10) A compound according to any one of embodiments 1-9, wherein the linking group is of the formula:

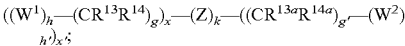

W$^1$ and W$^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$—, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0-3 R$^{16}$, C$_{3-10}$ cycloalkyl substituted with 0-3 R$^{16}$, and a 5-10 membered heterocyclic ring system containing 1-4 heteroatoms independently selected from N, B, and O and substituted with 0-3 R$^{16}$, R$^{13}$, R$^{13a}$, R$^{14}$, R$^{14a}$, and R$^{15}$ are independently selected at each occurrence from the group: H, =O, COOH, SO$_3$H, PO$_3$H, C$_1$-C$_5$ alkyl substituted with 0-3 R$^{16}$, aryl substituted with 0-3 R$^{16}$, benzyl substituted with 0-3 R$^{16}$, and C$_1$-C$_5$ alkoxy substituted with 0-3 R$^{16}$, NHC (=O)R$^{17}$, C(=O)NHR$^{17}$, NHC(=O)NHR$^{17}$, NHR$^{17}$, R$^{17}$, and a bond to the chelator;

R$^{16}$ is independently selected at each occurrence from the group: a bond to the chelator, COOR$^{17}$, C(=O)NHR$^{17}$, NHC(=O)R$^{17}$, OH, NHR$^{17}$, SO$_3$H, PO$_3$O, —OPO$_3$H$_2$, —OSO$_3$H, aryl substituted with 0-3 R$^{17}$, C$_{1-5}$ alkyl substituted with 0-1 R$^{18}$, C$_{1-5}$ alkoxy substituted with 0-1 R$^{18}$, and a 5-10 membered heterocyclic ring system containing 1-4 heteroatoms independently selected from N, S, and O and substituted with 0-3 R$^{17}$;

R$^{17}$ is independently selected at each occurrence from the group: H, alkyl substituted with 0-1 R$^{18}$, aryl substituted with 0-1 R$^{18}$, a 5-10 membered heterocyclic ring system containing 1-4 heteroatoms independently selected from N, S, and O and substituted with 0-1 R$^{18}$, C$_{3-10}$ cycloalkyl substituted with 0-1 R$^{18}$, polyalkylene glycol substituted with 0-1 R$^{18}$, carbohydrate substituted with 0-1 R$^{18}$, cyclodextrin substituted with 0-1 R$^{18}$, amino acid substituted with 0-1 R$^{18}$, polycarboxyalkyl substituted with 0-1 R$^{18}$, polyazaalkyl substituted with 0-1 R$^{18}$, peptide substituted with 0-1 R$^{18}$, wherein the peptide is comprised of 2-10 amino acids, 3,6-O-disulfo-B-D-galactopyranosyl, bis(phosphonomethyl) glycine, and a bond to the chelator;

R$^{18}$ is a bond to the chelator;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10:

t' is selected from 0, 1, 2, 3, 4, 5, 6, 7, 8, 9, and 10;

x is selected from 0, 1, 2, 3, 4, and 5; and
x' is selected from 0, 1, 2, 3, 4, and 5.

11. A compound according to any one of embodiments 6-10 wherein
$W^1$ and $W^2$ are independently selected at each occurrence from the group: O, NH, NHC(=O), C(=O)NH, $NR^{15}C$(=O), C(=O)$NR^{15}$, C(=O), C(=O)O, OC(=O), NHC(=S)NH, NHC(=O)NH, $SO_2$, —($CH_2CH_2$)$_{76\text{-}84}$—, ($OCH_2CH_2$)$_{s'}$, ($CH_2CH_2O$)$_{s''}$, ($OCH_2CH_2CH_2$)$_{s'''}$, ($CH_2CH_2CH_2O$)$_{t'}$ and (aa)$_t$;
aa is independently at each occurrence an amino acid;
Z is selected from the group: aryl substituted with 0-1 $R^{16}$, $C_{3\text{-}10}$ cycloalkyl substituted with 0-1 $R^{16}$, and a 5-10 membered heterocyclic ring system containing 1-4 heteroatoms independently selected from N, S, and O and substituted with 0-1 $R^{16}$;
$R^{13}$, $R^{13a}$, $R^{14}$, $R^{14a}$, and $R^{15}$ are independently selected at each occurrence from the group: H, =O, COOH, $SO_3H$, $C_1$-$C_5$ alkyl substituted with 0-1 $R^{16}$, aryl substituted with 0-1 $R^{16}$, benzyl substituted with 0-1 $R^{16}$, and $C_1$-$C_5$ alkoxy substituted with 0-1 $R^{16}$, NHC(=O)$R^{17}$, C(=O)$NHR^{17}$, NHC(=O)$NHR^{17}$, $NHR^{17}$, $R^{17}$, and a bond to the chelator;
k is 0 or 1;
a is selected from 0, 1, 2, 3, 4, and 5;
s' is selected from 0, 1, 2, 3, 4, and 5;
s" is selected from 0, 1, 2, 3, 4, and 5; and
t is selected from 0, 1, 2, 3, 4, and 5.

(12) A compound according to any one of embodiments 6-11, wherein:
$W^1$ is C(=O)$NR^{15}$;
h is 1;
g is 3;
$R^{13}$ and $R^{14}$ are independently H;
x is 1;
k is 0;
g' is 0;
h' is 1;
$W^2$ is NH; and
x' is 1.

(13) A compound according to any one of embodiments 6-12, wherein:
x is 0;
k is 1;
Z is aryl substituted with 0-3 $R^{16}$;
g' is 1;
$W^2$ is NH;
$R^{13a}$ and $R^{14a}$ are independently H;
h' is 1; and
x' is 1.

(14) A compound according to any one of embodiments 6-13,
wherein:
$W^1$ is C(=O)$NR^{15}$;
h is 1;
g is 2;
$R^{13}$ and $R^{14}$ are independently H;
x is 1;
k is 0;
g' is 1;
$R^{13a}$ and $R^{14a}$ are independently H; or $C_{1\text{-}5}$ alkyl substituted with 0-3 $R^{16}$;
$R^{16}$ is $SO_3H$;
$W^2$ is NHC(=O) or NH;
h' is 1; and
x' is 2.

(15) A compound according to any one of embodiments 6-14,
wherein:
$W^1$ is C(O)NH;
h is 1;
g is 3;
$R^{13}$ and $R^{14}$ are independently H;
k is 0;
g' is 0;
x is 1;
$W^2$ is —NH(C=O)— or —($OCH_2CH_2$)$_{76\text{-}84}$—;
h' is 2; and
x' is 1.

(16) A compound according to any one of embodiments 6-15,
wherein:
x is 0;
k is 0;
g' is 3;
h' is 1;
$W^2$ is NH; and
x' is 1.

(17) A compound according to any one of embodiments 6-16,
wherein:
x is 0;
Z is aryl substituted with 0-3 $R^{16}$;
k is 1;
g' is 1;
$R^{13a}R^{14a}$ are independently H;
$W^2$ is NHC(=O) or —($OCH_2CH_2$)$_{76\text{-}84}$—; and
x' is 1.

(18) A compound according to any one of embodiments 6-17,
wherein:
$W^1$ is C=O;
g is 2;
$R^{13}$ and $R^{14}$ are independently H;
k is 0;
g' is 0;
h' is 1;
$W^2$ is NH; and
x' is 1.

(19) A compound according to embodiment 1 wherein the linking group is absent.

(20) A compound according to any one of embodiments 6-19,
wherein the chelator is a metal bonding unit having a formula selected from the group:

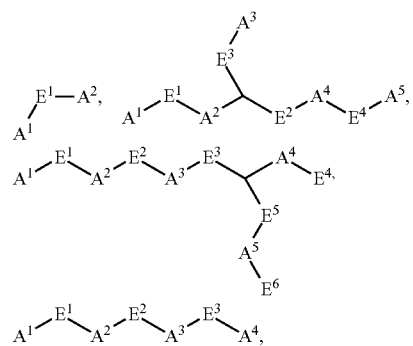

-continued

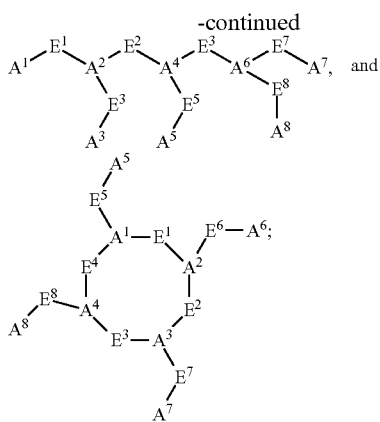

$A^1$, $A^2$, $A^3$, $A^4$, $A^5$, $A^6$, $A^7$, and $A^8$ are independently selected at each occurrence from the group: N, $NR^{26}$, $NR^{19}$, $NR^{19}R^{20}$, S, $P(O)R^{21}R^{22}$, a bond to the targeting moiety and a bond to the linking group;

Pg is a thiol protecting group;

$E^1$, $E^2$, $E^3$, $E^4$, $E^5$, $E^6$, $E^7$, and $E^8$ are independently a bond, CH, or a spacer group independently selected at each occurrence from the group: $C_1$-$C_{16}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O. $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{19}$ and $R^{20}$ are each independently selected from the group: a bond to the linking group, a bond to the targeting moiety, hydrogen, $C_1$-$C_{10}$ alkyl substituted with 0-3 $R^{23}$, aryl substituted with 0-3 $R^{23}$, $C_{1-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, a 5-10 membered heterocyclic ring system containing 1-4 heteroatoms independently selected from N, S, and O and substituted with 0-3 $R^{23}$, and an electron, provided that when one of $R^{19}$ or $R^{20}$ is an electron, then the other is also an electron;

$R^{21}$ and $R^{22}$ are each independently selected from the group: a bond to the linking group, a bond to the targeting moiety, —OH, $C_1$-$C_{10}$ alkyl substituted with 0-3 $R^{23}$, $C_1$-$C_{10}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{23}$ is independently selected at each occurrence from the group: a bond to the linking group, a bond to the targeting moiety, =O, F, Cl, Br, I, —$CF_3$, —CH, —$CO_2R^{24}$, —C(=O)$R^{24}$, —C(=O)N($R^{24})_2$, —CHO, —$CH_2OR^{24}$, —OC(=O)$R^{24}$, —OC(=O)$OR^{24a}$, —$OR^{24}$, —OC(=O)N($R^{24})_2$, —$NR^{25}$C(=O)$R^{24}$, —$NR^{25}$C(=O)$OR^{24a}$, —$NR^{25}$C(=O)N($R^{24})_2$, —$NR^{25}SO_2N(R^{24})_2$, —$NR^{25}SO_2R^{24a}$, —$SO_3H$, —$SO_2R^{24a}$, —$SR^{24}$, —S(=O)$R^{24a}$, —$SO_2N(R^{24})_2$, —N($R^{24})_2$, —NHC(=S)$NHR^{24}$, =$NOR^{24}$, $NO_2$, —C(=O)$NHOR^{24}$, —C(=O)$NHNR^{24}R^{24a}$, —$OCH_2CO_2H$, 2-(1-morpholino)ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 $R^{24}$, and a 5-10 membered heterocyclic ring system containing 1-4 heteroatoms independently selected from N, S, and O; and wherein at least one of $A^1$, $A^2$, $A^3$, $A^4$, $A^5$, $A^6$, $A^7$, $A^8$ or $R^{23}$ is a bond to the linking group or targeting moiety;

$R^{24}$, $R^{24a}$, and $R^{25}$ are independently selected at each occurrence from the group: a bond to the linking group, a bond to the targeting moiety, H, $C_1$-$C_6$ alkyl, phenyl, benzyl, $C_1$-$C_6$ alkoxy, halide, nitro, cyano, and trifluoromethyl; and $R^{26}$ is a co-ordinate bond to a metal or a hydrazine protecting group.

(21) A compound according to any one of embodiments 6-20 wherein:

$A^1$, $A^2$, $A^3$, $A^4$, $A^5$, $A^6$, $A^7$, and $A^8$ are independently selected at each occurrence from the group: $NR^{19}$, $NR^{19}R^{20}$, S, SH, OH, a bond to the targeting moiety and a bond to the linking group;

$E^1$, $R^2$, $E^3$, $E^4$, $E^5$, $E^6$, $E^7$, and $E^8$ are independently a bond, CH, or a spacer group independently selected at each occurrence from the group: $C_1$-$C_{10}$ alkyl substituted with 0-3 $R^{23}$, aryl substituted with 0-3 $R^{23}$, $C_{3-10}$ cycloalkyl substituted with 0-3 $R^{23}$, and a 5-10 membered heterocyclic ring system containing 1-4 heteroatoms independently selected from N, S, and O and substituted with 0-3 $R^{23}$;

wherein at least one of $A^1$, $A^2$, $A^3$, $A^4$, $A^5$, $A^6$, $A^7$, $A^8$ and $R^{23}$ is a bond to the linking group or a targeting moiety;

$R^{19}$, and $R^{20}$ are each independently selected from the group: a bond to the targeting moiety, a bond to the linking group, hydrogen, $C_1$-$C_{10}$ alkyl substituted with 0-3 $R^{23}$, aryl substituted with 0-3 $R^{23}$, a 5-10 membered heterocyclic ring system containing 1-4 heteroatoms independently selected from N, S, and O and substituted with 0-3 $R^{23}$, and an electron, provided that when one of $R^{19}$ or $R^{20}$ is an electron, then the other is also an electron;

$R^{23}$ is independently selected at each occurrence from the group: a bond to the targeting moiety, a bond to the linking group, =O, F, Cl, Br, I, —$CF_3$, —CN, —$CO_2R^{24}$, —C(=O)$R^{24}$, —C(=O)N($R^{24})_2$, —$CH_2OR^{24}$, —OC(=O)$R^{24}$, —OC(=O)$OR^{24a}$, —$OR^{24}$, —OC(=O)N($R^{24})_2$, —$NR^{25}$C(=O)$R^{24}$, —$NR^{25}$C(=O)$OR^{24a}$, —$NR^{25}$C(=O)N($R^{24})_2$, —$NR^{25}SO_2N(R^{24})_2$, —$NR^{25}SO_2R^{24a}$, —$SO_3H$, —$SO_2R^{24a}$, —S(=O)$R^{24a}$, —$SO_2N(R^{24})_2$, —N($R^{24})_2$, —NHC(=S)$NHR^{24}$, =$NOR^{18}$, —C(=O)$NHNR^{18}R^{18a}$, —$OCH_2CO_2H$, and 2-(1-morpholino)ethoxy; and $R^{24}$, $R^{24a}$, and $R^{25}$ are independently selected at each occurrence from the group: a bond to the linking group, H, and $C_1$-$C_6$ alkyl.

(22) A compound according to any one of embodiments 6-21 wherein the chelator is of the formula:

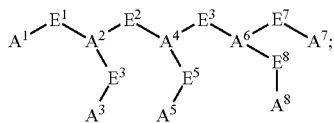

$A^1$ is a bond to the linking group;
$A^2$, $A^4$, and $A^6$ are each N;
$A^3$, $A^5$, $A^7$ and $A^8$ are each OH;
$E^1$, $E^2$, and $E^4$ are $C_2$ alkyl;
$E^3$, $E^5$, $E^7$, and $E^8$ are $C_2$ alkyl substituted with 0-1 $R^{23}$;
$R^{23}$ is =O;
(23) A compound according to any one of embodiments 6-22 wherein
the chelator is of the formula:
$C_h$ is

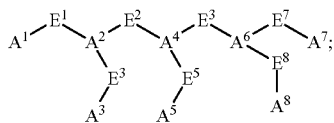

wherein:
$A^5$ is a bond to Ln;
$A^1$, $A^3$, $A^7$ and $A^8$ are each OH;
$A^2$, $A^4$ and $A^6$ are each NH;
$E^1$, $E^3$, $E^5$, $E^7$, and $R^8$ are $C_2$ alkyl substituted with 0-1 $R^{23}$;
$E^2$, and $E^4$, are $C_2$ alkyl;
$R^{23}$ is =O.
(24) A compound according to any one of embodiments 6-23 wherein the chelator is of the formula:

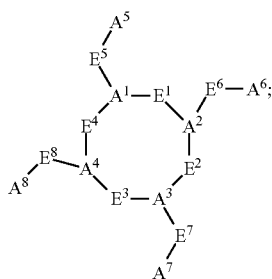

$A^1$, $A^2$, $A^3$ and $A^4$ are each N;
$A^5$, $A^6$ and $A^8$ are each OR;
$A^7$ is a bond to $L_n$;
$E^1$, $E^2$, $E^3$, $E^4$ are each independently $C_2$ alkyl; and
$E^5$, $E^6$, $E^7$, $E^8$ are each independently $C_2$ alkyl substituted with 0-1 $R^{23}$;
$R^{23}$ is =O.
(25) A compound according to any one of embodiments 6-24 wherein
the chelator is of the formula:

$A^1$ is $NR^{26}$;
$R^{26}$ is a co-ordinate bond to a metal or a hydrazine protecting group;

$E^1$ is a bond;
$A^2$ is $NHR^{19}$;
$R^{19}$ is a heterocycle substituted with $R^{23}$, the heterocycle being selected from pyridine and pyrimidine;
$R^{23}$ is selected from a bond to the linking group, C(=O)NHR$^{24}$ and C(=O)R$^{24}$; and
$R^{24}$ is a bond to the linking group.
(26) A compound according to any one of embodiments 6-25 wherein
the chelator is of the formula:

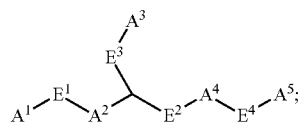

wherein:
$A^1$ and $A^5$ are each —S(Pg);
Pg is a thiol protecting group;
$E^1$ and $E^4$ are $C_2$ alkyl substituted with 0-1 $R^{25}$;
$R^{23}$ is =O;
$A^2$ and $A^4$ are each —NH;
$E^2$ is $CH_2$;
$E^3$ is $C_{1-3}$ alkyl substituted with 0-1$R^{23}$;
$A^3$ is a bond to La.
(27) A compound according to any one of embodiments 6-26 wherein
the chelator is of the formula:

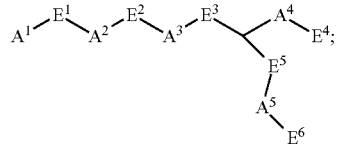

wherein:
$A^1$ is a bond to Ln;
$E^1$ is $C_1$ alkyl substituted by $R^{23}$;
$A^2$ is NH;
$E^2$ is $C_2$ alkyl substituted with 0-1$R^{23}$;
$A^3$ is —O—P(O)($R^{21}$)—O;
$E^3$ is $C_1$ alkyl;
$A^4$ and $A^5$ are each —O—;
$E^4$ and $E^6$ are each independently $C_{1-16}$ alkyl substituted with 0-1$R^{23}$;
$E^5$ is $C_1$ alkyl;
$R^{21}$ is —OH; and
$R^{23}$ is =O.
(28) A compound of embodiment 1 having the formula:

wherein, Q is a compound of Formulae (Ia) or (Ib):

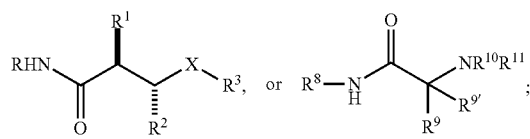

wherein,
R is independently OH or —CH$_2$SH;

R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;

R$^2$ is independently C$_{1-20}$ alkyl;

X is independently C=O or SO$_2$, provided when X is C=O, R$^3$ is

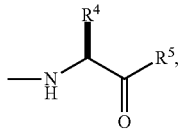

and when X is SO$_2$, R$^3$ is independently selected from the group: aryl substituted with 0-2 R$^6$, and heterocycle substituted with 0-2 R$^6$;

R$^4$ is independently selected at each occurrence from the group: C$_{1-6}$ alkyl, phenyl, and benzyl;

R$^5$ is independently at each occurrence from the group: NH(C$_{1-6}$ alkyl), NH-phenyl, and NH-heterocycle; wherein said alkyl, phenyl and heterocycle groups are optionally substituted with a bond to L$_n$;

R$^6$ is independently aryloxy substituted with 0-3 R$^7$;

R$^7$ is independently halogen or methoxy;

or alternatively,

R$^1$ and R$^4$ may be taken together to form a bridging group of the formula —(CH$_2$)$_3$—O-phenyl-CH$_2$—, optionally substituted with a bond to L$_n$;

or alternatively,

R$^1$ and R$^2$ may be taken together to form a bridging group of the formula —(CH$_2$)$_3$—NH—, optionally substituted with a bond to L$_n$; or R$^1$ and R$^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;

R$^8$ is independently at each occurrence OH or phenyl, optionally substituted with a bond to L$_n$, provided that when R$^8$ is phenyl, R$^{10}$ is —C(=O)—CR$^{12}$—NH—CH(CH$_3$)—COOH;

R$^9$ and R$^{9'}$ are independently H, C$_{1-6}$ alkyl optionally substituted with a bond to L$_n$, or are taken together with the carbon atom to which they are attached to form a 5-7 atom saturated, partially unsaturated or aromatic ring system containing 0-3 heteroatoms selected from O, N, SO$_2$ and S, said ring system substituted with R$^6$ and optionally substituted with a bond to L$_n$;

R$^{10}$ and R$^{11}$ are independently H, or C$_{1-6}$ alkyl optionally substituted with a bond to L$_n$, or are taken together with the nitrogen atom to which they are attached to form a 5-7 atom saturated, partially unsaturated or aromatic ring system containing 0-3 heteroatoms selected from O, N, SO$_2$ and S, said ring system optionally substituted with 0-3 R$^{27}$ or a bond to W;

or alternatively,

R$^9$ and R$^{10}$ are taken together with the carbon atom to which they are attached to form a 5-7 atom saturated, partially unsaturated or aromatic ring system containing 0-3 heteroatoms selected from O, N, SO$_2$ and S, said ring system optionally substituted with a bond to L$_n$;

R$^{12}$ is independently C$_{1-20}$ alkyl;

d is selected from 1, 2, 3, 4, 5, 6, 7, 8, 9, and 10;

L$_n$ is a linking group having the formula:

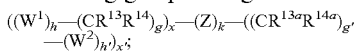

W$^1$ and W$^2$ are independently selected at each occurrence from the group: O, S, NH, NHC(O), C(=O)NH, NR$^{15}$C(=O), C(=O)NR$^{15}$, C(=O), C(=O)O, OC(=O), NHC(=S) NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0-3 R$^{16}$, C$_{3-10}$ cycloalkyl substituted with 0-3 R$^{16}$, and a 5-10 membered heterocyclic ring system containing 1-4 heteroatoms independently selected from N, S, and O and substituted with 0-3 R$^{16}$;

R$^{13}$, R$^{13a}$, R$^{14}$, R$^{14a}$, and R$^{15}$ are independently selected at each occurrence from the group: H, =O, COOH, SO$_3$H, PO$_3$O, C$_1$-C$_5$ alkyl substituted with 0-3 R$^{16}$, aryl substituted with 0-3 R$^{16}$, benzyl substituted with 0-3 R$^{16}$, and C$_1$-C$_5$ alkoxy substituted with 0-3 R$^{16}$, NHC(=O)R$^{17}$, C(=O)NHR$^{17}$, NHC(=O)NHR$^{17}$, NHR$^{17}$, R$^{17}$, and a bond to C$_h$;

R$^{16}$ is independently selected at each occurrence from the group: a bond to C$_h$, COOR$^{17}$, C(=O)NHR$^{17}$, NHC(=O)R$^{17}$, OH, NHR$^{17}$, SO$_3$H, PO$_3$H, —OPO$_3$H$_2$, —OSO$_3$H, aryl substituted with 0-3 R$^{17}$, C$_{1-5}$ alkyl substituted with 0-1 R$^{18}$, C$_{1-5}$ alkoxy substituted with 0-1 R$^{18}$, and a 5-10 membered heterocyclic ring system containing 1-4 heteroatoms independently selected from N, S, and O and substituted with 0-3 R$^{17}$;

R$^{17}$ is independently selected at each occurrence from the group: H, alkyl substituted with 0-1 R$^{18}$, aryl substituted with 0-1 R$^{18}$, a 5-10 membered heterocyclic ring system containing 1-4 heteroatoms independently selected from N, S, and O and substituted with 0-1 RIB, C$_{3-10}$ cycloalkyl substituted with 0-1 R$^{18}$, polyalkylene glycol substituted with 0-1 R$^{18}$, carbohydrate substituted with 0-1 R$^{18}$, cyclodextrin substituted with 0-1 R$^{18}$, amino acid substituted with 0-1 R$^{18}$, polycarboxyalkyl substituted with 0-1 R$^{18}$, polyazaalkyl substituted with 0-1 R$^{18}$, peptide substituted with 0-1 R$^{18}$, wherein the peptide is comprised of 2-10 amino acids, 3,6-O-disulfo-B-D-galactopyranosyl, bis(phosphonomethyl) glycine, and a bond to C$_h$;

R$^{18}$ is a bond to C$_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

C$_h$ is a metal bonding unit having a formula selected from the group:

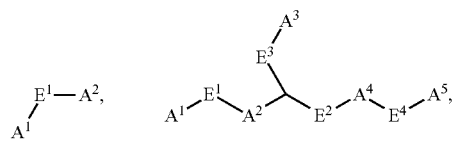

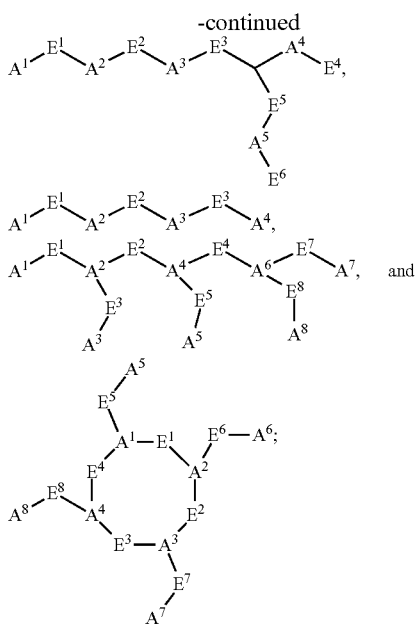

$A^1$, $A^2$, $A^3$, $A^4$, $A^5$, $A^6$, $A^7$, and $A^8$ are independently selected at each occurrence from the group: N, $NR^{26}$, $NR^{19}$, $NR^{19}R^{20}$, S, SR, —S(Pg), O, ON, $PR^{19}$, $PR^{19}R^{20}$, —O—P(O)($R^{21}$)—O—, P(O)$R^{21}R^{22}$, a bond to the targeting moiety and a bond to the linking group;

Pg is a thiol protecting group;

$E^1$, $E^2$, $E^3$, $E^4$, $E^5$, $E^6$, $E^7$, and $E^8$ are independently a bond, CH, or a spacer group independently selected at each occurrence from the group: $C_1$-$C_{16}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{19}$ and $R^{20}$ are each independently selected from the group: a bond to the linking group, a bond to the targeting moiety, hydrogen, $C_1$-$C_{10}$ alkyl substituted with 0-3 $R^{23}$, aryl substituted with 0-3 $R^{23}$, $C_{1-10}$ cycloalkyl substituted with 0-3 $R^{23}$, heterocyclo-$C_{1-20}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, a 5-10 membered heterocyclic ring system containing 1-4 heteroatoms independently selected from N, S, and O and substituted with 0-3 $R^{23}$, and an electron, provided that when one of $R^{19}$ or $R^{20}$ is an electron, then the other is also an electron;

$R^{21}$ and $R^{22}$ are each independently selected from the group: a bond to the linking group, a bond to the targeting moiety, —OH, $C_1$-$C_{10}$ alkyl substituted with 0-3 $R^{23}$, $C_1$-$C_{10}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{23}$ is independently selected at each occurrence from the group: a bond to the linking group, a bond to the targeting moiety, =O, F, Cl, Br, I, —$CF_3$, —CN, —$CO_2R^{24}$, —C(=O)$R^{24}$, —C(=O)N($R^{24}$)$_2$, —CHO, —$CH_2OR^{24}$, —OC(=O)$R^{24}$, —OC(=O)O$R^{24a}$, —$OR^{24}$, —OC(=O)N($R^{24}$)$_2$, —$NR^{25}$C(=O)$R^{24}$, —$NR^{25}$C(=O)O$R^{24a}$, —$NR^{25}$C(=O)N($R^{24}$)$_2$, —$NR^{25}SO_2$N($R^{24}$)$_2$, —$NR^{25}SO_2R^{24a}$, —$SO_3H$, —$SO_2R^{24a}$, —$SR^{24}$, —S(=O)$R^{24a}$, —$SO_2$N($R^{24}$)$_2$, —N($R^{24}$)$_2$, —NHC(=S)$NHR^{24}$, =$NOR^{24}$, $NO_2$, —C(=O)$NHOR^{24}$, —C(=O)$NHR^{24}R^{24a}$, —$OCH_2CO_2H$, 2-(1-morpholino)ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 $R^{24}$, and a 5-10 membered heterocyclic ring system containing 1-4 heteroatoms independently selected from N, S, and O; and wherein at least one of $A^1$, $A^2$, $A^3$, $A^4$, $A^5$, $A^6$, $A^7$, $A^8$ or $R^{23}$ is a bond to the linking group or targeting moiety;

$R^{24}$, $R^{24a}$, and $R^{25}$ are independently selected at each occurrence from the group: a bond to the linking group, a bond to the targeting moiety, H, $C_1$-$C_6$ alkyl, phenyl, benzyl, $C_1$-$C_6$ alkoxy, halide, nitro, cyano, and trifluoromethyl; and $R^{26}$ is a co-ordinate bond to a metal or a hydrazine protecting group; or a pharmaceutically acceptable salt thereof.

(29) A compound according to embodiment 28 wherein:

R is —OH;

$R^2$ is C1-6 alkyl;

X is C=O;

$R^3$ is

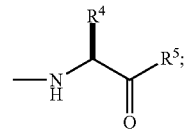

$R^1$ and $R^4$ are taken together to form a bridging group of formula —($CH_2$)$_3$—O-phenyl-$CH_2$—;

$R^5$ is NH(C1-6alkyl), substituted with a bond to the linking group or a bond to the chelator.

(30) A compound according to any one of embodiments 28-29 wherein:

R is —OH;

$R^9$ is $C_1$ alkyl substituted with a bond to Ln;

$R^{10}$ and $R^{11}$ taken together with the nitrogen atom to which they are attached form a 5 atom saturated ring system, said right system is substituted with 0-3 $R^{27}$;

$R^{27}$ is =O, C1-4 alkyl, or phenyl substituted with $R^{28}$; and $R^{28}$ is a phenoxy group substituted with 0-2 $OCH_3$ groups.

(31) A compound according to any one of embodiments 28-30 wherein

R is —OH;

$R^1$ and $R^2$ taken together with the nitrogen and carbon atom through which they are attached form a $C_{5-7}$ atom saturated ring system substituted with one or more substituents selected from the group consisting of: a bond to Ln, a bond to Ch, and —C(═O)—NR$^{29}$R$^{30}$;

$R^{29}$ and $R^{30}$ taken together with the nitrogen atom through which they are attached form a C5-7 atom saturated ring system substituted with $R^{31}$; and $R^{31}$ is a benzyloxy group substituted with C1-4 alkyl.

(32) A compound according to any one of embodiments 28-31
wherein
d is selected from 1, 2, 3, 4, and 5;
W is independently selected at each occurrence from the group: O, NH, NHC(═O), C(═O)NH, NR$^{15}$C(═O), C(═O)NR$^{15}$, C(═O), C(═O)O, OC(═O), NHC(═S)NH, NHC(═O)NH, SO$_2$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_t$;
aa is independently at each occurrence an amino acid;
Z is selected from the group: aryl substituted with 0-1 $R^{16}$, $C_{3-10}$ cycloalkyl substituted with 0-1 $R^{16}$, and a 5-10 membered heterocyclic ring system containing 1-4 heteroatoms independently selected from N, S, and O and substituted with 0-1 $R^{16}$;
$R^{13}$, $R^{13a}$, $R^{14}$, $R^{14a}$, and $R^{15}$ are independently selected at each occurrence from the group: H, ═O, COOH, SO$_3$H, $C_1$-$C_5$ alkyl substituted with 0-1 $R^{16}$, aryl substituted with 0-1 $R^{16}$, benzyl substituted with 0-1 $R^{16}$, and $C_1$-$C_5$ alkoxy substituted with 0-1 $R^{16}$, NHC(═O)$R^{17}$, C(═O)NHR$^{17}$, NHC(═O)NHR$^{17}$, NHR$^{17}$, $R^{17}$, and a bond to $C_h$;
k is 0 or 1;
s is selected from 0, 1, 2, 3, 4, and 5;
s' is selected from 0, 1, 2, 3, 4, and 5;
s" is selected from 0, 1, 2, 3, 4, and 5;
t is selected from 0, 1, 2, 3, 4, and 5;
$A^1$, $A^2$, $A^3$, $A^4$, $A^5$, $A^6$, $A^7$, and $A^8$ are independently selected at each occurrence from the group: NR$^{19}$, NR$^{19}$R$^{20}$, S, SH, OH, and a bond to L$_n$;
E is a bond, CH, or a spacer group independently selected at each occurrence from the group: $C_1$-$C_{10}$ alkyl substituted with 0-3 $R^{23}$, aryl substituted with 0-3 $R^{23}$, $C_{3-10}$ cycloalkyl substituted with 0-3 $R^{23}$, and a 5-10 membered heterocyclic ring system containing 1-4 heteroatoms independently selected from N, S, and O and substituted with 0-3 $R^{23}$;
$R^{19}$, and $R^{20}$ are each independently selected from the group: a bond to L$_n$, hydrogen, $C_1$-$C_{10}$ alkyl substituted with 0-3 $R^{23}$, aryl substituted with 0-3 $R^{23}$, a 5-10 membered heterocyclic ring system containing 1-4 heteroatoms independently selected from N, S, and O and substituted with 0-3 $R^{23}$, and an electron, provided that when one of $R^{19}$ or $R^{20}$ is an electron, then the other is also an electron;
$R^{23}$ is independently selected at each occurrence from the group: a bond to L$_n$, ═O, F, Cl, Br, I, —CF$_3$, —CN, —CO$_2$R$^{24}$, —C(═O)R$^{24}$, —C(═O)N(R$^{24}$)$_2$, —CH$_2$OR$^{24}$, —OC(═O)R$^{24}$, —OC(═O)OR$^{24a}$, —OR$^{24}$, —OC(═O)N(R$^{24}$)$_2$, —NR$^{25}$C(═O)R$^{24}$, —NR$^{25}$C(═O)OR$^{24a}$, —NR$^{25}$C(═O)N(R$^{24}$)$_2$, —NR$^{25}$SO$_2$N(R$^{24}$)$_2$, —NR$^{25}$SO$_2$R$^{24a}$, —SO$_3$H, —SO$_2$R$^{24a}$, —S(═O)R$^{24a}$, —SO$_2$N(R$^{24}$)$_2$, —N(R$^{23}$)$_2$, —NHC(═S)NHR$^{24}$, ═NOR$^{18}$, —C(═O) NHNR$^{18}$R$^{18a}$, —OCH$_2$CO$_2$H, and 2-(1-morpholino) ethoxy; and $R^{24}$, $R^{24a}$, and $R^{25}$ are independently selected at each occurrence from the group: a bond to L$_n$, H, and $C_1$-$C_6$ alkyl; and

(33) A compound according to any one of embodiments 28-32
wherein
d is 1,
$C_h$ is

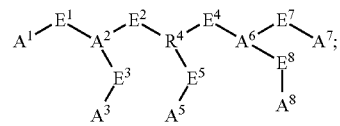

$A^1$ is a bond to L$_n$;
$A^2$, $A^4$, and $A^6$ are each N
$A^3$, $A^5$, $A^7$ and $A^8$ are each OH;
$E^1$, $E^2$, and $E^4$ are C2 alkyl;
$E^3$, $E^5$, $E^7$, and $E^8$ are $C_2$ alkyl substituted with 0-1 $R^{23}$;
$R^{23}$ is ═O;

(34) A compound according to any one of embodiments 28-33
wherein
$C_h$ is

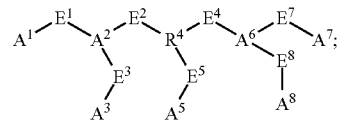

wherein:
A5 is a bond to Ln;
$A^1$, $A^3$, $A^7$ and $A^8$ are each OH;
$A^2$, $A^4$ and $A^6$ are each NH;
$E^1$, $E^3$, $E^5$, $E^7$, and $E^8$ are $C_2$ alkyl substituted with 0-1 $R^{23}$;
$E^2$, and $E^4$, are $C_2$ alkyl;
$R^{23}$ is ═O.

(35) A compound according to any one of embodiments 28-34 is
wherein
$C_h$ is

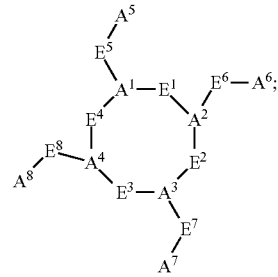

$A^1$, $A^2$, $A^3$ and $A^4$ are each N;
$A^5$, $A^6$ and $A^8$ are each OH;
$A^7$ is a bond to L$_n$;
$E^1$, $E^2$, $E^3$, $E^4$ are each independently, $C_2$ alkyl; and
$E^5$, $E^6$, $E^7$, $E^8$ are each independently, $C_2$ alkyl substituted with 0-1 $R^{23}$;
$R^{23}$ is ═O;

(36) A compound according to any one of embodiments 28-35
wherein
$C_h$ is

$A^1$ is $NR^{26}$;
$R^{26}$ is a co-ordinate bond to a metal; or a hydrazine protecting group;
$E^1$ is a bond;
$A^2$ is $NHR^{19}$;
$R^{19}$ is a heterocycle substituted with $R^{23}$, the heterocycle being selected from pyridine and pyrimidine;
$R^{23}$ is selected from a bond to $L_n$, $C(=O)NHR^{24}$ and $C(=O)R^{24}$; and
$R^{24}$ is a bond to $L_n$.

(37) A compound according to any one of embodiments 28-36
wherein

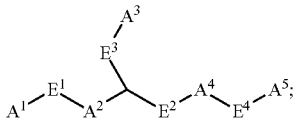

wherein:
$A^1$ and $A^5$ are each —S(Pg);
Pg is a thiol protecting group;
$E^1$ and $E^5$ are $C_2$ alkyl substituted with 0-1 $R^{23}$;
$R^{23}$ is =O;
$A^2$ and $A^4$ are each —NH;
$E^1$ is $CH_2$;
$E^3$ is C1-3 alkyl substituted with 0-1 $R^{23}$;
$A^3$ is a bond to Ln.

(38) A compound according to any one of embodiments 28-37
wherein

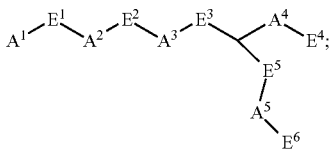

wherein.
$A^1$ is a bond to Ln;
$E^1$ is $C_1$ alkyl substituted by $R^{23}$;
$A^2$ is NH;
$E^2$ is $C_2$ alkyl substituted with 0-1$R^{23}$;
$A^3$ is —O—P(O)($R^{21}$)—O;
$E^3$ is $C_1$ alkyl;
$A^4$ and $A^5$ are each —O—;
$E^4$ and $E^6$ are each independently $C_{1-16}$ alkyl substituted with 0-1$R^{23}$;
$E^5$ is C, alkyl;
$A^5$ is —O—;
$R^{21}$ is —OH; and
$R^{23}$ is =O.

(39) A compound according embodiment 28 wherein
$W^1$ is $C(=O)NR^{15}$;
h is 1;
g is 3;
$R^{13}$ and $R^{14}$ are independently R;
x is 1;
k is 0;
g' is 0;
h' is 1;
$W^2$ is NH; and
x' is 1.

(40) A compound according to embodiments 28 wherein
x is 0;
k is 1;
Z is aryl substituted with 0-3 $R^{16}$;
g' is 1;
$W^2$ is NH;
$R^{13a}$ and $R^{14a}$ are independently H;
h' is 1; and
x' is 1.

(41) A compound according to embodiments 28 wherein
$W^1$ is $C(=O)NR^{15}$;
h is 1;
g is 2;
$R^{13}$ and $R^{14}$ are independently H;
x is 1;
k is 0
g' is 1;
$R^{13a}$ and $R^{14a}$ are independently H; or C1-5 alkyl substituted with 0-3 $R^{16}$;
$R^{16}$ is $SO_3H$;
$W^2$ is NHC(=O) or NH;
h' is 1; and
x' is 2.

(42) A compound according to embodiment 28 wherein
$W^1$ is C(=O)NH;
h is 1;
g is 3;
$R^{13}$ and $R^{14}$ are independently H;
k is 0;
g' is 0;
x is 1;
$W^2$ is —NH(C=O)— or —(OCH$_2$CH$_2$)$_{76-84}$—;
h' is 2; and
x' is 1.

(43) A compound according to embodiment 28 wherein
x is 0;
k is 0;
g' is 3;
h' is 1;
$W^2$ is NH; and
x' is 1.

(44) A compound according to embodiment 28 wherein
x is 0;
Z is aryl substituted with 0-3 $R^{16}$;
k is 1;
g' is 1;
$R^{13a}R^{14a}$ are independently H;
$W^2$ is NHC(=O) or —(OCH$_2$CH$_2$)$_{76-84}$—; and
x' is 1.

(45) A compound according to embodiment 28 wherein
$W^1$ is C=O;
g is 2;
$R^{13}$ and $R^{14}$ are independently H;
k is 0;
g' is 0;
h' is 1;
$W^2$ is NH; and
x' is 1.

(46) A compound according to embodiment 1 or 28 selected from the group consisting of:

2-{[5-(3-(2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino)-propylcarbamoyl)-pyridin-2-yl]-hydrazonomethyl}-benzenesulfonic acid;

2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid;

2-[7-({N-[3-(2-([7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino)acetylamino)propyl]carbamoyl}methyl)-1,4,7,10-tetraaza-4,10-bis(carboxymethyl)cyclododecyl]acetic acid;

2-(7-[(N-([4-(([7-(N-hydroxycarbamoyl)(3S,6R,7S)-4-aza-6-(2-methylpropyl)-11-oxa-5-oxobicyclo(10.2.2)hexadeca-1(15),12(16),13-trien-3-yl]-carbonylamino)methyl)phenyl]methyl)carbamoyl)methyl]-1,4,7,10-tetraaza-4,10-bis(carboxymethyl)cyclododecyl)acetic acid;

2-(7-{[N-(1-(N-[3-(2-([7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl] carbonylamino}acetylamino)propyl]carbamoyl)-2-sulfoethyl)carbamoyl]methyl}-1,4,7,10-tetraaza-4,10-bis(carboxymethyl)cyclododecyl)acetic acid;

2-[7-({N-[1-(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid;

2-({2-[({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}methyl)(carboxyethyl)amino}ethyl){2-[bis(carboxymethyl)amino]ethyl}amino)acetic acid;

2-[(2-{[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl](carboxymethyl)amino}ethyl){2-[bis(carboxymethyl)amino]ethyl}amino]acetic acid;

N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-4,5-bis[2-(ethoxyethylthio)acetylamino]pentanamide;

N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}methyl)-phenyl]methyl}-4,5-bis[2-(ethoxyethylthio)acetylamino]-pentanamide;

1-(1,2-Dipalmitoyl-sn-glycero-3-phosphoethanolamino)-α,ω-dicarbonylPEG$_{3400}$-2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide;

1-(1,2-Dipalmitoyl-sn-glycero-3-phosphoethanolamino)-α,ω-dicarbonylPEG$_{3400}$-[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide conjugate;

2-[2-({5-[N-(5-(N-hydroxycarbamoyl)(5R)-5-{3-[4-(3,4-dimethoxyphenoxy)phenyl]-3-methyl-2-oxopyrrolidinyl}pentyl)carbamoyl](2-pyridyl)}amino)(1Z)-2-azavinyl]benzenesulfonic acid;

2-(2-{[5-(N-{3-[3-(N-hydroxycarbamoyl)(4S)-4-({4-[(4-methylphenyl)methoxy]piperidyl}carbonyl)piperidyl]-3-oxopropyl}carbamoyl)(2-pyridyl)]amino}(1Z)-2-azavinyl)benzenesulfonic acid; and

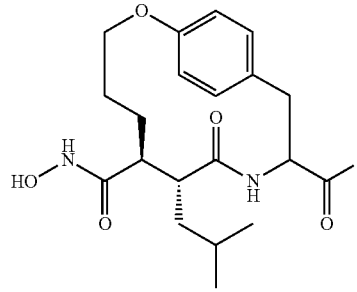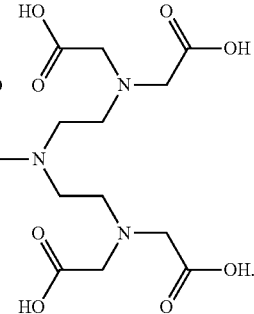

(47) In some embodiments, a radiopharmaceutical comprising a compound of any one of embodiments 1-46 and a cytotoxic radioisotope which is complexed to the chelator.

(48) In some embodiments, a radiopharmaceutical comprising a compound of any one of embodiments 1-47 and a cytotoxic radioisotope which is complexed to the chelator.

(49) In some embodiments, a radiopharmaceutical comprising a compound of any one of embodiments 1-47 and a cytotoxic radioisotope.

(50) In some embodiments, a radiopharmaceutical according to embodiment 20 selected from the group consisting of: 2-{[5-(3-{2-[(6-Hydroxycarbamoyl-7-isobutyl-8-oxo-2-oxa-9-aza-bicyclo[10.-2.2]hexadeca-1(15),12(16),13-triene-10-carbonyl)-amino]-acetylamino}-propy-lcarbamoyl)-pyridin-2-yl]-hydrazonomethyl}-benzenesulfonic acid; and 2-{[5-(4-{[(6-Hydroxycarbamoyl-7-isobutyl-8-oxo-2-oxa-9-aza-bicyclo[10.2.-2]hexadeca-1(15),12(16),13-triene-10-carbonyl)-amino]-methyl}-benzylcarbam-oyl)-pyridin-2-yl]-hydrazonomethyl}-benzenesulfonic acid; wherein the cytotoxic radioisotope is $^{99m}$Tc.

(51) In some embodiments, a radiopharmaceutical according to embodiment 47 wherein the cytotoxic radioisotope is selected from the group consisting of beta particle emitters, alpha particle emitters, and Auger electron emitters.

(52) In some embodiments, a radiopharmaceutical according to embodiment 47 wherein the cytotoxic radioisotope is selected from the group consisting of: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir.

(53) In some embodiments, a radiopharmaceutical according to embodiment 47 wherein the cytotoxic radioisotope is selected from the group consisting of: $^{186}$Re, $^{188}$Re, $^{153}$Sm, $^{166}$Ho, $^{177}$Lu, $^{149}$Pm, $^{90}$Y, $^{212}$Bi, $^{103}$Pd, and $^{105}$Rh.

(54) In some embodiments, a radiopharmaceutical according to embodiment 47 wherein the cytotoxic radioisotope is selected from the group consisting of: $^{186}$Re, $^{188}$Re, $^{153}$Sm, $^{166}$Ho, $^{177}$Lu, $^{149}$Pm, $^{90}$Y, and $^{212}$Bi.

(55) In some embodiments, a composition comprising a compound of any one of embodiments 1-54, or a pharmaceutically acceptable salt thereof, and a pharmaceutically acceptable carrier.

b. Second Non-Limiting Set of Embodiments of Imaging Agents or Precursors Thereof This section provides non-limiting embodiments of compounds which may function as imaging agents and/or imaging agent precursors (also referred to herein as a diagnostic agent). In some embodiments, a compound is provided, wherein the compounds may be associated with a radioisotope, thereby forming an imaging agent (or diagnostic agent).

(1) In some embodiments, the diagnostic agent (or imaging agent) is of embodiment 1 of this second non-limiting set of embodiments, wherein the diagnostic agent (or imaging agent) comprises:
i) 1-10 targeting moieties;
ii) a chelator; and
iii) 0-1 linking groups between the targeting moiety and chelator;
wherein the targeting moiety is a matrix metalloproteinase inhibitor; and
wherein the chelator is capable of conjugating to the diagnostic metal.

(2) A diagnostic agent according to embodiment 1, wherein the targeting moiety is a matrix metalloproteinase inhibitor having an inhibitory constant $K_i$ of <1000 nM.

(3) A diagnostic agent according to any of embodiments 1-2, wherein the targeting moiety is a matrix metalloproteinase inhibitor having an inhibitory constant $K_i$ of <100 nM.

(4) A diagnostic agent according to any of embodiments 1-3, comprising 1-5 targeting moieties.

(5). A diagnostic agent according to any of embodiments 1-4, comprising one targeting moiety.

(6) A diagnostic agent any of embodiments 1-5, wherein the targeting moiety is an inhibitor of one or more matrix metalloproteinases selected from the group consisting of MMP-1, MMP-2, MMP-3, MMP-9, and MMP-14.

(7) A diagnostic agent of any of embodiments 1-6, wherein the targeting moiety is an inhibitor of one or more matrix metalloproteinases selected from the group consisting of MMP-2, MMP-9, and MMP-14.

(8) A diagnostic agent according to any one of embodiments 1-7 wherein the targeting moiety is a matrix metalloproteinase inhibitor of the formulae (Ia) or (Ib):

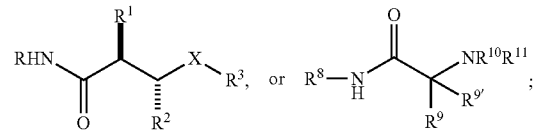

wherein,

R is independently OH or —CH$_2$SH;

R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;

R$^2$ is independently C$_{1-20}$ alkyl;

X is independently C=O or SO$_2$, provided when X is C=O, R$^3$ is

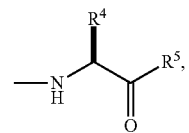

and when X is SO$_2$, R$^3$ is independently selected from the group: aryl substituted with 0-2 R$^6$, and heterocycle substituted with 0-2 R$^6$;

R$^4$ is independently selected at each occurrence from the group: C$_{1-6}$ alkyl, phenyl, and benzyl;

R$^5$ is independently at each occurrence from the group: NH(C$_{1-6}$ alkyl), NH-phenyl, and M-heterocycle; wherein said alkyl, phenyl and heterocycle groups are optionally substituted with a bond to the linking group or a bond to the chelator;

R$^6$ is independently aryloxy substituted with 0-3 R$^7$;

R$^7$ is independently halogen or methoxy;

or alternatively,

R$^1$ and R$^4$ may be taken together to form a bridging group of the formula —(CH$_2$)$_3$—O-phenyl-CH$_2$—, optionally substituted with a bond to the linking group or a bond to the chelator;

or alternatively,

R$^1$ and R$^2$ may be taken together to form a bridging group of the formula —(CH$_2$)$_3$—NH—, optionally substituted with a bond to the linking group or a bond to the chelator; or R$^1$ and R$^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;

R$^8$ is independently at each occurrence OH or phenyl, optionally substituted with a bond to the linking group or a bond to the chelator, provided that when R$^8$ is phenyl, R$^{10}$ is —C(=O)—CR$^{12}$—NH—CH(CH$_3$)—COOH;

R$^9$ and R$^{9'}$ are independently H, C$_{1-6}$ alkyl optionally substituted with a bond to the linking group or a bond to the chelator, or are taken together with the carbon atom to which R$^9$ and R$^{9'}$ are attached to form a 5-7 atom saturated, partially unsaturated or aromatic ring system containing 0-3 heteroatoms selected from O, N, SO$_2$ and S, said ring system substituted with R$^6$ and optionally substituted with a bond to the linking group or a bond to the chelator;

R$^{10}$ and R$^{11}$ are independently H, or C$_{1-6}$ alkyl optionally substituted with a bond to the linking group or a bond to the chelator, or are taken together with the nitrogen atom to which they are attached to form a 5-7 atom saturated, partially unsaturated or aromatic ring system containing 0-3 heteroatoms selected from O, N, SO$_h$, and S, said ring system optionally substituted with 0-3 R$^{27}$, a bond to the linking group or a bond to the chelator;

or alternatively,

R$^9$ and R$^{10}$ are taken together with the carbon atom to which they are attached to form a 5-7 atom saturated, partially unsaturated or aromatic ring system containing 0-3 heteroatoms selected from O, N, SO$_2$ and S, said ring system optionally substituted with a bond to the linking group or a bond to the chelator; and R$^{12}$ is independently C$_{1-20}$ alkyl;

R$^{27}$ is =O, C$_{1-4}$ alkyl, or phenyl substituted with R$^{28}$;

R$^{28}$ is a phenoxy group substituted with 0-2 OCH$_3$ groups;

R$^{29}$ and R$^{30}$ taken together with the nitrogen atom through which they are attached form a C5-7 atom saturated ring system substituted with R$^{31}$; and R$^{31}$ is a benzyloxy group substituted with C1-4 alkyl.

(9). A diagnostic agent according to any one of embodiments 1-8 wherein the targeting moiety is a matrix metalloproteinase inhibitor of the formulae (Ia) or (Ib):

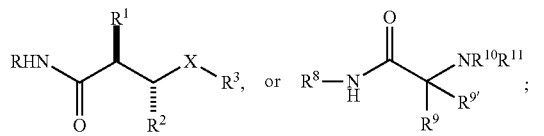

wherein,
R is OH;
R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;
R$^2$ is independently C$_{1-6}$ alkyl;
X is C=O;
R$^4$ is independently selected at each occurrence from the group: C$_{1-6}$ alkyl, phenyl, and benzyl;
R$^5$ is independently at each occurrence from the group: NH(C$_{1-6}$ alkyl), NH-phenyl, and NH-heterocycle; wherein said alkyl, phenyl and heterocycle groups are optionally substituted with a bond to the linking group or a bond to the chelator;
R$^6$ is independently aryloxy substituted with 0-3 R$^7$;
R$^7$ is independently halogen or methoxy;
or alternatively,
R$^1$ and R$^4$ may be taken together to form a bridging group of the formula —(CH$_2$)$_3$—O-phenyl-CH$_2$—, optionally substituted with a bond to the linking group or a bond to the chelator;
or alternatively,
R$^1$ and R$^2$ may be taken together to form a bridging group of the formula —(CH$_2$)$_3$—NH—, optionally substituted with a bond to the linking group or a bond to the chelators or
R$^1$ and R$^2$ taken together with the nitrogen and carbon atom through which they are attached form a C$_{5-7}$ atom saturated ring system substituted with one or more substituents selected from the group consisting of: a bond to Ln, a bond to Ch, and —C(=O)—NR$^{29}$R$^{30}$;
R$^8$ is OH;
R$^9$ and R$^{9'}$ are independently H. C$_{1-6}$ alkyl optionally substituted with a bond to the linking group or a bond to the chelator, or are taken together with the carbon atom to which R$^9$ and R$^{9'}$ are attached to form a 5-7 atom saturated, partially unsaturated or aromatic ring system containing 0-1 heteroatoms selected from O, N, said ring system optionally substituted with a bond to the linking group or a bond to the chelator;
R$^{10}$ and R$^{11}$ are independently H, or C$_{1-6}$ alkyl optionally substituted with a bond to the linking group or a bond to the chelator, or are taken together with the nitrogen atom to which they are attached to form a 5-7 atom saturated, partially unsaturated or aromatic ring system containing 0-1 heteroatoms selected from O, N, said ring system optionally substituted with 0-3 R$^{27}$, a bond to the linking group or a bond to the chelator;
or alternatively,
R$^9$ and R$^{10}$ are taken together with the carbon atom to which they are attached to form a 5-7 atom saturated, partially unsaturated or aromatic ring system containing 0-1 heteroatoms selected from O, N, said ring system optionally substituted with a bond to the linking group or a bond to the chelator; and
R$^{12}$ is independently C$_{1-6}$ alkyl)
R$^{27}$ is =O, C1-4 alkyl, or phenyl substituted with R$^{28}$;
R$^{28}$ is a phenoxy group substituted with 0-2 OCH$_3$ groups;
R$^{29}$ and R$^{30}$ taken together with the nitrogen atom through which they are attached form a C5-7 atom saturated ring system substituted with R$^{31}$; and
R$^{31}$ is a benzyloxy group substituted with C1-4 alkyl.

(10). A diagnostic agent according to any one of embodiments 1-9 wherein the targeting moiety is a matrix metalloproteinase inhibitor of the formulae (Ia) or (Ib): wherein:
R is —OH;
R$^2$ is C$_{1-6}$ alkyl;
X is C=O;
R$^3$ is

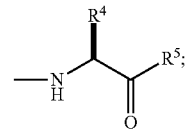

R$^1$ and R$^4$ are taken together to form a bridging group of formula —(CH$_2$)$_3$—O-phenyl-CH$_2$—;
R$^5$ is NH(C1-6alkyl), substituted with a bond to the linking group or a bond to the chelator.

(11) A diagnostic agent according to any one of embodiments 1-10, wherein:
R is —OH;
R$^9$ is C$_1$ alkyl substituted with a bond to Ln;
R$^{10}$ and R$^{11}$ taken together with the nitrogen atom to which they are attached form a 5 atom saturated ring system, said right system is substituted with 0-3 R$^{27}$;
R$^{27}$ is =O, C$_{1-4}$ alkyl, or phenyl substituted with R$^{28}$; and
R$^{28}$ is a phenoxy group substituted with 0-2 OCH$_3$ groups.

(12) A diagnostic agent according to any one of embodiments 1-11 wherein the
R is —OH;

R¹ and R² taken together with the nitrogen and carbon atom through which they are attached form a $C_{5-7}$ atom saturated ring system substituted with one or more substituents selected from the group consisting of: a bond to Ln, a bond to Ch, and —C(=O)—NR²⁹R³⁰;

R²⁹ and R³⁰ taken together with the nitrogen atom through which they are attached form a C5-7 atom saturated ring system substituted with R³¹; and R³¹ is a benzyloxy group substituted with C1-4 alkyl.

(13) A diagnostic agent according to any one of embodiments 1-12 wherein the linking group is of the formula:

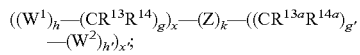

W¹ and W² are independently selected at each occurrence from the group: O, S, NH, NHC(=O), C(=O)NH, NR¹⁵C(=O), C(=O)NR¹⁵, C(=O), C(=O)O, OC(=O), NHC(=S)NH, NHC(=O)NH, SO₂, SO₂NH, —(OCH₂CH₂)₇₆₋₈₄—, (OCH₂CH₂)ₛ, (CH₂CH₂O)ₛ', (OCH₂CH₂CH₂)ₛ", (CH₂CH₂CH₂O)ₜ, and (aa)ₜ';

aa is independently at each occurrence an amino acid;

Z is selected from the group: aryl substituted with 0-3 R¹⁶, $C_{3-10}$ cycloalkyl substituted with 0-3 R¹⁶, and a 5-10 membered heterocyclic ring system containing 1-4 heteroatoms independently selected from N, S, and O and substituted with 0-3 R¹⁶;

R¹³, R¹³ᵃ, R¹⁴, R¹⁴ᵃ, and R¹⁵ are independently selected at each occurrence from the group: H, =O, COOH, SO₃H, PO₃H, $C_1$-$C_5$ alkyl substituted with 0-3 R¹⁶, aryl substituted with 0-3 R¹⁶, benzyl substituted with 0-3 R¹⁶, and $C_1$-$C_5$ alkoxy substituted with 0-3 R¹⁶, NHC(=O)R¹⁷, C(=O)NHR¹⁷, NHC(=O)NHR¹⁷, NHR¹⁷, R¹⁷, and a bond to the chelator;

R¹⁶ is independently selected at each occurrence from the group: a bond to the chelator, COOR¹⁷, C(=O)NHR¹⁷, NHC(=O)R¹⁷, OH, NHR¹⁷, SO₃H, PO₃H, —OPO₃H₂, —OSO₃H, aryl substituted with 0-3 R¹⁷, $C_{1-5}$ alkyl substituted with 0-1 R¹⁸, $C_{1-5}$ alkoxy substituted with 0-1 R¹⁸, and a 5-10 membered heterocyclic ring system containing 1-4 heteroatoms independently selected from N S, and O and substituted with 0-3 R¹⁷;

R¹⁷ is independently selected at each occurrence from the group: H, alkyl substituted with 0-1 R¹⁸, aryl substituted with 0-1 R¹⁸, a 5-10 membered heterocyclic ring system containing 1-4 heteroatoms independently selected from N, S, and O and substituted with 0-1 R¹⁸, $C_{3-10}$ cycloalkyl substituted with 0-1 R¹⁸, polyalkylene glycol substituted with 0-1 R¹⁸, carbohydrate substituted with 0-1 R¹⁸, cyclodextrin substituted with 0-1 R¹⁸, amino acid substituted with 0-1 R¹⁸, polycarboxyalkyl substituted with 0-1 R¹⁸, polyazaalkyl substituted with 0-1 R¹⁸, peptide substituted with 0-1 R¹⁸, wherein the peptide is comprised of 2-10 amino acids, 3,6-O-disulfo-B-D-galactopyranosyl, bis(phosphonomethyl) glycine, and a bond to the chelator;

R¹⁸ is a bond to the chelator;

k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5; and
x' is selected from 0, 1, 2, 3, 4, and 5.

(14) A diagnostic agent according to any one of embodiments 1-13 wherein

W¹ and W² are independently selected at each occurrence from the group: O, NH, NHC(=O), C(=O)NH, NR¹⁵C(=O), C(=O)NR¹⁵, C(=O), C(=O)O, OC(=O), NHC(=S)NH, NHC(=O)NH, SO₂, —(CH₂CH₂O)₇₆₋₈₄—, —(OCH₂CH₂)ₛ, (CH₂CH₂O)ₛ', (OCH₂CH₂CH₂)ₛ", (CH₂CH₂CH₂O)ₜ, and (aa)ₜ';

aa is independently at each occurrence an amino acid;

Z is selected from the group: aryl substituted with 0-1 R¹⁶, $C_{3-10}$ cycloalkyl substituted with 0-1 R¹⁶, and a 5-10 membered heterocyclic ring system containing 1-4 heteroatoms independently selected from N, S, and O and substituted with 0-1 R¹⁶;

R¹³, R¹³ᵃ, R¹⁴, R¹⁴ᵃ, and R¹⁵ are independently selected at each occurrence from the group: H, =O, COOH, SO₃H, $C_1$-$C_5$ alkyl substituted with 0-1 R¹⁶, aryl substituted with 0-1 R¹⁶, benzyl substituted with 0-1 R¹⁶, and $C_1$-$C_5$ alkoxy substituted with 0-1 R¹⁶, NHC(=O)R¹⁷, C(=O)NHR¹⁷, NC(=O)NR¹⁷, NHR¹⁷, R¹⁷, and a bond to the chelator;

k is 0 or 1;
a is selected from 0, 1, 2, 3, 4, and 5;
s' is selected from 0, 1, 2, 3, 4, and 5;
s" is selected from 0, 1, 2, 3, 4, and 5; and
t is selected from 0, 1, 2, 3, 4, and 5.

(15) A diagnostic agent according to embodiment 13 wherein wherein:
W¹ is C(=O)NR¹⁵;
h is 1;
g is 3;
R¹³ and R¹⁴ are independently H;
x is 1;
k is 0;
g' is 0;
h' is 1;
W² is NH; and
x' is 1.

(16) A diagnostic agent according to embodiment 13 wherein
x is 0;
k is 1;
Z is aryl substituted with 0-3 R¹⁶;
g' is 1;
W² is NH;
R¹³ᵃ and R¹⁴ᵃ are independently H;
h' is 1; and
x' is 1.

(17) A diagnostic agent according to embodiment 13 wherein
W¹ is C(=O)NR¹⁵;
h is 1;
g is 2;
R¹³ and R¹⁴ are independently H;
x is 1;
k is 0;
g' is 1;
R¹³ᵃ and R¹⁴ᵃ are independently H; or C1-5 alkyl substituted with 0-3 R¹⁶;
R¹⁶ is SO₃H;
W² is NHC(=O) or NH;
h' is 1; and
x' is 2.

(18). A diagnostic agent according to embodiment 13 wherein
$W^1$ is C(=O)NH;
h is 1;
g is 3;
$R^{13}$ and $R^{14}$ are independently N;
k is 0;
g' is 0;
x is 1;
$W^2$ is —NH(C=O)— or —(OCH$_2$CH$_2$)$_{76-84}$—;
h' is 2; and
x' is 1.

(19) A diagnostic agent according to embodiment 13 wherein
x is 0;
k is 0;
g' is 3;
h' is 1;
$W^2$ is NH; and
x' is 1.

(20) A diagnostic agent according to embodiment 13 wherein
x is 0;
Z is aryl substituted with 0-3 $R^{16}$;
k is 1;
g' is 1;
$R^{13a}R^{14a}$ are independently H;
$W^2$ is NHC(=O) or —(OCH$_2$CH$_2$)$_{76-84}$—; and
x' is 1.

(21) A diagnostic agent according to embodiment 13 wherein
$W^1$ is C=O;
g is 2;
$R^{13}$ and $R^{14}$ are independently H;
k is 0;
g' is 0;
h' is 1;
$W^2$ is NH; and
x' is 1.

(22) A compound according to embodiment 1 wherein the linking group is absent.

(23) A diagnostic agent according to any one of embodiments 1-22 wherein the chelator is a metal bonding unit having a formula selected from the group:

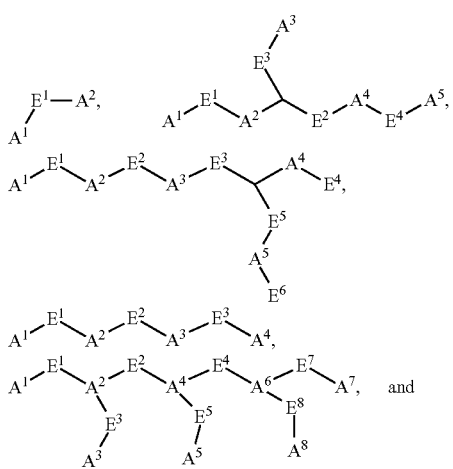

-continued

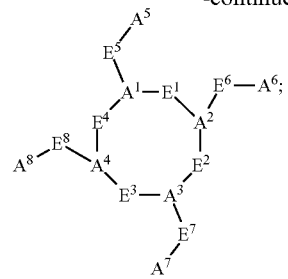

$A^1$, $A^2$, $A^3$, $A^4$, $A^5$, $A^6$, $A^7$, and $A^8$ are independently selected at each occurrence from the group: N, $NR^{26}$, $NR^{19}$, $NR^{19}R^{20}$, s, SH, —S(Pg), O, OH, $PR^{19}$, $PR^{19}R^{20}$, —O—P(O)($R^{21}$)—O—, P(O)$R^{21}R^{22}$, a bond to the targeting moiety and a bond to the linking group;

Pg is a thiol protecting group;

$E^1$, $E^2$, $E^3$, $E^4$, $E^5$, $E^6$, $E^7$, and $E^8$ are independently a bond, CH, or a spacer group independently selected at each occurrence from the group: $C_1$-$C_{16}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{19}$ and $R^{20}$ are each independently selected from the group: a bond to the linking group, a bond to the targeting moiety, hydrogen, $C_1$-$C_{10}$ alkyl substituted with 0-3 $R^{23}$, aryl substituted with 0-3 $R^{23}$, $C_{1-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, a 5-10 membered heterocyclic ring system containing 1-4 heteroatoms independently selected from N, S, and O and substituted with 0-3 $R^{23}$, and an electron, provided that when one of $R^{19}$ or $R^{20}$ is an electron, then the other is also an electron;

$R^{21}$ and $R^{22}$ are each independently selected from the group: a bond to the linking group, a bond to the targeting moiety, —OR, $C_1$-$C_{10}$ alkyl substituted with 0-3 $R^{23}$, $C_1$-$C_{10}$ alkyl substituted with 0-3 $R^{23}$, aryl substituted with 0-3 $R^{23}$, $C_{3-10}$ cycloalkyl substituted with 0-3 $R^{23}$, heterocyclo-$C_{1-10}$ alkyl substituted with 0-3 $R^{23}$, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{23}$ is independently selected at each occurrence from the group; a bond to the linking group, a bond to the targeting moiety, =O, F, Cl, Br, I, —CF$_3$, —CN, —CO$_2R^{24}$, —C(=O)$R^{24}$, —C(=O)N($R^{24}$)$_2$, —CHO, —CH$_2$O$R^{24}$, —OC(=O)$R^{24}$, —OC(=O)O$R^{24a}$, —O$R^{24}$, —OC(=O)N($R^{24}$)$_2$, —N$R^{25}$C(=O)$R^{24}$, —NR²⁵C(=O)OR²⁴ᵃ, —NR²⁵C(=O)₁N(R²⁴)₂, —NR²⁵SO₂N(R²⁴)₂, —NR²⁵SO₂R²⁴ᵃ, —SO₃H, —SO₂R²⁴ᵃ, —SR²⁴, —S(=O)R²⁴ᵃ, —SO₂N(R²⁴)₂, —N(R²⁴)₂, —NHC(=S)NHR²⁴, =NOR²⁴, NO₂, —C(=O)NHOR²⁴, —C(=O)NHNR²⁴R²⁴ᵃ, —OCH₂CO₂H, 2-(1-morpholino)ethoxy, $C_1$-$C_5$ alkyl. $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 R²⁴, and a 5-10 membered heterocyclic ring system containing 1-4 heteroatoms independently selected from N, S, and O; and wherein at least one of $A^1$, $A^2$, $A^3$. $A^4$, $A^5$, $A^6$, $A^7$, $A^8$ or R²³ is a bond to the linking group or targeting moiety;

R²⁴, R²⁴ᵃ, and R²⁵ are independently selected at each occurrence from the group: a bond to the linking group, a bond to the targeting moiety, H, $C_1$-$C_6$ alkyl, phenyl, benzyl, $C_1$-$C_6$ alkoxy, halide, nitro, cyano, and trifluoromethyl; and R²⁶ is a co-ordinate bond to a metal or a hydrazine protecting group; or a pharmaceutically acceptable salt thereof.

(24) A diagnostic agent according to any one of embodiments 1-23 wherein:

$A^1$, $A^2$, $A^3$, $A^4$, $A^5$, $A^6$, $A^7$, and $A^8$ are independently selected at each occurrence from the group: NR¹⁹, NR¹⁹R²⁰, S, SH, OH, a bond to the targeting moiety and a bond to the linking group;

$E^1$, $E^2$, $E^3$, $E^4$, $E^5$, $E^6$, $E^7$, and $E^8$ are independently a bond, CH, or a spacer group independently selected at each occurrence from the group: $C_1$-$C_{10}$ alkyl substituted with 0-3 R²³, aryl substituted with 0-3 R²³, $C_{3-10}$ cycloalkyl substituted with 0-3 R²³, and a 5-10 membered heterocyclic ring system containing 1-4 heteroatoms independently selected from N, S, and O and substituted with 0-3 R²³;

wherein at least one of $A^1$, $A^2$, $A^3$, $A^4$, $A^5$, $A^6$, $A^7$, $A^8$ and R²³ is a bond to the linking group or the targeting moiety;

R¹⁹, and R²⁰ are each independently selected from the group: a bond to the targeting moiety, a bond to the linking group, hydrogen, $C_1$-$C_{10}$ alkyl substituted with 0-3 R²³, aryl substituted with 0-3 R²³, a 5-10 membered heterocyclic ring system containing 1-4 heteroatoms independently selected from N, S, and O and substituted with 0-3 R²³, and an electron, provided that when one of R¹⁹ or R²⁰ is an electron, then the other is also an electron;

R²³ is independently selected at each occurrence from the group: a bond to the targeting moiety, a bond to the linking group, =O, F, Cl, Br, I, —CF₃, —CN, —CO₂R²⁴, —C(=O)R²⁴, —C(=O)N(R²⁴)₂, —CH₂OR²⁴, —OC(=O)R²⁴, —OC(=O)OR²⁴ᵃ, —OR²⁴, —OC(=O)N(R²⁴)₂, —NR²⁵C(=O)R²⁴, —NR²⁵C(=O)OR²⁴ᵃ, —NR²⁵C(=O)N(R²⁴)₂, —NR²⁵SO₂N(R²⁴)₂, —NR²⁵SO₂R²⁴ᵃ, —SO₃H, —SO₂R²⁴ᵃ, —S(=O)R²⁴ᵃ, —SO₂N(R²⁴)₂, —N(R²⁴)₂, —NHC(=S)NHR²⁴, =NOR¹⁸, —C(=O)NHNR¹⁸R¹⁸ᵃ, —OCH₂CO₂H, and 2-(1-morpholino)ethoxy; and R²⁴, R²⁴ᵃ, and R²⁵ are independently selected at each occurrence from the group: a bond to the linking group, H, and $C_1$-$C_6$ alkyl.

(25) A diagnostic agent according to any one of embodiments 1-24 wherein the chelator is of the formula:

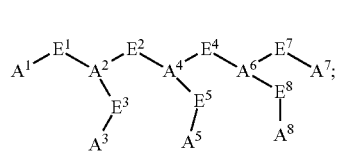

$A^1$ is a bond to the linking group;
$A^2$, $A^4$, and $A^6$ are each N;
$A^3$, $A^5$, $A^7$ and $A^8$ are each OH;
$E^1$, $E^2$, and $E^4$ are C2 alkyl,
$E^3$, $E^5$, $E^7$, and $E^8$ are $C_2$ alkyl substituted with 0-1 R²³;
R²³ is =O.

(26) A diagnostic agent according to any one of embodiments 1-25 wherein the chelator is of the formula:
$C_h$ is

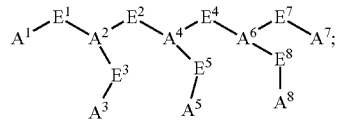

wherein:
A5 is a bond to Ln;
$A^1$, $A^3$, $A^7$ and $A^8$ are each OH;
$A^2$, $A^4$ and $A^6$ are each NH;
$E^1$, $E^3$, $E^5$, $E^7$, and $E^8$ are $C_2$ alkyl substituted with 0-1 R²³;
$E^2$, and $E^4$, are $C_2$ alkyl;
R²³ is =O.

(27) A diagnostic agent according to any one of embodiments 1-26 wherein the chelator is of the formula:

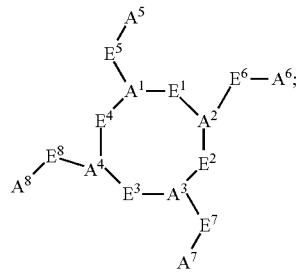

$A^1$, $A^2$, $A^3$ and $A^4$ are each N;
$A^5$, $A^6$ and $A^8$ are each OH;
$A^7$ is a bond to $L_n$;
$E^1$, $E^2$, $E^3$, $E^4$ are each independently $C_2$ alkyl; and
$E^5$, $E^6$, $E^7$, $E^8$ are each independently $C_2$ alkyl substituted with 0-1 R²³;
R²³ is =O.

(28) A diagnostic agent according to any one of embodiments 1-27 wherein the chelator is of the formula:

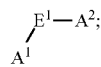

$A^1$ is NR²⁶;
R²⁶ is a co-ordinate bond to a metal or a hydrazine protecting group;
$E^1$ is a bond;

A² is NHR¹⁹;
R¹⁹ is a heterocycle substituted with R²³, the heterocycle being selected from pyridine and pyrimidine;
R²³ is selected from a bond to the linking group, C(=O)NHR²⁴ and C(=O)R²⁴; and
R²⁴ is a bond to the linking group.

(29) A diagnostic agent according to any one of embodiments 1-28 wherein the chelator is of the formula:

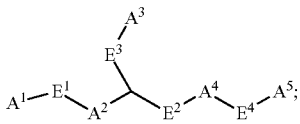

wherein:
A¹ and A⁵ are each —S(Pg);
Pg is a thiol protecting group;
E¹ and E⁴ are C₂ alkyl substituted with 0-1 R²³;
R²³ is =O;
A² and A⁴ are each —NH;
E² is CH₂;
E³ is C$_{1-3}$ alkyl substituted with 0-1 R²³;
A³ is a bond to Ln.

(30) A diagnostic agent according to any one of embodiments 1-29 wherein the chelator is of the formula:

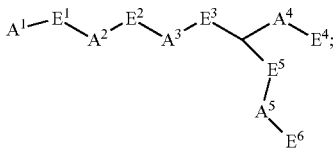

wherein:
A¹ is a bond to Ln;
E¹ is C₁ alkyl substituted by R²³;
A² is NH;
E² is C₂ alkyl substituted with 0-1R²³;
A³ is —O—P(O)(R²¹)—O;
E³ is C₁ alkyl;
A⁴ and A⁵ are each —O—;
E⁴ and E⁵ are each independently C$_{1-15}$ alkyl substituted with 0-1R²³;
E⁵ is C₁ alkyl;
R²¹ is —OH; and
R²³ is =O.

(31) A diagnostic agent according to embodiment 1 having the formula:

wherein, Q is a compound of Formulae (Ia) or (Ib):

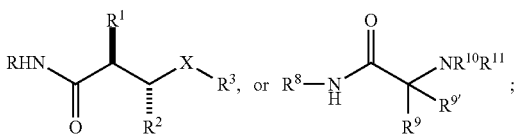

wherein,
R is independently OH or —CH₂SH;
R¹ is independently selected at each occurrence from the group: H, OH, C$_{1-3}$ alkyl, C$_{2-3}$ alkenyl, C$_{2-3}$ alkynyl, and heterocycle-S—CH₂—;

R² is independently C$_{1-20}$ alkyl;
X is independently C=O or SO₃, provided when X is C=O, R³ is

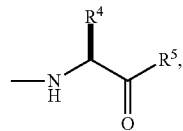

and when X is SO₂, R³ is independently selected from the group: aryl substituted with 0-2 R⁶, and heterocycle substituted with 0-2 R⁶;
R⁴ is independently selected at each occurrence from the group: C$_{1-6}$ alkyl, phenyl, and benzyl;
R⁵ is independently at each occurrence from the group: NH(C$_{1-6}$ alkyl), NH-phenyl, and NH-heterocycle; wherein said alkyl, phenyl and heterocycle groups are optionally substituted with a bond to L$_n$;
R⁶ is independently aryloxy substituted with 0-3 R⁷;
R⁷ is independently halogen or methoxy;
or alternatively,
R¹ and R⁴ may be taken together to form a bridging group of the formula —(CH)₃—O-phenyl-CH₃—, optionally substituted with a bond to L$_n$;
or alternatively,
R¹ and R² may be taken together to form a bridging group of the formula —(CH₂)₃—NH—, optionally substituted with a bond to L$_n$; or
R¹ and R² taken together with the nitrogen and carbon atom through which they are attached form a C$_{5-7}$ atom saturated ring system substituted with one or more substituents selected from the group consisting of: a bond to Ln, a bond to Ch, and —C(=O)—NR²⁹R³⁰,
R⁸ is independently at each occurrence OH or phenyl, optionally substituted with a bond to L$_n$, provided that when R⁸ is phenyl, R¹⁰ is —C(O)—CR¹²—NH—CH(CH₃)—COOH;
R⁹ and R⁹' are independently R, C$_{1-6}$ alkyl optionally substituted with a bond to La, or are taken together with the carbon atom to which they are attached to form a 5-7 atom saturated, partially unsaturated or aromatic ring system containing 0-3 heteroatoms selected from O, N, SO₂ and S, said ring system substituted with R⁶ and optionally substituted with a bond to L$_n$;
R¹⁰ and R¹¹ are independently H, or C$_{1-6}$ alkyl optionally substituted with a bond to La, or are taken together with the nitrogen atom to which they are attached to form a 5-7 atom saturated, partially unsaturated or aromatic ring system containing 0-3 heteroatoms selected from O, N, SO₂ and S, said ring system optionally substituted with 0-3 R²⁷ or a bond to L$_n$;
or alternatively,
R⁹ and R¹⁰ are taken together with the carbon atom to which they are attached to form a 5-7 atom saturated, partially unsaturated or aromatic ring system containing 0-3 heteroatoms selected from O, N, SO₂ and S, said ring system optionally substituted with a bond to L$_n$;
R¹² is independently C$_{1-20}$ alkyl;
d is selected from 1, 2, 3, 4, 5, 6, 7, 8, 9, and 10;
L$_n$ is a linking group having the formula:

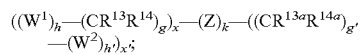

W¹ and W² are independently selected at each occurrence from the group: O, S, NH, NHC(=O), C(=O)NH, NR¹⁵C(=O), C(=O)NR¹⁵, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0-3 R¹⁶, C$_{3-10}$ cycloalkyl substituted with 0-3 R¹⁶, and a 5-10 membered heterocyclic ring system containing 1-4 heteroatoms independently selected from N, S, and O and substituted with 0-3 R¹⁶;

R¹³, R¹³ᵃ, R¹⁴, R¹⁴ᵃ, and R¹⁵ are independently selected at each occurrence from the group: H, =O, COOH, SO$_3$H, PO$_3$H, C$_1$-C$_5$ alkyl substituted with 0-3 R¹⁶, aryl substituted with 0-3 R¹⁶, benzyl substituted with 0-3 R¹⁶, and C$_1$-C$_5$ alkoxy substituted with 0-3 R¹⁶, NHC(=O)R¹⁷, C(=O)NHR¹⁷, NHC(=O)NHR¹⁷, NHR¹⁷, R¹⁷, and a bond to C$_h$;

R¹⁶ is independently selected at each occurrence from the group: a bond to C$_h$, COOR¹⁷, C(=O)NHR¹⁷, NHC(=O)R¹⁷, OH, NHR¹⁷, SO$_3$H, PO$_3$H, —OPO$_3$H$_2$, —OSO$_3$H, aryl substituted with 0-3 R¹⁷, C$_{1-5}$ alkyl substituted with 0-1 R¹⁸, C$_{1-5}$ alkoxy substituted with 0-1 R¹⁸, and a 5-10 membered heterocyclic ring system containing 1-4 heteroatoms independently selected from N, S, and O and substituted with 0-3 R¹⁷;

R¹⁷ is independently selected at each occurrence from the group: H, alkyl substituted with 0-1 R¹⁸, aryl substituted with 0-1 R¹⁸, a 5-10 membered heterocyclic ring system containing 1-4 heteroatoms independently selected from N, S, and O and substituted with 0-1 R¹⁸, C$_{3-10}$ cycloalkyl substituted with 0-1 R¹⁸, polyalkylene glycol substituted with 0-1 R¹⁸, carbohydrate substituted with 0-1 R¹⁸, cyclodextrin substituted with 0-1 R¹⁸, amino acid substituted with 0-1 R¹⁸, polycarboxyalkyl substituted with 0-1 R¹⁸, polyazaalkyl substituted with 0-1 R¹⁸, peptide substituted with 0-1 R¹⁸, wherein the peptide is comprised of 2-10 amino acids, 3,6-O-disulfo-B-D-galactopyranosyl, bis(phosphonomethyl) glycine, and a bond to C$_h$;

R¹⁸ is a bond to C$_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

C$_h$ is a metal bonding unit having a formula selected from the group:

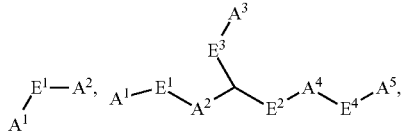

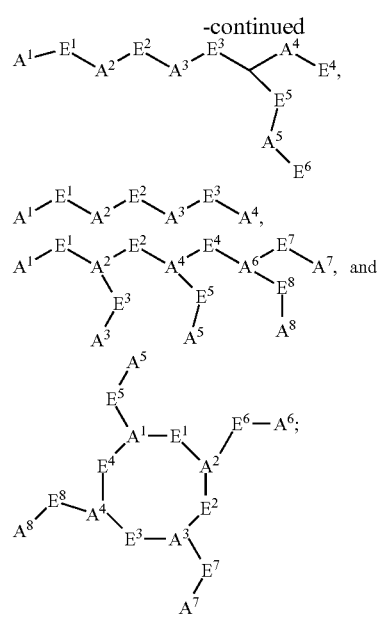

A¹, A², A³, A⁴, A⁵, A⁶, A⁷, and A⁸ are independently selected at each occurrence from the group: N, NR²⁶, NR¹⁹, NR¹⁹R²⁰, S, SH, —S(Pg), O, OH, PR¹⁹, PR¹⁹R²⁰, —O—P(O)(R²¹)—O—, P(O)R²¹R²², a bond to the targeting moiety and a bond to the linking group;

Pg is a thiol protecting group;

E¹, E², E³, E⁴, E⁵, E⁶, E⁷, and E⁸ are independently a bond, CH, or a spacer group independently selected at each occurrence from the group: C$_1$-C$_{16}$ alkyl substituted with 0-3 R²³, aryl substituted with 0-3 R²³, C$_{3-10}$ cycloalkyl substituted with 0-3 R²³, heterocyclo-C$_{1-10}$ alkyl substituted with 0-3 R²³, wherein the heterocyclo group is a 5-10 membered heterocyclic ring system containing 1-4 heteroatoms independently selected from N, S, and O, C$_{6-10}$ aryl-C$_{1-10}$ alkyl substituted with 0-3 R²³, C$_{1-10}$ alkyl-C$_{6-10}$ aryl-substituted with 0-3 R²³, and a 5-10 membered heterocyclic ring system containing 1-4 heteroatoms independently selected from N, S, and O and substituted with 0-3 R²³;

R¹⁹ and R²⁰ are each independently selected from the group: a bond to the linking group, a bond to the targeting moiety, hydrogen, C$_1$-C$_{10}$ alkyl substituted with 0-3 R²³, aryl substituted with 0-3 R²³, C$_{1-10}$ cycloalkyl substituted with 0-3 R²³, heterocyclo-C$_{1-10}$ alkyl substituted with 0-3 R²³, wherein the heterocyclo group is a 5-10 membered heterocyclic ring system containing 1-4 heteroatoms independently selected from N, S, and O, C$_{6-10}$ aryl-C$_{1-10}$ alkyl substituted with 0-3 R²³, C$_{1-10}$ alkyl-C$_{6-10}$ aryl-substituted with 0-3 R²³, a 5-10 membered heterocyclic ring system containing 1-4 heteroatoms independently selected from N, S, and O and substituted with 0-3 R²³, and an electron, provided that when one of R¹⁹ or R²⁰ is an electron, then the other is also an electron;

R²¹ and R²² are each independently selected from the group: a bond to the linking group, a bond to the targeting moiety, —OH, C$_1$-C$_{10}$ alkyl substituted with 0-3 R²³, C$_1$-C$_{10}$ alkyl substituted with 0-3 R²³, aryl substituted with 0-3 R²³, C$_{3-10}$ cycloalkyl substituted with 0-3 R²³, heterocyclo-C$_{1-10}$ alkyl substituted with 0-3 R²³, wherein the heterocyclo group is a 5-10 membered heterocyclic ring system containing 1-4 heteroatoms independently selected from N, S, and O, $C_{6-10}$ aryl-$C_{1-10}$ alkyl substituted with 0-3 $R^{23}$, $C_{1-10}$ alkyl-$C_{6-10}$ aryl-substituted with 0-3 $R^{23}$, and a 5-10 membered heterocyclic ring system containing 1-4 heteroatoms independently selected from N, S, and O and substituted with 0-3 $R^{23}$;

$R^{23}$ is independently selected at each occurrence from the group: bond to the linking group, a bond to the targeting moiety, —O, F, Cl, Br, I, —CF$_3$, —CN, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24a}$, —OR$^{24}$, —OC(=O)N(R$^{24}$)$_2$, —R$^{25}$C(=O)R$^{24}$, —NR$^{25}$C(=O)OR$^{24a}$, —NR$^{25}$C(=O)N(R$^{24}$)$_2$, —NR$^{25}$SO$_2$N(R$^{24}$)$_2$, —NR$^{25}$SO$_2$R$^{24a}$, —SO$_3$H, —SO$_2$R$^{24a}$, —SR$^{24}$, —S(=O)R$^{24a}$, —SO$_2$N(R$^{24}$)$_2$, —N(R$^{24}$)$_2$, —NHC(=S)NHR$^{24}$, =NOR$^{24}$, NO$_2$, —C(=O)NHOR$^{24}$, —C(=O)NHNR$^{24}$R$^{24a}$, —OCH$_2$CO$_2$H, 2-(1-morpholino)ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 $R^{24}$, and a 5-10 membered heterocyclic ring system containing 1-4 heteroatoms independently selected from N, S, and O; and wherein at least one of $A^1$, $A^2$, $A^3$, $A^4$, $A^5$, $A^6$, $A^7$, $A^8$ or $R^{23}$ is a bond to the linking group or targeting moiety;

$R^{24}$, $R^{24a}$, and $R^{25}$ are independently selected at each occurrence from the group: a bond to the linking group, a bond to the targeting moiety, H, $C_1$-$C_6$ alkyl, phenyl, benzyl, $C_1$-$C_6$ alkoxy, halide, nitro, cyano, and trifluoromethyl; and $R^{26}$ is a co-ordinate bond to a metal or a hydrazine protecting group; or a pharmaceutically acceptable salt thereof.

(32) A diagnostic agent according to Embodiment 31, wherein:
h' is 1;
$W^2$ is NH; and
x' is 1.

(33) A diagnostic agent according to any one of embodiments 1-,
wherein:
x is 0;
Z is aryl substituted with 0-3 $R^{16}$;
k is 1;
g' is 1;
$R^{13a}R^{14a}$ are independently H;
$W^2$ is NHC(=O) or —(OCH$_2$CH$_2$)$_{76-84}$—; and
x' is 1.

(34) A diagnostic agent according to any one of embodiments 31-33, wherein:
$W^1$ is C=O;
g is 2;
$R^{13}$ and $R^{14}$ are independently H;
k is 0;
g' is 0;
h' is 1;
$W^2$ is NH; and
x' is 1.

(35) A diagnostic agent according to any one of embodiments 31-34, wherein:

2-{[5-(3-{2-[(6-Hydroxycarbamoyl-7-isobutyl-8-oxo-2-oxa-9-aza-bicyclo[10.2.2]hexadeca-1(15),12(16),13-triene-10-carbonyl)-amino]-acetylamino}-propylcarbamoyl)-pyridin-2-yl]-hydrazonomethyl}-benzenesulfonic acid;

2-{[5-(4-{[(6-Hydroxycarbamoyl-7-isobutyl-8-oxo-2-oxa-9-aza-bicyclo[10.2.2]hexadeca-1(15),12(16),13-triene-10-carbonyl)-amino]-methyl}-benzylcarbamoyl)-pyridin-2-yl]-hydrazonomethyl}-benzenesulfonic acid;

2-[7-({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}methyl)-1,4,7,10-tetraaza-4,10-bis(carboxymethyl)cyclododecyl]acetic acid;

2-{7-[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl]-1,4,7,10-tetraaza-4,10-bis(carboxymethyl)cyclododecyl}acetic acid;

2-(7-{[N-(1-{N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]carbamoyl}-2-sulfoethyl)carbamoyl]methyl}-1,4,7,10-tetraaza-4,10-bis(carboxymethyl)cyclododecyl)acetic acid;

2-[7-({N-[1-(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)-2-sulfoethyl]carbamoyl}methyl)-1,4,7,10-tetraaza-4,10-bis(carboxymethyl)cyclododecyl]acetic acid;

2-({2-[({N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino)acetylamino)propyl]carbamoyl)methyl)(carboxymethyl)amino}ethyl){2-[bis(carboxymethyl)amino]ethyl}amino]acetic acid;

2-[(2-{[(N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-carbonylamino}methyl)phenyl]methyl}carbamoyl)methyl](carboxymethyl)amino}ethyl){2-[bis(carboxymethyl)amino]ethyl}amino]acetic acid;

N-[3-(2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}acetylamino)propyl]-4,5-bis[2-(ethoxyethylthio)acetylamino]pentanamide;

N-{[4-({[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}methyl)-phenyl]methyl}-4,5-bis[2-(ethoxyethylthio)acetylamino]-pentanamide;

1-(1,2-Dipalmitoyl-sn-glycero-3-phosphoethanolamino)-α,ω-dicarbonylPEG$_{3400}$-2-{[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]carbonylamino}-N-(3-aminopropyl)acetamide;

1-(1,2-Dipalmitoyl-sn-glycero-3-phosphoethanolamino)-α,ω-dicarbonylPEG$_{3400}$-[7-(N-hydroxycarbamoyl)(3S,6R,7S)-4-aza-6-(2-methylpropyl)-11-oxa-5-oxobicyclo[10.2.2]hexadeca-1(15),12(16),13-trien-3-yl]-N-{[4-(aminomethyl)phenyl]methyl}carboxamide conjugate;

2-[2-({5-[N-(5-(N-hydroxycarbamoyl)(5R)-5-{3-[4-(3,4-dimethoxyphenoxy)phenyl]-3-methyl-2-oxopyrrolidinyl}pentyl)carbamoyl](2-pyridyl)}amino)(1Z)-2-azavinyl]benzenesulfonic acid;

2-(2-{[5-[N-{3-[3-(N-hydroxycarbamoyl)(4S)-4-({4-[(4-methylphenyl)methoxy]piperidyl}carbonyl)piperidyl]-3-oxopropyl}carbamoyl](2-pyridyl)]amino}(1Z)-2-azavinyl)benzenesulfonic acid; and

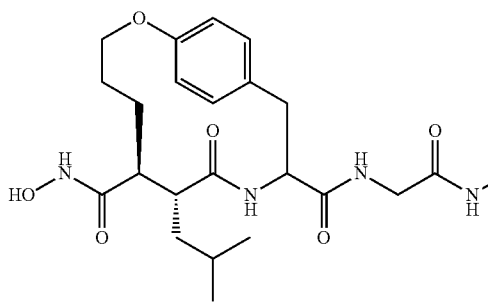

(36) A diagnostic agent according to any one of embodiments 31-35 wherein the diagnostic metal is selected from the group consisting of: a paramagnetic metal, a ferromagnetic metal, a gamma-emitting radioisotope, or an x-ray absorber.

(37) A diagnostic agent according to any one of embodiments 31-36 wherein the diagnostic metal is radioisotope selected from the group consisting of $^{99m}$Tc, $^{95}$Tc, $^{111}$In, $^{62}$Cu, $^{64}$Cu, $^{67}$Ga, and $^{68}$Ga.

(38). A diagnostic agent according to any one of embodiments 31-37 further comprising a first ancillary ligand and a second ancillary ligand capable of stabilizing the radioisotope.

(39) A diagnostic agent according to Embodiment 37, wherein the radioisotope is $^{99m}$Tc.

(40) A diagnostic agent according to Embodiment 37, wherein the radioisotope is $^{111}$In.

(41) A diagnostic agent according to embodiment 36 wherein the paramagnetic metal ion is selected from the group consisting of Gd(III), Dy(III), Fe(III), and Mn(II).

(42). A diagnostic agent according to embodiment 36 wherein the x-ray absorber is a metal is selected from the group consisting of: Re, Sm, Ho, Lu, Pa, Y, Bi, Pd, Gd, La, Au, Au, Yb, Dy, Cu, Rh, Ag, and Ir.

(43) A diagnostic composition comprising a compound according to any one of embodiments 1-42 or a pharmaceutically acceptable salt thereof, and a pharmaceutically acceptable carrier.

(44) A kit comprising a compound of to any one of embodiments 1-42, or a pharmaceutically acceptable salt form thereof and a pharmaceutically acceptable carrier.

(45) A kit according to Embodiment 44, wherein the kit further comprises one or more ancillary ligands and a reducing agent.

(46) A kit according to Embodiment 45, wherein the ancillary ligands are tricine and TPPTS.

(47) A kit according to Embodiment 45, wherein the reducing agent is tin(II).

(48) A diagnostic agent comprising an echogenic gas and a compound, wherein the compound comprises:
i) 1-10 targeting moieties;
ii) a surfactant (Sf); and
iii) 0-1 linking groups between the targeting moiety and surfactant;
wherein the targeting moiety is a matrix metalloproteinase inhibitor; and wherein the surfactant is capable of forming an echogenic gas filled lipid sphere or microbubble.

(49) A diagnostic agent according to embodiment 48, wherein the targeting moiety is a matrix metalloproteinase inhibitor having an inhibitory constant $K_i$ of <1000 nM.

(50) A diagnostic agent according to any one of embodiments 48-49, wherein the targeting moiety is a matrix metalloproteinase inhibitor having an inhibitory constant $K_i$ of <100 n.

(51) A diagnostic agent according to embodiment 48, comprising 1-5 targeting moieties.

(52). A diagnostic agent according to embodiment 48, comprising one targeting moiety.

(53) A diagnostic agent according to any one of embodiments 48-52, wherein the targeting moiety is an inhibitor of one or more matrix metalloproteinases selected from the group consisting of MMP-1, MMP-2, MMP-3, MMP-9, and MMP-14.

(54) A diagnostic agent according to any one of embodiments 48-53, wherein the targeting moiety is an inhibitor of one or more matrix metalloproteinases selected from the group consisting of MMP-2, MMP-9, and MMP-14.

(55) A diagnostic agent according to embodiment 48, wherein the targeting moiety is of the formulae (Ia) or (Ib):

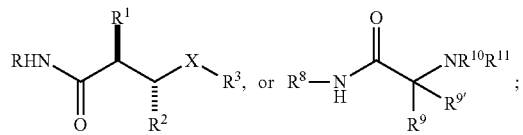

wherein,

R is independently OH or —CH$_2$SH;

R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;

R$^2$ is independently C$_{1-20}$ alkyl;

X is independently C=O or SO$_2$, provided when X is C=O, R$^3$ is

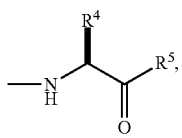

and when X is SO$_2$, R$^3$ is independently selected from the group: aryl substituted with 0-2 R$^6$, and heterocycle substituted with 0-2 R$^6$;

R$^4$ is independently selected at each occurrence from the group: C$_{1-6}$ alkyl, phenyl, and benzyl;

R$^5$ is independently at each occurrence from the group: NH(C$_{1-6}$ alkyl), NH-phenyl, and NH-heterocycle; wherein said alkyl, phenyl and heterocycle groups are optionally substituted with a bond to the linking group or a bond to the surfactant:

R$^6$ is independently aryloxy substituted with 0-3 R$^7$;

R$^7$ is independently halogen or methoxy;

or alternatively,

R$^1$ and R$^4$ may be taken together to form a bridging group of the formula —(CH$_2$)$_3$—O-phenyl-CH—, optionally substituted with a bond to the linking group or a bond to the surfactant;

or alternatively,

R$^1$ and R$^2$ may be taken together to form a bridging group of the formula —(CH$_2$)$_3$—NH—, optionally substituted with a bond to the linking group or a bond to the surfactant; or R$^1$ and R$^2$ taken together with the nitrogen and carbon atom through which they are attached form a C$_{5-7}$ atom saturated ring system substituted with one or more substituents selected from the group consisting of: a bond to Ln, a bond to Sf, and —C(=O)—NR$^{29}$R$^{30}$;

R$^8$ is independently at each occurrence OH or phenyl, optionally substituted with a bond to the linking group or a bond to the surfactant, provided that when R$^8$ is phenyl, R$^{10}$ is —C(=O)—CR$^{12}$—NH—CH(CH$_3$)—COOH;

R$^9$ and R$^{9'}$ are independently H, C$_{1-6}$ alkyl optionally substituted with a bond to the linking group or a bond to the surfactant, or are taken together with the carbon atom to which R$^9$ and R$^{9'}$ are attached to form a 5-7 atom saturated, partially unsaturated or aromatic ring system containing 0-3 heteroatoms selected from O, N, SO$_2$ and S, said ring system substituted with R$^6$ and optionally substituted with a bond to the linking group or a bond to the surfactant;

R$^{10}$ and R$^{11}$ are independently H, or C$_{1-6}$ alkyl optionally substituted with a bond to the linking group or a bond to the surfactant, or are taken together with the nitrogen atom to which they are attached to form a 5-7 atom saturated, partially unsaturated or aromatic ring system containing 0-3 heteroatoms selected from O, N, SO$_2$ and S, said ring system optionally substituted with 0-3 R$^{27}$, a bond to the linking group or a bond to the surfactant;

or alternatively,

R$^9$ and R$^{10}$ are taken together with the carbon atom to which they are attached to form a 5-7 atom saturated, partially unsaturated or aromatic ring system containing 0-3 heteroatoms selected from O, N, SO$_2$ and S, said ring system optionally substituted with a bond to the linking group or a bond to the surfactant; and R$^{12}$ is independently C$_{1-20}$ alkyl;

R$^{27}$ is =O, C1-4 alkyl, or phenyl substituted with R$^{28}$;

R$^{28}$ is a phenoxy group substituted with 0-2 OCH$_3$ groups;

R$^{29}$ and R$^{30}$ taken together with the nitrogen atom through which they are attached form a C$_{5-7}$ atom saturated ring system substituted with R$^{31}$; and R$^{31}$ is a benzyloxy group substituted with C1-4 alkyl.

(56) A diagnostic agent according to embodiment 55 wherein wherein the targeting moiety is a matrix metalloproteinase inhibitor of the formulae (Ia) or (Ib):

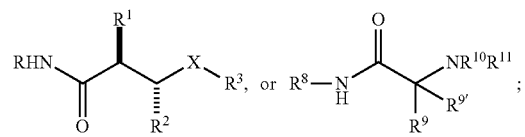

wherein,

R is OH;

R$^1$ is independently selected at each occurrence from the group: H, OH, C$_{1-3}$ alkyl, C$_{2-3}$ alkenyl, C$_{2-3}$ alkynyl, and heterocycle-S—CH$_2$—;

R$^2$ is independently C$_{1-6}$ alkyl;

X is C=O;

R$^4$ is independently selected at each occurrence from the group: C$_{1-6}$ alkyl, phenyl, and benzyl;

R$^5$ is independently at each occurrence from the group: NH(C$_{1-6}$ alkyl), NH-phenyl, and NH-heterocycle; wherein said alkyl, phenyl and heterocycle groups are optionally substituted with a bond to the linking group or a bond to the surfactant;

R$^6$ is independently aryloxy substituted with 0-3 R$^7$;

R$^7$ is independently halogen or methoxy;

or alternatively,

R$^1$ and R$^4$ may be taken together to form a bridging group of the formula —(CH$_2$)$_3$—O-phenyl-CH$_2$—, optionally substituted with a bond to the linking group or a bond to the surfactant;

or alternatively,

R$^1$ and R$^2$ may be taken together to form a bridging group of the formula —(CH$_2$)$_3$—NH—, optionally substituted with a bond to the linking group or a bond to the surfactant; or R$^1$ and R$^2$ taken together with the nitrogen and carbon atom through which they are attached form a C$_{5-7}$ atom saturated ring system substituted with one or more substituents selected from the group consisting of: a bond to Ln, a bond to Sf, and —C(=O)—NR$^{29}$R$^{30}$, R$^8$ is OH;

R$^9$ and R$^{9'}$ are independently H, C$_{1-6}$ alkyl optionally substituted with a bond to the linking group or a bond to the surfactant, or are taken together with the carbon atom to which R$^9$ and R$^{9'}$ are attached to form a 5-7 atom saturated, partially unsaturated or aromatic ring system containing 0-1 heteroatoms selected from O, N, said ring system optionally substituted with a bond to the linking group or a bond to the surfactant;

R$^{10}$ and R$^{11}$ are independently H, or C$_{1-6}$ alkyl optionally substituted with a bond to the linking group or a bond to the surfactant, or are taken together with the nitrogen atom to which they are attached to form a 5-7 atom saturated, partially unsaturated or aromatic ring system containing 0-1 heteroatoms selected from O, N, said ring system optionally substituted with 0-3 R$^{27}$, a bond to the linking group or a bond to the surfactant;

or alternatively,

R$^9$ and R$^{10}$ are taken together with the carbon atom to which they are attached to form a 5-7 atom saturated, partially unsaturated or aromatic ring system containing 0-1 heteroatoms selected from O, N, said ring system optionally substituted with a bond to the linking group or a bond to the surfactant; and R$^{12}$ is independently C$_{1-6}$ alkyl;

R$^{27}$ is =O, C$_{1-4}$ alkyl, or phenyl substituted with R$^{28}$;

R$^{28}$ is a phenoxy group substituted with 0-2 OCH$_3$ groups;

R$^{29}$ and R$^{30}$ taken together with the nitrogen atom through which they are attached form a C5-7 atom saturated ring system substituted with R$^{31}$; and R$^{31}$ is a benzyloxy group substituted with C1-4 alkyl.

(57) A diagnostic agent according to any one of embodiments 55-57 wherein the targeting moiety is a matrix metalloproteinase inhibitor of the formulae (Ia) or (Ib):
wherein:
R is —OH;
R$^2$ is C$_{1-6}$ alkyl;
X is C=O;
R$^3$ is

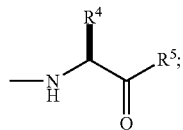

R$^1$ and R$^4$ are taken together to form a bridging group of formula —(CH$_2$)$_3$—O-phenyl-CH$_2$—;

R$^5$ is NH(C$_{1-6}$alkyl), substituted with a bond to the linking group or a bond to the surfactant.

(58) A diagnostic agent according to any one of embodiments 55-57 wherein:
R is —OH;
R$^9$ is C$_1$ alkyl substituted with a bond to Ln;
R$^{10}$ and R$^{11}$ taken together with the nitrogen atom to which they are attached form a 5 atom saturated ring system, said right system is substituted with 0-3 R$^{27}$;
R$^{27}$ is =O, C1-4 alkyl, or phenyl substituted with R$^{28}$; and
R$^{28}$ is a phenoxy group substituted with 0-2 OCH$_3$ groups.

(59) A diagnostic agent according to any one of embodiments 55-58 wherein
R is —OH;
R$^1$ and R$^2$ taken together with the nitrogen and carbon atom through which they are attached form a C$_{5-7}$ atom saturated ring system substituted with one or more substituents selected from the group consisting of: a bond to Ln, a bond to Sf, and —C(=O)—NR$^{29}$R$^{30}$;
R$^{29}$ and R$^{30}$ taken together with the nitrogen atom through which they are attached form a C5-7 atom saturated ring system substituted with R$^{31}$; and
R$^{31}$ is a benzyloxy group substituted with C1-4 alkyl.

(60) A diagnostic agent according to any one of embodiments 48-59 wherein the linking group is of the formula:

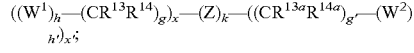

W$^1$ and W$^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid

Z is selected from the group: aryl substituted with 0-3 R$^{16}$, C$_{3-10}$ cycloalkyl substituted with 0-3 R$^{16}$, and a 5-10 membered heterocyclic ring system containing 1-4 heteroatoms independently selected from N, S, and O and substituted with 0-3 R$^{16}$;

R$^{13}$, R$^{13a}$, R$^{14}$, R$^{14a}$, and R$^{15}$ are independently selected at each occurrence from the group: H, =O, COOH, SO$_3$H, PO$_3$H, C$_1$-C$_5$ alkyl substituted with 0-3 R$^{16}$, aryl substituted with 0-3 R$^{16}$, benzyl substituted with 0-3 R$^{16}$, and C$_1$-C$_5$ alkoxy substituted with 0-3 R$^{16}$, NHC(O)R$^{17}$, C(=O)NHR$^{17}$, NHC(=O)NHR$^{17}$, NHR$^{17}$, R$^{17}$, and a bond to the surfactant;

R$^{16}$ is independently selected at each occurrence from the group: a bond to the surfactant, COOR$^{17}$, C(=O)NHR$^{17}$, NHC(=O)R$^{17}$, OH, NHR$^{17}$, SO$_3$H, PO$_3$H, —OPO$_3$H$_2$, —OSO$_3$H, aryl substituted with 0-3 R$^{17}$, C$_{1-5}$ alkyl substituted with 0-1 R$^{18}$, C$_{1-5}$ alkoxy substituted with 0-1 R$^{18}$, and a 5-10 membered heterocyclic ring system containing 1-4 heteroatoms independently selected from N, S, and O and substituted with 0-3 R$^{17}$;

R$^{17}$ is independently selected at each occurrence from the group: H, alkyl substituted with 0-1 R$^{18}$, aryl substituted with 0-1 R$^{18}$, a 5-10 membered heterocyclic ring system containing 1-4 heteroatoms independently selected from N, S, and O and substituted with 0-1 R$^{18}$, C$_{3-10}$ cycloalkyl substituted with 0-1 R$^{18}$, polyalkylene glycol substituted with 0-1 R$^{18}$, carbohydrate substituted with 0-1 R$^{18}$, cyclodextrin substituted with 0-1 R$^{18}$, amino acid substituted with 0-1 R$^{18}$, polycarboxyalkyl substituted with 0-1 R$^{18}$, polyazaalkyl substituted with 0-1 R$^{18}$, peptide substituted with 0-1 R$^{18}$, wherein the peptide is comprised of 2-10 amino acids, 3,6-O-disulfo-B-D-galactopyranosyl, bis(phosphonomethyl) glycine, and a bond to the surfactant;

R$^{18}$ is a bond to the surfactant;

k is selected from 0, 1, and 2;
h is selected from 0, 1, and 2;
h' is selected from 0, 1, and 2;
g is selected from 0, 1, 2, 3, 4, 5, 6, 7, 8, 9, and 10
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5; and
x' is selected from 0, 1, 2, 3, 4, and 5.

(61) A diagnostic agent according to any one of embodiments 48-60 wherein

W$^1$ and W$^2$ are independently selected at each occurrence from the group: O, NH, NHC(=O), C(=O)NH, NR$^{15}$C(=O), C(=O)NR$^{15}$, C(=O), C(=O)O, OC(=O), NHC(=S)NH, NHC(=O)NS, SO$_2$, —(CH$_2$CH$_2$O)$_{76-84}$—, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0-1 R$^{16}$, C$_{3-10}$ cycloalkyl substituted with 0-1 R$^{16}$, and a 5-10 membered heterocyclic ring system containing 1-4 heteroatoms independently selected from N, S, and O and substituted with 0-1 R$^{16}$;

R$^{13}$, R$^{13a}$, R$^{14}$, R$^{14a}$, and R$^{15}$ are independently selected at each occurrence from the group: H, =O, COOH, SO$_3$H, C$_1$-C$_5$ alkyl substituted with 0-1 R$^{16}$, aryl substituted with 0-1 R$^{16}$, benzyl substituted with 0-1 R$^{16}$, and C$_1$-C$_5$ alkoxy substituted with 0-1 R$^{16}$, NHC(=O)R$^{17}$, C(=O)NHR$^{17}$, NHC(=O)NHR$^{17}$, NHR$^{17}$, R$^{17}$, and a bond to the surfactant;
k is 0 or 1;
a is selected from 0, 1, 2, 3, 4, and 5;
s' is selected from 0, 1, 2, 3, 4, and 5;
s'' is selected from 0, 1, 2, 3, 4, and 5; and
t is selected from 0, 1, 2, 3, 4, and 5.
(62) A diagnostic agent according to embodiment 60 wherein:
W$^1$ is C(=O)NR$^{15}$;
h is 1;
g is 3;
R$^{13}$ and R$^{14}$ are independently H;
x is 1;
k is 0;
g' is 0;
h' is 1;
W$^2$ is NH; and
x' is 1.
(63) A diagnostic agent according to embodiment 60
x is 0;
k is 1;
Z is aryl substituted with 0-3 R$^{16}$;
g' is 1;
W$^2$ is NH;
R$^{13a}$ and R$^{14a}$ are independently H;
h' is 1; and
x' is 1.
(64) A diagnostic agent according to embodiment 60
W$^1$ is C(=O)NR$^{15}$;
h is 1;
g is 2;
R$^{13}$ and R$^{14}$ are independently H;
x is 1;
k is 0;
g' is 1;
R$^{13a}$ and R$^{14a}$ are independently H; or C1-5 alkyl substituted with 0-3 R$^{16}$;
R$^{16}$ is SO$_3$H;
W$^2$ is NHC(=O) or NH;
h' is 1; and
x' is 2.
(65) A diagnostic agent according to embodiment 60
W$^1$ is C(=O)NH;
h is 1;
g is 3;
R$^{13}$ and R$^{14}$ are independently H;
k is 0;
g' is 0;
x is 1;
W$^2$ is —NH(C=O)— or —(OCH$_2$CH$_2$)$_{76-84}$—;
h' is 2; and
x' is 1.
(66) A diagnostic agent according to embodiment 60
x is 0;
k is 0;
g' is 3;
h' is 1;
W$^2$ is 3H; and
x' is 1.
(67) A diagnostic agent according to embodiment 60
x is 0;
Z is aryl substituted with 0-3 R$^{16}$;
k is 1;

g' is 1;
R$^{13a}$R$^{14a}$ are independently H;
W$^2$ is NHC(=O) or —(OCH2CH2)$_{76-84}$—; and
x' is 1.
(68) A diagnostic agent according to embodiment 60
W$^1$ is C=O;
g is 2;
R$^{13}$ and R$^{14}$ are independently H;
k is 0;
g' is 0;
h' is 1;
W$^2$ is NH; and
x' is 1.
(69) A diagnostic agent according to embodiment 48 wherein the linking group is present.
(70) A diagnostic agent according to any one of embodiments 48-69 wherein
S$_f$ is a surfactant which is a lipid or a compound of the formula:

$$\begin{array}{c} E^9-A^{10}; \\ / \\ A^9 \end{array}$$

A$^9$ is selected from the group: OH and OR$^{32}$;
A$^{10}$ is OR$^{32}$;
R$^{32}$ is C(=O)C$_{1-20}$ alkyl;
E$^9$ is C$_{1-10}$ alkylene substituted with 1-3 R$^{33}$;
R$^{33}$ is independently selected at each occurrence from the group: R$^{35}$, —PO$_3$H—R$^{35}$, =O, —CO$_2$R$^{34}$, —C(=O)R$^{34}$, —C(=O)N(R$^{34}$)$_2$, —CH$_2$OR$^{34}$, —OR$^{34}$, —N(R$^{34}$)$_2$, C$_1$-C$_5$ alkyl, and C$_2$-C$_4$ alkenyl;
R$^{34}$ is independently selected at each occurrence from the group: R$^{35}$, H, C$_1$-C$_6$ alkyl, phenyl, benzyl, and trifluoromethyl;
R$^{35}$ is a bond to L$_n$;
and a pharmaceutically acceptable salt thereof.
(71) A diagnostic agent according to any one of embodiments 48-70 wherein the surfactant is a lipid or a compound of the formula:

$$\begin{array}{c} E^9-A^{10}; \\ / \\ A^9 \end{array}$$

A$^9$ is OR$^{32}$;
A$^{10}$ is OR$^{32}$;
R$^{32}$ is C(=O)C$_{1-15}$ alkyl;
E$^9$ is C$_{1-4}$ alkylene substituted with 1-3 R$^{33}$;
R$^{33}$ is independently selected at each occurrence from the group: R$^{35}$, —PO$_3$H—R$^{35}$, =O, —CO$_2$R$^{34}$, —C(=O)R$^{34}$, —CH$_2$OR$^{34}$, —OR$^{34}$, and C$_1$-C$_5$ alkyl;
R$^{34}$ is independently selected at each occurrence from the group: R$^{35}$, H, C$_1$-C$_6$ alkyl, phenyl, and benzyl; and
R$^{35}$ is a bond to L$_n$.
(72) A diagnostic agent according to any one of embodiments 48-71, wherein $$A^1-E^1-A^2-E^2-A^3-E^3-A^4-E^4;$$
$$\quad\quad\quad\quad\quad\quad\quad | \\ \quad\quad\quad\quad\quad\quad\quad E^5 \\ \quad\quad\quad\quad\quad\quad\quad / \\ \quad\quad\quad\quad\quad\quad A^5 \\ \quad\quad\quad\quad\quad\quad\quad\backslash E^6$$

wherein:

$A^1$ is a bond to Ln;
$E^1$ is $C_1$ alkyl substituted by $R^{23}$;
$A^2$ is NH;
$E^2$ is $C_2$ alkyl substituted with 0-1$R^{23}$;
$A^3$ is —O—P(O)($R^{21}$)—O;
$E^3$ is $C_1$ alkyl;
$A^4$ and $A^5$ are each —O—;
$E^4$ and $E^6$ are each independently $C_{1-6}$ alkyl substituted with 0-1$R^{23}$;
$E^5$ is $C_1$ alkyl;
$A^5$ is —O—;
$R^{21}$ is —OH; and
$R^{23}$ is =O.

(73) A diagnostic agent according to embodiment 48 wherein the compound is of the formula:

$$(Q)_d\text{-}L_n\text{-}S_f$$

wherein, Q is a compound of Formulae (Ia) or (Ib):

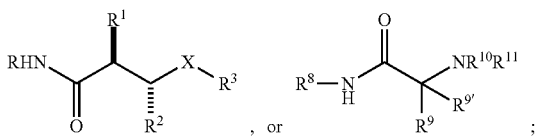

wherein,
R is independently OH or —CH$_2$SH;
$R^1$ is independently selected at each occurrence from the group: H, OH, $C_{1-3}$ alkyl, $C_{2-3}$ alkenyl, $C_{2-3}$ alkynyl, and heterocycle-S—CH$_2$—;
$R^2$ is independently $C_{1-20}$ alkyl;
X is independently C=O or SO$_2$, provided when X is C=O, $R^3$ is

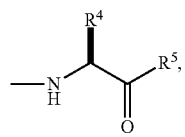

and when X is SO$_2$, $R^3$ is independently selected from the group: aryl substituted with 0-2 $R^6$, and heterocycle substituted with 0-2 $R^6$;
$R^4$ is independently selected at each occurrence from the group: $C_{1-6}$ alkyl, phenyl, and benzyl;
$R^5$ is independently at each occurrence from the group: NH($C_{1-6}$ alkyl), NH-phenyl, and NH-heterocycle; wherein said alkyl, phenyl and heterocycle groups are optionally substituted with a bond to $L_n$;
$R^6$ is independently aryloxy substituted with 0-3 $R^7$;
$R^7$ is independently halogen or methoxy;
or alternatively,
$R^1$ and $R^4$ may be taken together to form a bridging group of the formula —(CH$_2$)$_3$—O-phenyl-CH$_2$—, optionally substituted with a bond to $L_n$;
or alternatively,
$R^1$ and $R^2$ may be taken together to form a bridging group of the formula —(CH$_2$)$_3$—NH—, optionally substituted with a bond to $L_n$; or
$R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—NR$^{29}$R$^{30}$;
$R^8$ is independently at each occurrence OH or phenyl, optionally substituted with a bond to $L_n$, provided that when $R^8$ is phenyl, $R^{10}$ is —C(=O)—CR$^{12}$—NH—CH(CH$_3$)—COOH;
$R^9$ and $R^{9'}$ are independently H, $C_{1-6}$ alkyl optionally substituted with a bond to $L_n$, or are taken together with the carbon atom to which they are attached to form a 5-7 atom saturated, partially unsaturated or aromatic ring system containing 0-3 heteroatoms selected from O, N, SO$_2$ and S, said ring system substituted with $R^6$ and optionally substituted with a bond to $L_n$;
$R^{10}$ and $R^{11}$ are independently H, or $C_{1-6}$ alkyl optionally substituted with a bond to $L_n$, or are taken together with the nitrogen atom to which they are attached to form a 5-7 atom saturated, partially unsaturated or aromatic ring system containing 0-3 heteroatoms selected from O, N, SO$_2$ and S, said ring system optionally substituted with 0-3 $R^{27}$ or a bond to $L_n$;
or alternatively,
$R^9$ and $R^{10}$ are taken together with the carbon atom to which they are attached to form a 5-7 atom saturated, partially unsaturated or aromatic ring system containing 0-3 heteroatoms selected from O, N, SO$_2$ and S, said ring system optionally substituted with a bond to $L_n$;
$R^{12}$ is independently $C_{1-20}$ alkyl;
d is selected from 1, 2, 3, 4, 5, 6, 7, 8, 9, and 10;
$L_n$ is a linking group having the formula:

$$((W^1)_h\text{—}(CR^{13}R^{14})_g)_x\text{—}(Z)_k\text{—}((CR^{13a}R^{14a})_{g'}\text{—}(W^2)_{h'})_{x'};$$

$W^1$ and $W^2$ are independently selected at each occurrence from the group: O, S, NH, NHC(=O), C(=O)NH, NR$^{15}$C(=O), C(=O)NR$^{15}$, C(=O), C(=O)O, OC(=O), NHC(=S)NH, NHC(=O)NH, SO$_2$, SO$_2$NH, —(OCH$_2$CH$_2$)$_{76-84}$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_{t'}$, and (aa)$_t$;
aa is independently at each occurrence an amino acid;
Z is selected from the group: aryl substituted with 0-3 $R^{16}$, $C_{3-10}$ cycloalkyl substituted with 0-3 $R^{16}$, and a 5-10 membered heterocyclic ring system containing 1-4 heteroatoms independently selected from N, S, and O and substituted with 0-3 $R^{16}$;
$R^{13}$, $R^{13a}$, $R^{14}$, $R^{14a}$, and $R^{15}$ are independently selected at each occurrence from the group: H, =O, COOH, SO$_3$H, PO$_3$O, $C_1$-$C_5$ alkyl substituted with 0-3 $R^{16}$, aryl substituted with 0-3 $R^{16}$, benzyl substituted with 0-3 $R^{16}$, and $C_1$-$C_5$ alkoxy substituted with 0-3 $R^{16}$, NHC(=O)R$^{17}$, C(=O)NHR$^{17}$, NHC(=O)NHR$^{17}$, NHR$^{17}$, $R^{17}$, and a bond to Sf;
$R^{16}$ is independently selected at each occurrence from the group: a bond to Sf, COOR$^{17}$, C(=O)NR$^{17}$, NHC(=O)R$^{17}$, OH, NHR$^{17}$, SO$_3$H, PO$_3$H, —OPO$_3$H$_2$, —OSO$_3$H, aryl substituted with 0-3 $R^{17}$, $C_{1-5}$ alkyl substituted with 0-1 $R^{18}$, $C_{1-5}$ alkoxy substituted with 0-1 $R^{18}$, and a 5-10 membered heterocyclic ring system containing 1-4 heteroatoms independently selected from N, S, and O and substituted with 0-3 $R^{17}$;
$R^{17}$ is independently selected at each occurrence from the group: H, alkyl substituted with 0-1 $R^{18}$, aryl substituted with 0-1 $R^{18}$, a 5-10 membered heterocyclic ring system containing 1-4 heteroatoms independently selected from N, S, and O and substituted with 0-1 $R^{18}$, $C_{3-10}$ cycloalkyl substituted with 0-1 $R^{18}$, polyalkylene glycol substituted with 0-1 $R^{18}$, carbohydrate substituted with 0-1 $R^{18}$, cyclodextrin substituted with 0-1 $R^{18}$, amino acid substituted with 0-1 $R^{18}$, polycarboxyalkyl substituted with 0-1 $R^{18}$, polyazaalkyl substituted with 0-1 $R^{18}$, peptide substituted with 0-1 $R^{18}$, wherein the peptide is comprised of 2-10 amino acids, 3,6-O-disulfo-B-D-galactopyranosyl, bis(phosphonomethyl) glycine, and a bond to Sf;
$R^{18}$ is a bond to Sf;
k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5;
x' is selected from 0, 1, 2, 3, 4, and 5;
$S_f$ is a surfactant which is a lipid or a compound of the formula:

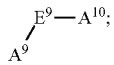

$A^9$ is selected from the group: OH and $OR^{32}$;
$A^{10}$ is $OR^{32}$;
$R^{32}$ is $C(=O)C_{1-20}$ alkyl;
$E^9$ is $C_{1-10}$ alkylene substituted with 1-3 $R^{33}$;
$R^{33}$ is independently selected at each occurrence from the group: $R^{35}$, $-PO_3H-R^{35}$, $=O$, $-CO_2R^{34}$, $-C(=O)R^{34}$, $-C(=O)N(R^{34})_2$, $-CH_2OR^{34}$, $-OR^{34}$, $-N(R^{34})_2$, $C_1-C_5$ alkyl, and $C_2-C_4$ alkenyl;
$R^{34}$ is independently selected at each occurrence from the group: $R^{35}$, H, $C_1-C_6$ alkyl, phenyl, benzyl, and trifluoromethyl;
$R^{35}$ is a bond to $L_n$; or
Sf is of the formula:

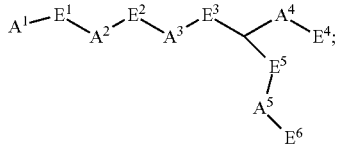

wherein:
$A^1$ is a bond to Ln;
$E^1$ is $C_1$ alkyl substituted by $R^{23}$;
$A^2$ is NH;
$E^2$ is $C_2$ alkyl substituted with $0-1R^{23}$;
$A^3$ is $-O-P(O)(R^{21})-O$;
$E^3$ is $C_1$ alkyl;
$A^4$ and $A^5$ are each $-O-$;
$E^4$ and $E^6$ are each independently $C_{1-16}$ alkyl substituted with $0-1R^{23}$;
$E^5$ is $C_1$ alkyl;
$A^5$ is $-O-$;
$R^{21}$ is $-OH$; and
$R^{23}$ is $=O$; or
a pharmaceutically acceptable salt thereof.

(74) A diagnostic agent according to embodiment 73, wherein:
R is $-OH$;
$R^2$ is C1-6 alkyl;
X is $C=O$;
$R^3$ is

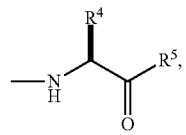

$R^1$ and $R^4$ are taken together to form a bridging group of formula $-(CH_2)_3-O$-phenyl-$CH_2-$;
$R^5$ is NH(C1-6alkyl), substituted with a bond to the linking group or a bond to the surfactant.

(75) A diagnostic agent according to any one of embodiments 73-74, wherein:
R is $-OH$;
$R^9$ is $C_1$ alkyl substituted with a bond to Ln;
$R^{10}$ and $R^{11}$ taken together with the nitrogen atom to which they are attached form a 5 atom saturated ring system, said right system is substituted with 0-3 $R^{27}$;
$R^{27}$ is $=O$, C1-4 alkyl, or phenyl substituted with $R^{28}$; and
$R^{28}$ is a phenoxy group substituted with 0-2 $OCH_3$ groups;
Sf is a surfactant which is a lipid or a compound of the formula:

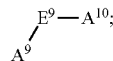

$A^9$ is $OR^{32}$;
$A^{10}$ is $OR^{32}$;
$R^{32}$ is $C(=O)C_{1-15}$ alkyl;
$E^9$ is $C_{1-4}$ alkylene substituted with 1-3 $R^{33}$;
$R^{33}$ is independently selected at each occurrence from the group: $R^{35}$, $-PO_3H-R^{35}$, $=O$, $-CO_2R^{34}$, $-C(=O)R^{34}$, $-CH_2OR^{34}$, $-OR^{34}$, and $C_1-C_5$ alkyl;
$R^{34}$ is independently selected at each occurrence from the group: $R^{35}$, H, $C_1-C_6$ alkyl, phenyl, and benzyl; and
$R^{35}$ is a bond to $L_n$.

(76) A diagnostic agent according to any one of embodiments 73-75, wherein:
R is $-OH$;
$R^9$ is $C_1$ alkyl substituted with a bond to Ln;
$R^{10}$ and $R^{11}$ taken together with the nitrogen atom to which they are attached form a 5 atom saturated ring system, said right system is substituted with 0-3 $R^{27}$;
$R^{27}$ is $=O$, C1-4 alkyl, or phenyl substituted with $R^{28}$; and
$R^{28}$ is a phenoxy group substituted with 0-2 $OCH_3$ groups;
Sf is a surfactant which is a lipid or a compound of the of the formula:

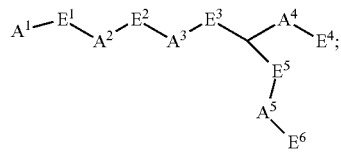

wherein:
A¹ is a bond to Ln;
E¹ is $C_1$ alkyl substituted by $R^{23}$;
A² is NH;
E² is $C_2$ alkyl substituted with 0-1$R^{23}$;
A³ is —O—P(O)($R^{21}$)—O;
E³ is $C_1$ alkyl;
$A^4$ and $A^5$ are each —O—;
$E^4$ and $E^6$ are each independently $C_{1-16}$ alkyl substituted with 0-1$R^{23}$;
$E^5$ is $C_1$ alkyl;
$A^5$ is —O—;
$R^{21}$ is —OH; and
$R^{23}$ is =O.

(77) A diagnostic agent according to any one of embodiments 73-76, wherein:
wherein
R is —OH;
$R^1$ and $R^2$ taken together with the nitrogen and carbon atom through which they are attached form a $C_{5-7}$ atom saturated ring system substituted with one or more substituents selected from the group consisting of: a bond to Ln, a bond to Sf, and —C(=O)—$NR^{29}R^{30}$;
$R^{29}$ and $R^{30}$ taken together with the nitrogen atom through which they are attached form a C5-7 atom saturated ring system substituted with $R^{31}$; and
$R^{31}$ is a benzyloxy group substituted with C1-4 alkyl.
d is selected from 1, 2, 3, 4, and 5;
W is independently selected at each occurrence from the group: O, NH, NHC(=O), C(=O)NH, $NR^{15}$C(=O), C(=O)$NR^{15}$, C(=O), C(=O)O, OC(=O), NHC(=S)NH, NHC(=O)NH, $SO_2$, $(OCH_2CH_2)_s$, $(CH_2CH_2O)_{s'}$, $(OCH_2CH_2CH_2)_{s''}$, $(CH_2CH_2CH_2O)_t$, and $(aa)_t$;
aa is independently at each occurrence an amino acid;
Z is selected from the group: aryl substituted with 0-1 $R^{16}$, $C_{3-10}$ cycloalkyl substituted with 0-1 $R^{16}$, and a 5-10 membered heterocyclic ring system containing 1-4 heteroatoms independently selected from N, S, and O and substituted with 0-1 $R^{16}$;
$R^{13}$, $R^{13a}$, $R^{14}$, $R^{14a}$, and $R^{15}$ are independently selected at each occurrence from the group: H, =O, COOH, $SO_3H$, $C_1$-$C_5$ alkyl substituted with 0-1 $R^{16}$, aryl substituted with 0-1 $R^{16}$, benzyl substituted with 0-1 $R^{16}$, and $C_1$-$C_5$ alkoxy substituted with 0-1 $R^{16}$, NHC(=O)$R^{17}$, C(=O)$NHR^{17}$, NHC(=O)$NHR^{17}$, $NHR^{17}$, $R^{17}$, and a bond to Sf;
k is 0 or 1;
s is selected from 0, 1, 2, 3, 4, and 5;
s' is selected from 0, 1, 2, 3, 4, and 5;
s" is selected from 0, 1, 2, 3, 4, and 5; and
t is selected from 0, 1, 2, 3, 4, and 5.

(78) A diagnostic agent according to according to any one of embodiments 73-77, wherein:
$W^1$ is C(=O)$NR^{15}$;
h is 1;
g is 3;
$R^{13}$ and $R^{14}$ are independently H;
x is 1;
k is 0;
g' is 0;
h' is 1;
$W^2$ is NH; and
x' is 1.

(79) A diagnostic agent according to embodiment 73, wherein:
x is 0;
k is 1;
Z is aryl substituted with 0-3 $R^{16}$;
g' is 1;
$W^2$ is NH;
$R^{13a}$ and $R^{14a}$ are independently H;
h' is 1; and
x' is 1.

(80) A diagnostic agent according to Embodiment 73, wherein:
$W^1$ is C(=O)$NR^{15}$;
h is 1;
g is 2;
$R^{13}$ and $R^{14}$ are independently H;
x is 1;
k is 0;
g' is 1;
$R^{13a}$ and $R^{14a}$ are independently H; or C1-5 alkyl substituted with 0-3 $R^{16}$;
$R^{16}$ is $SO_3H$;
$W^2$ is NHC(=O) or NH;
h' is 1; and
x' is 2.

(81) A diagnostic agent according to Embodiment 73, wherein:
$W^1$ is C(=O)NH;
h is 1;
g is 3;
$R^{13}$ and $R^{14}$ are independently H;
k is 0;
g' is 0;
x is 1;
$W^2$ is —NH(C=O)— or —$(OCH_2CH_2)_{76-84}$—;
h' is 2; and
x' is 1.

(82) A diagnostic agent according to Embodiment 73, wherein:
x is 0;
k is 0;
g' is 3;
h' is 1;
$W^2$ is NH; and
x' is 1.

(83) A diagnostic agent according to Embodiment 73, wherein:
x is 0;
z is aryl substituted with 0-3 $R^{16}$;
k is 1;
g' is 1;
$R^{13a}R^{14a}$ are independently H;
$W^2$ is NHC(=O) or —$(OCH_2CH_2)_{76-84}$—; and
x' is 1.

(84) A diagnostic agent according to Embodiment 73, wherein:
$W^1$ is C=O;
g is 2;
$R^{13}$ and $R^{14}$ are independently R;
k is 0;
g' is 0;
h' is 1;
$W^2$ is NH; and
x' is 1.

(85) A diagnostic agent according to Embodiment 1, wherein the compound is selected from the group consisting of:

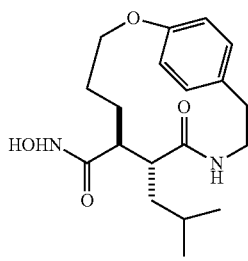
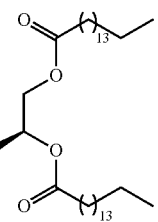
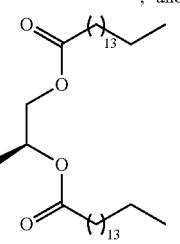
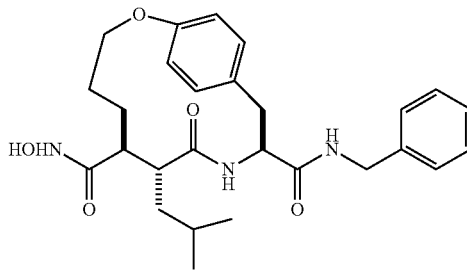

; and

(86) A diagnostic agent according to embodiment 48, wherein: wherein the echogenic gas is a perfluorocarbon gas or sulfur hexafluoride.

(87) A diagnostic agent according to embodiment 86 wherein said perfluorocarbon is selected from the group consisting of perfluoromethane, perfluoroethane, perfluoropropane, perfluorobutane, perfluorocyclobutane, perfluoropentane, and perfluorohexane.

(88) A diagnostic composition comprising a compound according to embodiment 48 or a pharmaceutically acceptable salt thereof, and a pharmaceutically acceptable carrier.

(89) A diagnostic composition comprising a compound according to embodiment 48 or a pharmaceutically acceptable salt form thereof, an echogenic gas and a pharmaceutically acceptable carrier.

(90) A diagnostic composition comprising a compound according to embodiment 48 further comprising: 1,2-dipalmitoyl-an-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

c. Third Non-Limiting Set of Embodiments of Imaging Agents or Precursors Thereof Matrix metalloproteinase (MMP) activity and extracellular matrix degradation is dependent on the comparative balance between MMPs and TIMPs. Elevated TIMP activity suppresses angiogenesis via inhibition of endothelial cell migration. TIMPs and synthetic small molecules or matrix metalloproteinase inhibitors have therapeutic potential for diseases involving elevated levels of MMP activity (Whittaker, M. et al, Chem. Rev., 1999, 99, 2735-2776; Babine, R. E. et al, Chem. Rev., 1997, 97, 1359; De, B. et al, Ann. N.Y. Acad. Sci., 1999, 878, 40-60; Summers, J. B. et al, Annual Reports in Med. Chem., 1998, 33, 131).

A functional group, such as —CONH—OH, —COOH, or —SH, is necessary for a molecule to be an effective inhibitor of MMPs. This functional group is involved in the chelation of the active site zinc ion, and is commonly referred to as the zinc binding group or ZBG. The hydroxamate, for example, is a bidentate ligand for zinc.

In some embodiments, a compound comprises the formula, $(Q)_{d'}-L_n-(C_h-X)$, $(Q)_{d'}-L_n-(C_h-X^1)_{d'}$, $(Q)_{d'}-L_n-(C_h-X^2)_{d''}$, or $(Q)_{d'}-L_n-(C_h-X^3)$, wherein Q represents a compound that inhibits a matrix metalloproteinase, d is 1-10, d'=1-100, d" is 1-100, $L_n$ represents an optional linking group, C.sub.h represents a metal chelator or bonding moiety, X represents a radioisotope, $X^1$ represents paramagnetic metal ion, $X^2$ represents a paramagnetic metal ion or heavy atom containing insoluble solid particle, and $X^3$ represents a surfactant microsphere of an echogenic gas.

One class of compounds that that inhibits a matrix metalloproteinase (e.g., Q) are succinyl hydroxamates. A generic structure of succinyl hydroxamate is shown below (1-1).

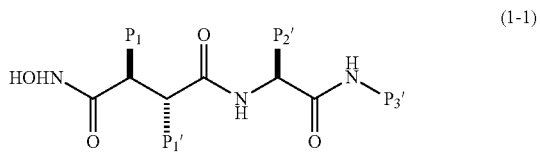

(1-1)

The ethylene spacer between the ZBG (—CONH—OH) and the succinyl amide is essential for potent activity. Substitution at $P_1$ tends to confer broad-spectrum activity on the MMPIs. Substituents at this position, in general, tend to point away from the enzyme. Moieties capable of hydrogen bonding and lipophilic substituents at the $P_1$ position α to the hydroxamate (Johnson, W. H. et al, J. Enz. Inhib., 1987, 2, 1) tend to enhance activity (1-2). Incorporation of a hydroxyl group (Beckett, P. R., et al, Drug Discovery Today, 1996, 1, 16) at that position improves oral activity in some case (1-3).

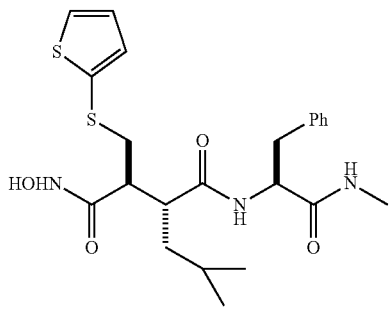
(1-2)

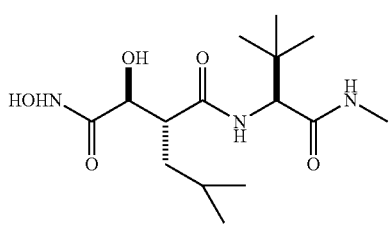
(1-3)

Substituents at the $P_1'$ position on the succinyl hydroxamates tend to impart selectivity to the MMPIs. The $S_1'$ pocket is deep for MMP-2, MMP-3, MMP-8 and MMP-9 and occluded (short) for MMP-1 and MMP-7. A long alkyl substituent at the $P_1'$ position, for example, imparts selectivity (Miller, A. et al, Bioorg. Med. Chem. Lett., 1997, 7, 193) for MMP-2 over MMP-1 and MMP-3 (1-4 and 1-5).

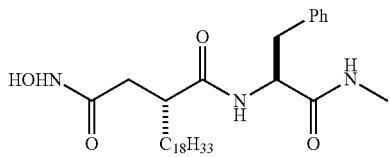
(1-4)

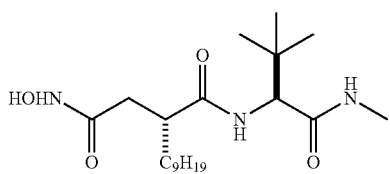
(1-5)

Substituents at the $P_2'$ position also point away from the enzyme. The $P_1$ and the $P_2'$ positions can be linked (Xue, C-B. et al, J. Med. Chem., 1998, 41, 1745; Steinman, D. H. et al, Bioorg. Med. Chem. Lett., 1998, 8, 2087) to form a macrocycle (1-6). Compounds such as (1-6) also exhibit nanomolar activity.

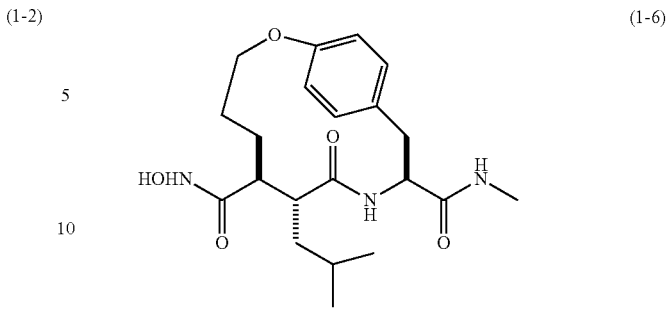
(1-6)

The nature of the macrocycle also imparts some selective inhibition among the MMPs. The $P_2'$ and the $P_3'$ positions may be cyclized to form lactams. The size of the lactam governs the selectivity.

The $P_3'$ position is a relatively open area in the succinyl hydroxamates, and a wide range of substitutents (for example (1-7)) may be introduced (Sheppard, G. S. et al, Bioorg. Med. Chem. Lett., 1998, 8, 3251) at this position. This position also offers the flexibility of attaching the optional linker, $L_n$, the chelator (s0, $C_h$, for the imageable moieties X and $X^1$, and the imageable moieties, $X^2$ and $X^3$.

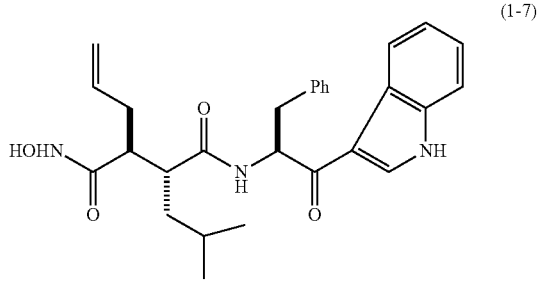
(1-7)

Other succinyl hydroxamates with modified $P_2'$ and $P_3'$ positions, such as (1-8) also have shown potent inhibition of MMPs. Those compounds and syntheses of them are further described in the following patent applications which are hereby incorporated by reference into this patent application: U.S. patent application Ser. Nos. 08/743,439, 60/127,594, and 60/127,635 and U.S. Pat. Nos. 6,057,336, 6,576,664, 6,455,522, 6,429,213, 6,365,587, 6,268,379, 6,495,548, 6,689,771, and 6,376,665

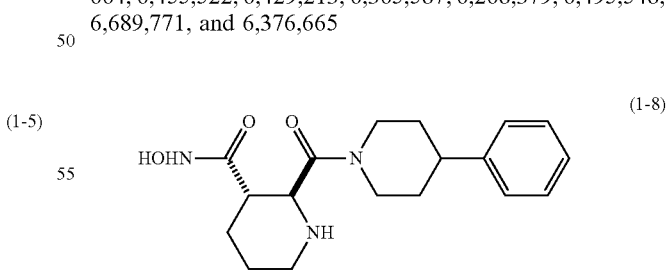
(1-8)

Another class of compounds of that inhibits a matrix metalloproteinase (e.g., Q) are sulfonamide hydroxamates, such as (1-9) and (1-10). Modification of the isopropyl substituent in (1-10) results in deep pocket MMP selectivity, for example MMP-2 vs MMP-1 (Santos, O. et al., J. Clin. Exp. Metastasis, 1997, 15, 499; MacPherson, L. J. et al, J. Med. Chem., 1997, 40, 2525).

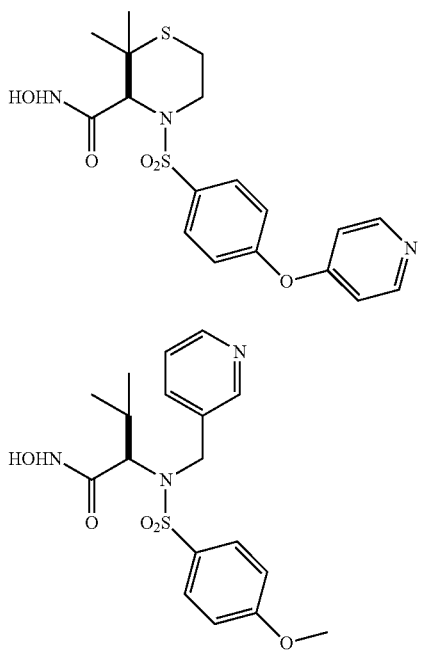

(1-9)

(1-10)

Additional examples of inhibitors, Q, include the derivatized alanine hydroxamates, such as compounds (1-11) and (1-12), which show selectivity for MMP-2 and MMP-9 over the other MMPs. The $P_1$ position is available for limited modification as described in the patents and applications incorporated by reference above. Those compounds and syntheses of them are further described in the following patent applications which are hereby incorporated by reference into this patent application: U.S. patent application Ser. Nos. 08/743,439, 60/127,594, and 60/127,635 and U.S. Pat. Nos. 6,057,336, 6,576,664, 6,455,522, 6,429,213, 6,365,587, 6,268,379, 6,495,548, 6,689,771, and 6,376,665

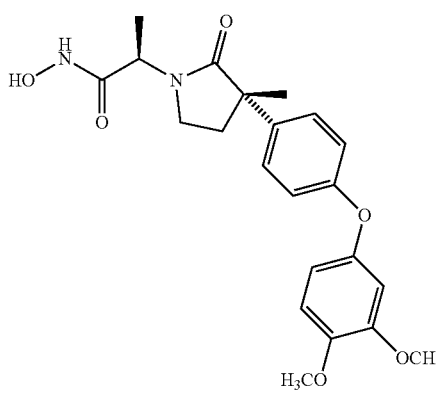

(1-11)

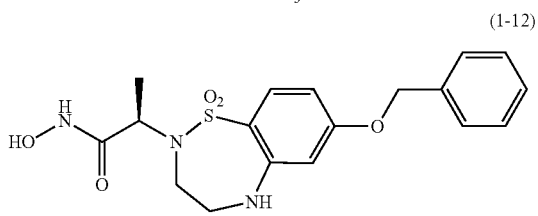

(1-12)

Other compounds with selectivity for MMP-2 and MMP-9 over MMP-1 include (1-13). In this example the alpha position has a quaternary carbon and the molecule does not contain any stereo centers (Lovejoy, B. et al., Nature Struct. Biol., 1999, 6, 217).

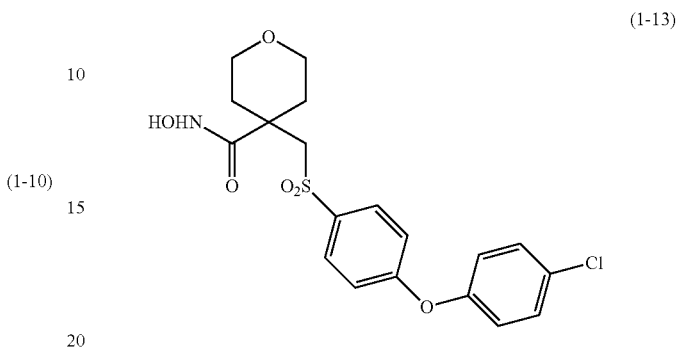

(1-13)

In the non-hydroxamate series, a number of compounds have been reported with a variety of structures. Use of carboxylic acid as the ZBG has also received attention. In the case of compound (1-14), significant selectivity for MMP-2 (vs MMP-1) was observed when X=butyl vs X=H (Sahoo, S. P. et al, Bioorg. Med. Chem. Lett., 1995, 5, 2441).

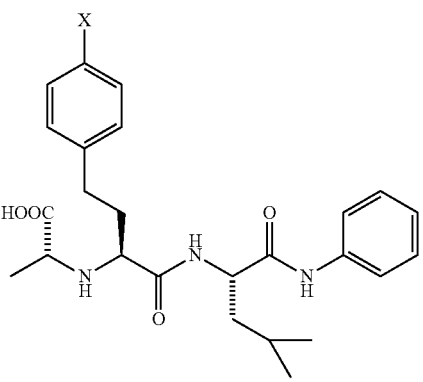

(1-14)

Although thiols are monodentate ZBGs, some succinyl thiols such as (1-15) have exhibited good activity (Levin, J. I. et al, Bioorg. Med. Chem. Lett., 1998, 8, 1163). The $P_2'$ position may be utilized to conjugate a variety of linkers and chelators (as described above) for the preparation of diagnostic agents. For example, the $P_3'$ position may be utilized to attach the optional linker, $L_n$, the chelator(s), $C_h$, for the imageable moieties X and $X^1$, and the imageable moieties, $X^2$ and $X^3$

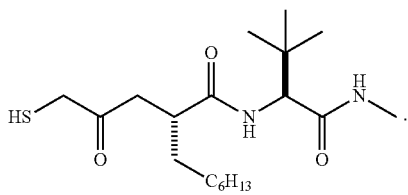

(1-15)

In some embodiments, the pharmaceuticals are comprised of inhibitors, Q, which exhibit selectivity for MMP-1, MMP-2, MMP-3, MMP-9, or MMP-14 alone or in combination over the other MMPs. Examples of moieties, Q, include compounds 1-4, 1-5, 1-6, 1-8, 1-9, 1-10, 1-11, 1-12, and 1-13.

In some embodiments, the inhibitors, Q, is selected to exhibit selectivity for MMP-2, MMP-9, or MMP-14 alone or in combination over the other MMPs. Examples of the such moieties, Q, include compounds 1-6, 1-8, 1-11, and 1-12.

Such pharmaceuticals can be synthesized by several approaches. One approach involves the synthesis of the targeting MMP inhibiting moiety, Q, and direct attachment of one or more moieties, Q, to one or more metal chelators or bonding moieties, Ch, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach, useful in the synthesis of pharmaceuticals wherein d is 1, involves the synthesis of the moiety, Q-$L_n$, together, by incorporating residue bearing $L_n$ into the synthesis of the MMP inhibitor, Q. The resulting moiety, Q-$L_n$, is then attached to one or more metal chelators or bonding moieties, $C_h$, or to a paramagnetic metal ion or heavy atom containing solid particle, or to an echogenic gas microbubble. Another approach involves the synthesis of an inhibitor, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The MMP inhibiting moieties, Q, optionally bearing a linking group, $L_n$, or a fragment of the linking group, can be synthesized using standard synthetic methods known to those skilled in the art. Methods include but are not limited to those methods described below.

Generally, peptides, polypeptides and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149-2154 (1963), the disclosure of which is hereby incorporated by reference.

d. Fourth Non-Limiting Set of Embodiments of Imaging Agents or Precursors Thereof In some embodiments, an imaging agent or imaging agent precursor is selected from the group consisting of:

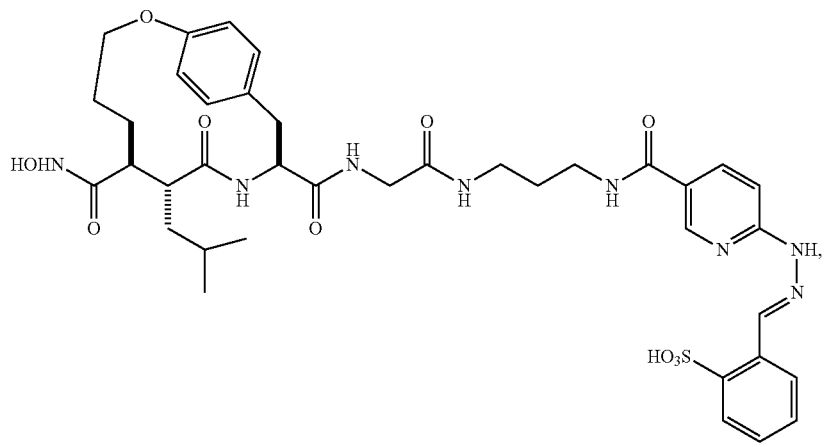

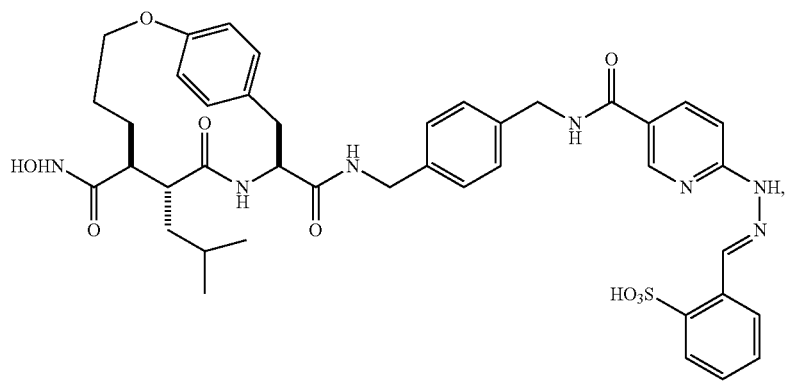

85 86
-continued
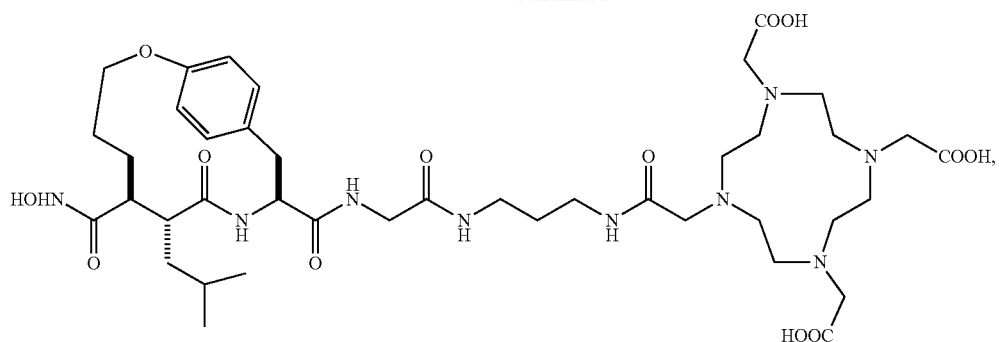
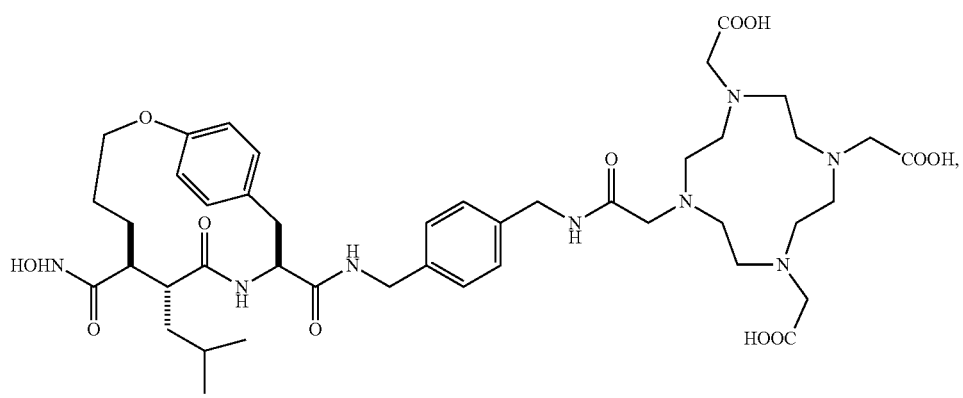
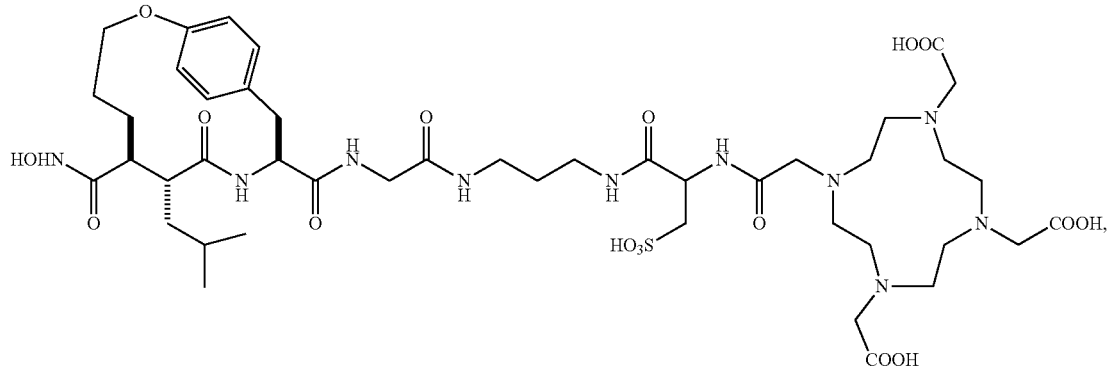
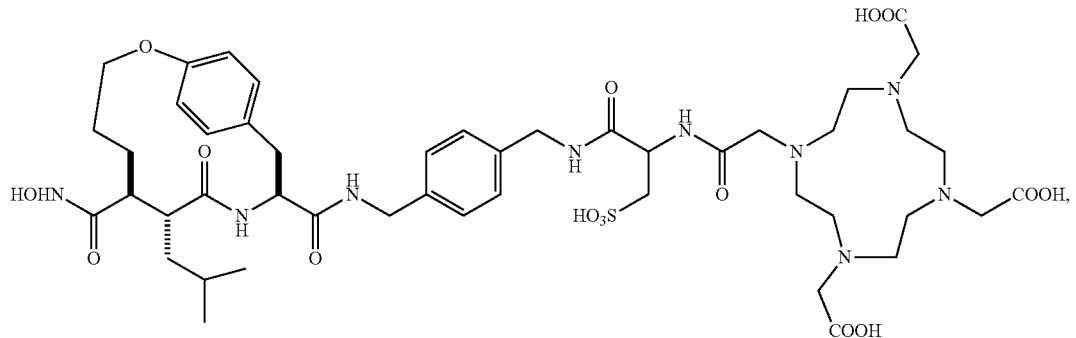

87
88
-continued
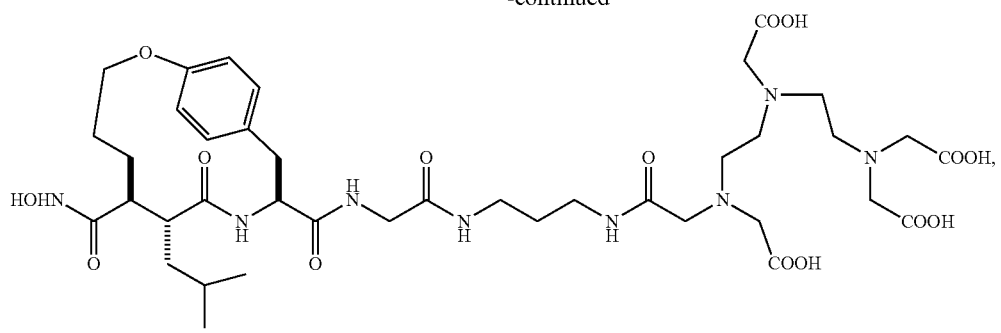
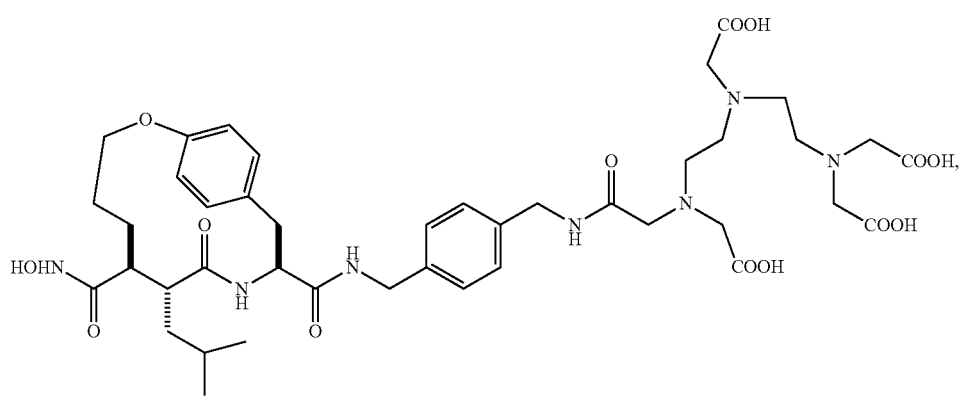
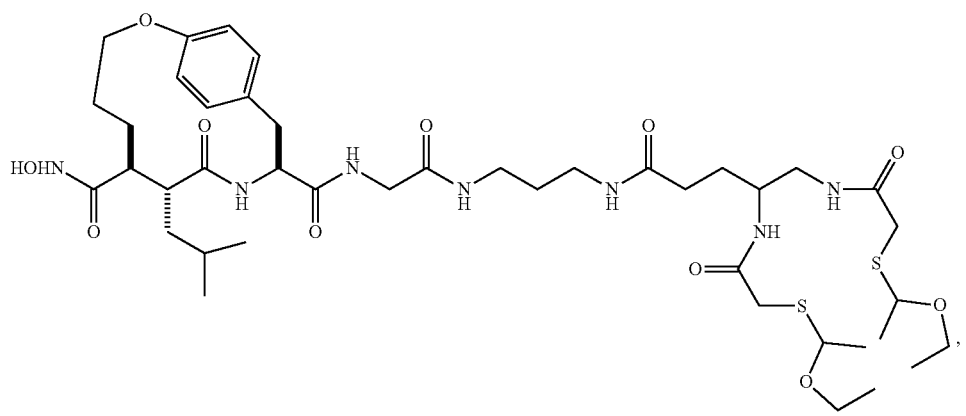
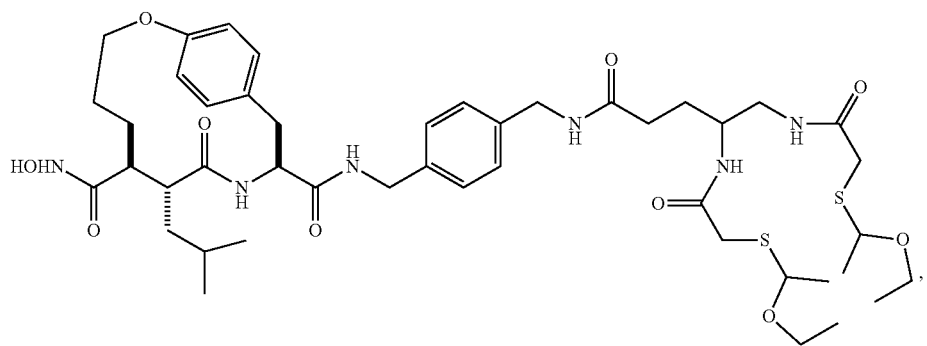

-continued
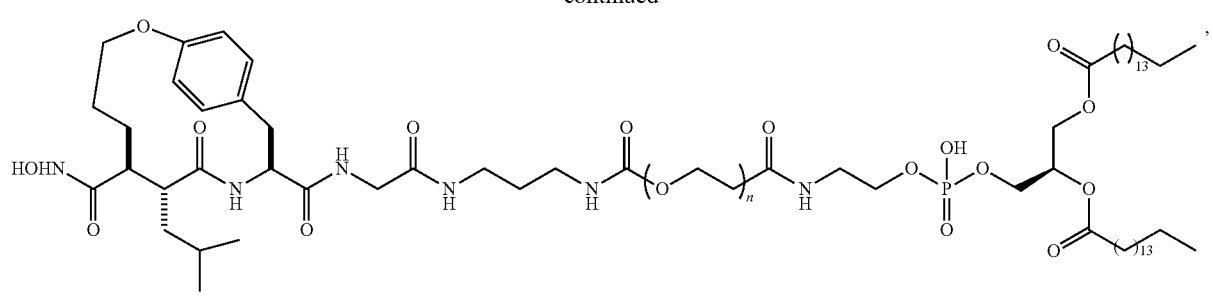
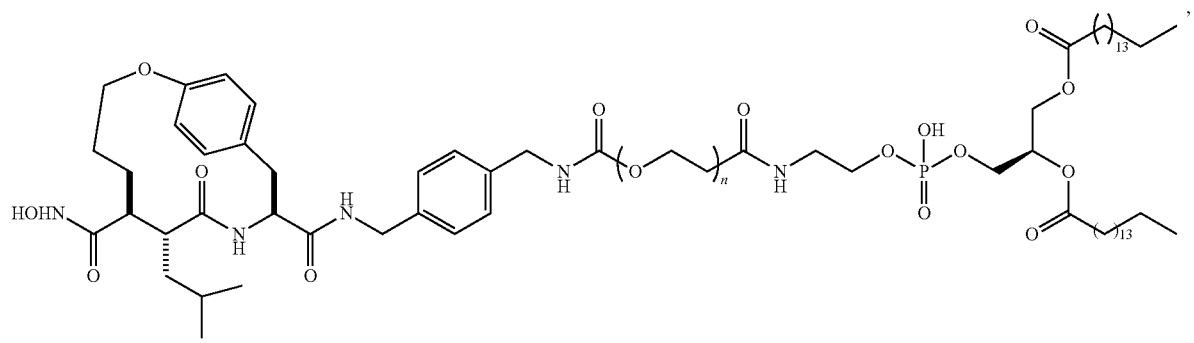
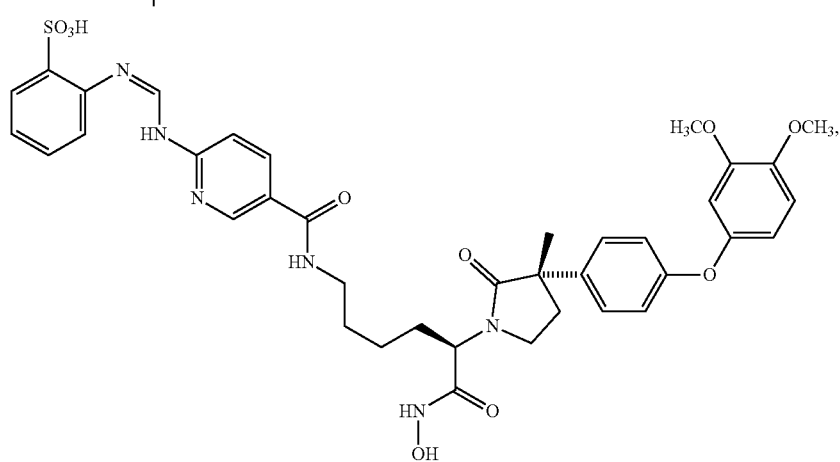
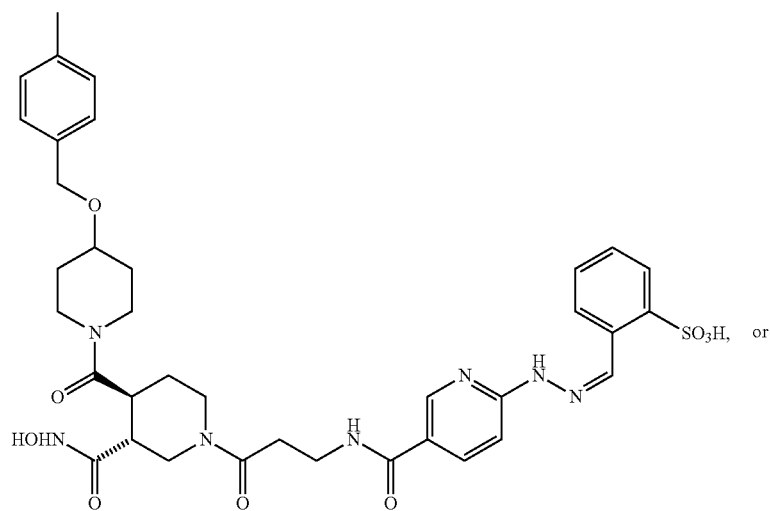

-continued

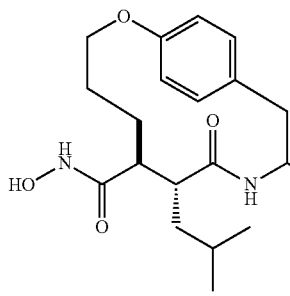
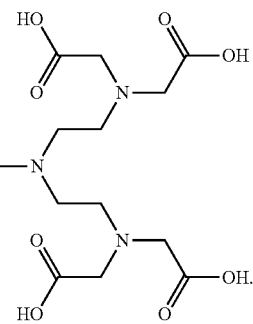

Subjects

As used herein, "subject" includes, but is not limited to, vertebrates, more specifically a mammal (e.g., a human, horse, pig, rabbit, dog, sheep, goat, non-human primate, cow, cat, guinea pig or rodent), a fish, a bird or a reptile or an amphibian. In some embodiments, the subject is a human subject. As used herein, "patient" refers to a subject afflicted with a disease or disorder. The term "patient" includes human and veterinary subjects.

In some instances, the subject is one that has not experienced a cardiovascular insult such as a myocardial infarction.

In some instances, the subject is one that has experienced a myocardial infarction. In some cases, the imaging methods may be performed within hours, days, weeks, or months after the myocardial infarction. In some instances, the imaging methods are performed repeatedly after a myocardial infarction including for example weekly, monthly, biannually, annually, etc. The imaging methods may be performed at different frequencies after a myocardial infarction. As an example, immediately after a myocardial infarction, the methods may be performed on a weekly or monthly basis for a period of time (e.g., 6 months or a year), and thereafter may be performed at a less regular interval (e.g., every 6 months, or every year) for a period of time or indefinitely.

In some instances, the subject is one having atherosclerosis (e.g., having symptoms of atherosclerosis). In some instances, the subject is one that does not have atherosclerosis (e.g., does not have symptoms of atherosclerosis).

Increased Risk Vs. Normal Population

The invention contemplates, in part, detecting presence and in some instances amount of an administered imaging agent (i.e., an MMP inhibitor linked to an imaging moiety) and comparing this to a control in order to determine an increased risk of developing AF or other indication (e.g., CAVD). The invention intends to determine an "above-normal" or "above-average" or "increased" risk of developing AF or other indication. An above-normal or above-average risk or increased risk is a risk that is greater than the risk of a normal subject or a population of normal subjects or a randomly selected population for developing AF or other indication. In some instances, an above-normal or above-average risk or increased risk is indicated by any level of MMP that is greater than the MMP level of a control. In some instances, the increased risk is further quantified by measuring the MMP level, wherein lower MMP levels indicate a lower "increased" risk and higher MMP levels indicate a higher "increased" risk, provided that even the lower MMP levels are still above normal or control levels.

The control level may be an MMP level determined using the same imaging agent in a normal subject (i.e., a subject that is known not to have AF), or it may be the average MMP level in a population of normal subjects, or it may be the average MMP level in a random sampling of the population at large. The control level may be one that is determined prior to the analysis of the subject rather than one that is determined in real time. The control level may therefore be a level that is obtained and established on a periodic basis (e.g., every 6 months, every year, etc.).

It will be understood that all subjects may have some risk of developing AF or other indication (e.g., CAVD). This risk may be referred to herein as the "normal risk." The normal risk may be established on an individual subject basis or on a population basis. For example, it may be determined as the risk of a "normal" subject developing AF (i.e., a subject that is not known to have AF), or the average risk in a normal population of developing AF, or the average risk in a randomly selected subpopulation from the population at large.

In still other embodiments, the invention further contemplates determining an increased risk of developing AF based on clinical trial results. As an example, a clinical trial may be performed that assesses MMP profile in a number of subjects and then follows those subjects over time in order to determine the nature of the profile that correlates with increased risk of AF. Those trials may be performed on subjects that previously had AF and that may have been treated with an AF therapy (such as but not limited to cardioversion), with an outcome of determining a profile that correlates with subjects that do not have a recurrence of AF after the trial and/or determining a profile that correlates with subjects that do have a recurrence of AF after the trial. Such trials may then be used to set the threshold (or cut point or control) to which future subjects are compared against.

Regardless of the control used, increased risk of developing AF (as a primary event or as a recurrent event) and/or likelihood of responding to a particular AF therapy (such as but not limited to cardioversion, ablation, pharmacological rate or rhythm control therapy, or implantable pacer) may be indicated by any MMP level that is above a control level, or it may be indicated by an MMP level that is at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, or 500%, or 10-fold, 20-fold, 50-fold, 100-fold, 200-fold, 300-fold 400-fold, or 500-fold more than the control level.

Imaging

The invention contemplates administering, to a subject, an imaging agent of the invention and then acquiring one or more images of the subject. The images will typically comprise images of the subject's heart, in whole or in part. Such images are therefore referred to herein as heart or cardiac images. Such images may comprise more than heart tissue and/or they may not comprise the entire heart tissue. In some instances, such images will comprise atrial myocardium, including left atrial myocardium.

The imaging modality will be dictated by the imaging moiety linked to the MMP inhibitor (and vice versa) as will be understood. In some embodiments, the imaging modality is single-photon emission computed tomography (referred to as SPECT or SPET), SPECT/CT, PET, ultrasound, MRI, and the like.

Myocardial (or Cardiac) Perfusion

In some instances, the invention further contemplates determining myocardial perfusion (i.e., blood flow through the heart) using myocardial perfusion imaging agents. In some instances, a measure of myocardial perfusion is used together with a measure of MMP levels. Myocardial perfusion imaging agents include but are not limited to flurpiridaz F18, Thallium-201, and Tc-Sestamibi.

In some cases, methods of the invention may include determining a parameter of, or the presence or absence of, myocardial ischemia, rest (R) and/or stress (S) myocardial blood flows (MBFs), coronary flow reserve (CFR), coronary artery disease (CAD), left ventricular ejection fraction (LVEF), end-systolic volume (ESV), end-diastolic volume (EDV), and the like.

Atrial Fibrillation (AF)

AF is an abnormal heart rhythm (cardiac arrhythmia) which involves the two small, upper heart chambers (i.e., the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses which result in irregular heartbeats.

AF is the most common cardiac arrhythmia. An individual may spontaneously alternate between AF and a normal rhythm (paroxysmal AF) or may continue with AF as the dominant cardiac rhythm without reversion to the normal rhythm (chronic AF).

AF is often asymptomatic, but may result in symptoms of palpitations, fainting, chest pain, or even heart failure. These symptoms are especially common when AF results in a heart rate which is either too fast or too slow. In addition, the erratic motion of the atria leads to blood stagnation (stasis) which increases the risk of blood clots that may travel from the heart to the brain and other areas. Thus, AF is an important risk factor for stroke, the most feared complication of AF.

The symptoms of AF may be treated with pharmacological agents which slow the heart rate. Several such pharmacological agents as well as electrical cardioversion may be used to convert AF to a normal heart rhythm. Surgical and catheter-based therapies may also be used to prevent AF in certain individuals. People with AF are often given blood thinners such as warfarin to protect them from strokes.

The American Heart Association, American College of Cardiology, and the European Society of Cardiology have proposed the following classification system based on simplicity and clinical relevance. "First Detected" refers to any patient newly diagnosed with AF, as the exact onset and chronicity of the disease is often uncertain. A patient with 2 or more identified episodes of AF is said to have "recurrent" AF. This is further classified into "paroxysmal" and "persistent" based on when the episode terminates without therapy. AF is said to be "paroxysmal" when it terminates spontaneously within 7 days, most commonly within 24 hours. "Persistent" or "chronic" AF is AF established for more than seven days. Differentiation of paroxysmal from chronic or established AF is based on the history of recurrent episodes and the duration of the current episode of AF. "Lone atrial fibrillation" (LAF) is defined as AF in the absence of clinical or echo cardiographic findings of cardiopulmonary disease. Patients with LAF who are under 65 have the best prognosis.

AF is usually accompanied by symptoms related to either rapid heart rate or embolization. Rapid and irregular heart rates may be perceived as palpitations, exercise intolerance, and occasionally produce angina and congestive symptoms of shortness of breath or edema. Sometimes the arrhythmia will be identified with the onset of a stroke or a transient ischemic attack (TIA). It is not uncommon to identify AF on a routine physical examination or electrocardiogram (ECG/EKG), as it may be asymptomatic in some cases. Paroxysmal AF is the episodic occurrence of the arrhythmia and may be difficult to diagnose. Episodes may occur with sleep or with exercise, and their episodic nature may require prolonged ECG monitoring (e.g. a Holter monitor) for diagnosis.

AF is diagnosed on an electrocardiogram, an investigation performed routinely whenever irregular heart beat is suspected. Characteristic findings include absence of P waves, unorganized electrical activity in their place, and irregularity of R-R interval due to irregular conduction of impulses to the ventricles. If paroxysmal AF is suspected, episodes may be documented with the use of Holter monitoring (continuous ECG recording for 24 hours or longer).

Diagnosis of AF sometimes involves analysis of renal function and electrolytes, as well as thyroid-stimulating hormone (commonly suppressed in hyperthyroidism and of relevance if amiodarone is administered for treatment) and a blood count. A chest X-ray is generally performed. In acute-onset AF associated with chest pain, cardiac troponins or other markers of damage to the heart muscle may be ordered. Coagulation studies (INR/aPTT) are usually performed, as anticoagulant medication may be commenced. A transesophageal echocardiogram may be indicated to identify any intracardiac thrombus.

AF is linked to several cardiac causes, but may occur in otherwise normal hearts. Known associations include carbon monoxide poisoning, high blood pressure, mitral stenosis (e.g. due to rheumatic heart disease or mitral valve prolapse), mitral regurgitation, heart surgery, coronary artery disease, hypertrophic cardiomyopathy, excessive alcohol consumption ("binge drinking" or "holiday heart syndrome"), hyperthyroidism, hyperstimulation of the vagus nerve, usually by having large meals ("binge eating"), lung pathology (such as pneumonia, lung cancer, pulmonary embolism, sarcoidosis), pericarditis, intense emotional turmoil, and congenital heart disease.

The main goals of treatment of AF are to prevent temporary circulatory instability and stroke. Rate control and rhythm control are principally used to achieve the former, while anticoagulation may be required to decrease the risk of the latter. AF can cause disabling and annoying symptoms. Palpitations, angina, lassitude (weariness), and decreased exercise tolerance are related to rapid heart rate and inefficient cardiac output caused by AF. Rate control treatments seek to reduce the heart rate to normal, usually 60 to 100 beats per minute. Rhythm control seeks to restore the normal heart rhythm, called normal sinus rhythm. Studies suggest that rhythm control is mainly a concern in newly diagnosed AF, while rate control is more important in the chronic phase.

AF with a persistent rapid rate can cause a form of heart failure called tachycardia induced cardiomyopathy. This can significantly increase mortality and morbidity. The early treatment of AF through either rate-control or rhythm control can prevent this condition and thereby improve mortality and morbidity.

Rate control methods include beta blockers (e.g. metoprolol), cardiac glycosides (e.g. digoxin), and calcium channel blockers (e.g. verapamil). These medications work by slowing the generation of impulses from the atria and the conduction of those impulses from the atria to the ventricles.

In refractory cases where none of the above drugs are sufficient, a variety of other antiarrhythmic drugs, most commonly including quinidine, flecamide, propafenone, disopyramide, sotalol, or amiodarone may be used. Of these, only propafenone, sotalol, and amiodarone (which possess some beta blocking activity) control the ventricular rate; the others may maintain sinus rhythm, but may actually increase the ventricular rate. Many of these drugs are less frequently used today than in the past. All (with the possible exception of amiodarone) increase the risk of ventricular tachycardia, which can be fatal. In symptomatic patients with normal heart function, however, the small increase in risk is usually felt to be acceptable. In the presence of heart failure, the only anti-arrhythmic drugs thought to be safe are amiodarone and dofetilide.

In patients with AF where rate control drugs are ineffective and it is not possible to restore sinus rhythm using cardioversion, non-pharmacological alternatives are available. For example, to control rate it is possible to destroy the bundle of cells connecting the upper and lower chambers of the heart—the atrioventricular node—which regulates heart rate, and to implant a pacemaker instead.

A more complex technique involves ablating groups of cells near the pulmonary veins where AF is thought to originate, or creating more extensive lesions in an attempt to prevent AF from establishing itself.

Rhythm control methods include electrical and chemical cardioversion. Electrical cardioversion involves the restoration of normal heart rhythm through the application of a DC (direct current) electrical shock. Chemical cardioversion is performed with drugs, such as amiodarone, propafenone or flecamide. Implantable pacing devices can also be used for rate management of AF patients and can be indicated versus traditional cardioversion.

The anti-arrhythmic medications often used in either pharmacological cardioversion or in the prevention of relapse to AF alter the flux of ions in heart tissue, making them less excitable, setting the stage for spontaneous and durable cardioversion. These medications are often used in concert with electrical cardioversion.

Whichever method of cardioversion is used, approximately 50% of patients relapse within one year, although the continued daily use of oral antiarrhythmic drugs may extend this period. The key risk factor for relapse is duration of AF, although other risk factors that have been identified include the presence of structural heart disease, and increasing age.

Radiofrequency ablation (RFA) uses radiofrequency energy to destroy abnormal electrical pathways in heart tissue. It is used in recurrent AF. The energy emitting probe (electrode) is placed into the heart through a catheter. The practitioner first "maps" an area of the heart to locate the abnormal electrical activity before the responsible tissue is eliminated. Ablation is a newer technique and has shown some promise for cases unresponsive to conventional treatments. New techniques include the use of cryoablation (tissue freezing using a coolant which flows through the catheter), and microwave ablation, where tissue is ablated by the microwave energy "cooking" the adjacent tissue. The abnormal electrophysiology can also be modified in a similar way surgically, and this procedure referred to as the Cox maze procedure, is commonly performed concomitantly with cardiac surgery. More recently, minimally invasive surgical variations on the Cox Maze procedure ("minimaze" procedures) have also been developed.

The Cox maze procedure is an open-heart surgical procedure intended to eliminate AF. "Maze" refers to the series of incisions made in the atria (upper chambers of the heart), which are arranged in a maze-like pattern. The intention was to eliminate AF by using incisional scars to block abnormal electrical circuits (atrial macrorentry) that AF requires. This procedure required an extensive series of endocardial (from the inside of the heart) incisions through both atria, a median sternotomy (vertical incision through the breastbone) and cardiopulmonary bypass (heart-lung machine). A series of improvements were made, culminating in 1992 in the Cox maze III procedure, which is now considered to be the "gold standard" for effective surgical cure of AF. The Cox maze III is sometimes referred to as the "traditional maze", the "cut and sew maze", or simply the "maze".

Minimaze surgery is minimally invasive cardiac surgery intended to cure AF. Minimaze refers to "mini" versions of the original maze procedure. These procedures are less invasive than the Cox maze procedure and do not require a median sternotomy (vertical incision in the breastbone) or cardiopulmonary bypass (heart-lung machine). These procedures use microwave, radiofrequency, or acoustic energy to ablate atrial tissue near the pulmonary veins.

In confirmed AF, anticoagulant treatment is a crucial way to prevent stroke. Treatment of AF patients over age 60, who also have one or more of: previous strokes (or warning strokes), hypertension (high blood pressure), diabetes, or congestive heart failure, with warfarin (also known as Coumadin® or Marevan®) results in a 60 to 70 percent reduction in the subsequent risk of stroke. Patients under age 65 who have any structural heart disease (i.e. valvular heart disease, ejection fraction<=35%, history of heart attack) may also benefit from warfarin.

The use of warfarin is associated with a delayed clinical effect. It typically takes three to five days to achieve a demonstrable anticoagulant effect. Hence, if an immediate anticoagulant effect is required, physicians could use heparin or other heparinoids such as enoxaparin to provide early anticoagulation. In practice, urgent anticoagulation is seldom indicated. Even in the setting of stroke complicating AF, clinical trial results do not support the routine use of immediate anticoagulation.

Patients under age 65 who do not have structural heart disease (i.e. with LAF) do not require warfarin, and can be treated with aspirin or clopidogrel. There is evidence that aspirin and clopidogrel are effective when used together. The new anticoagulant ximelagatran has been shown to prevent stroke with equal efficacy as warfarin.

Determining who should and should not receive anticoagulation with anti-coagulant drugs (e.g., warfarin, ximegalatran, heparin or other heparinoids) is not easy. The CHADS2 score is the best validated method of determining risk of stroke (and therefore who should be anticoagulated). The UK NICE guidelines have instead opted for an algorithm approach. The underlying problem is that if a patient has a yearly risk of stroke that is less than 2%, then the risks associated with taking warfarin outweigh the risk of getting a stroke.

MMPs

Key contributors to ECM synthesis/degradation are the matrix metalloproteinases (MMPs) and the endogenous tissue inhibitors of the metalloproteinases (TIMPs) (Visse R, et al. 2003; Matrisian L M, et al. 1990).

Matrix metalloproteinases (MMPs) are zinc-dependent endopeptidases; other family members are adamalysins, serralysins, and astacins. The MMPs belong to a larger family of proteases known as the metzincin superfamily.

The MMPs share a common domain structure. The three common domains are the pro-peptide, the catalytic domain and the haemopexin-like C-terminal domain which is linked to the catalytic domain by a flexible hinge region.

The MMPs are initially synthesized as inactive zymogens with a pro-peptide domain that must be removed before the enzyme is active. The pro-peptide domain is part of a "cysteine switch" that contains a conserved cysteine residue which interacts with the zinc in the active site and prevents binding and cleavage of the substrate keeping the enzyme in an inactive form. In the majority of the MMPs, the cysteine residue is in the conserved sequence PRCGxPD. Some MMPs have a prohormone convertase cleavage site (Furin-like) as part of this domain which when cleaved activates the enzyme. MMP-23A and MMP-23B include a transmembrane segment in this domain (PMID 10945999).

The MMPs can be subdivided in different ways. Use of bioinformatic methods to compare the primary sequences of the MMPs suggests the following evolutionary groupings of the MMPs: MMP-19; MMPs 11, 14, 15, 16 and 17; MMP-2 and MMP-9; all the other MMPs.

Analysis of the catalytic domains in isolation suggests that the catalytic domains evolved further once the major groups had differentiated, as is also indicated by the substrate specificities of the enzymes. The most commonly used groupings (by researchers in MMP biology) are based partly on historical assessment of the substrate specificity of the MMP and partly on the cellular localization of the MMP. These groups are the collagenases, the gelatinases, the stromelysins, and the membrane type MMPs (MT-MMPs). It is becoming increasingly clear that these divisions are somewhat artificial as there are a number of MMPs that do not fit into any of the traditional groups.

The collagenases are capable of degrading triple helical fibrillar collagens into distinctive ¾ and ¼ fragments. These collagens are the major components of bone and cartilage, and MMPs are the only known mammalian enzymes capable of degrading them. Traditionally, the collagenases are: MMP-1 (Interstitial collagenase), MMP-8 (Neutrophil collagenase), MMP-13 (Collagenase 3), MMP-18 (Collagenase 4), MMP-14 (MT1-MMP) has also been shown to cleave fibrillar collagen, and more controversially there is evidence that MMP-2 is capable of collagenolysis.

The stromelysins display a broad ability to cleave ECM proteins but are unable to cleave the triple-helical fibrillar collagens. The three canonical members of this group are: MMP-3 (Stromelysin 1), MMP-10 (Stromelysin 2), and MMP-11 (Stromelysin 3). MMP-11 shows more similarity to the MT-MMPs, is convertase-activatable and is secreted therefore usually associated to convertase-activatable MMPs.

The main substrates of gelatinasese are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

The secreted MMPs include MMP-11 (Stromelysin 3), MMP-21 (X-MMP), and MMP-28 (Epilysin).

The membrane-bound MMPs include: the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively).

All 6 MT-MMPs have a furin cleavage site in the pro-peptide, which is a feature also shared by MMP-11.

Other MMPs include MMP-12 (Macrophage metalloelastase), MMP-19 (RASI-1, occasionally referred to as stromelysin-4), Enamelysin (MMP-20), and MMP-27 (MMP-22, C-MMP), MMP-23A (CA-MMP), and MMP-23B.

Pharmaceutical Compositions and Administration

Once an imaging agent has been prepared or obtained, it may be combined with one or more pharmaceutically acceptable excipients to form a pharmaceutical composition that is suitable for administering to a subject, including a human. As would be appreciated by one of skill in this art, the excipients may be chosen, for example, based on the route of administration as described below, the agent being delivered, time course of delivery of the agent, and/or the health/condition of the subject.

Pharmaceutical compositions of the present invention and for use in accordance with the present invention may include a pharmaceutically acceptable excipient or carrier. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and/or to animals parenterally such as intravenously, intranasally (via a nasal spray), and intraperitoneally. The mode of administration will vary depending on the intended use, as is well known in the art. Alternatively, formulations of the present invention may be administered parenterally as injections (intravenous, intramuscular, or subcutaneous). These formulations may be prepared by conventional means, and, if desired, the subject compositions may be mixed with any conventional additive.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

The imaging agents of the invention may be provided in any suitable form, for example, in a pharmaceutically acceptable form. In some cases, the imaging agent is included in a pharmaceutically acceptable composition. In some embodiments, the imaging agent is provided as a composition comprising ethanol, sodium ascorbate, and water. In some cases, the composition comprises less than 20 weight % ethanol, less than 15 weight % ethanol, less than 10 weight % ethanol, less than 8 weight % ethanol, less than 6 weight % ethanol, less than 5 weight % ethanol, less than 4 weight % ethanol, less than 3 weight % ethanol, or less ethanol. In some cases, the composition comprises less than 100 mg/mL, less than 75 mg/mL, less than 60 mg/mL, less than 50 mg/mL, less than 40 mg/mL, less than 30 mg/mL, or less sodium ascorbate in water. In a particular non-limiting embodiment, the imaging agent is provided as a solution in water comprising less than 4% ethanol and less than 50 mg/mL sodium ascorbate in water.

The imaging agent composition for injection may be prepared in an injection syringe. The imaging agent may be prepared by a radiopharmacy (e.g., using the methods described herein) and provided to a health-care professional for administration. In some aspects of the invention, the imaging agent is provided, for example, in a syringe or other container, with ≤50 mg/mL sodium ascorbate in water, ≤4 wt % ethanol, and about 1 to 14 mCi of the imaging agent. In some aspects of the invention, the imaging agent is provided in a container such as a vial, bottle, or syringe, and may be transferred, as necessary, into a suitable container, such as a syringe for administration.

Syringes that include an adsorbent plunger tip may result in 10 to 25% of the imaging agent activity remaining in the syringe after injection. Syringes lacking an adsorbent plunger tip may be used, such as a 3 or 5 mL NORM-JECT (Henke Sass Wolf, Dudley, MA) or other equivalent syringe lacking an adsorbent plunger tip. Reduction of adsorption in the syringe can increase the amount of the imaging agent that is transferred from the syringe and administered to the subject in methods of the invention. A syringe used in methods of the invention may comprise the imaging agent, and be a non-adsorbing, or reduced adsorbent syringe. In some embodiments a non-adsorbent or reduced-adsorbent syringe is a syringe that has been coated or treated to reduce the imaging agent adsorption. In some embodiments, a non-adsorbent or reduced-adsorbent syringe is a syringe that lacks an adsorbent plunger tip. In some embodiments, a syringe used in conjunction with the invention adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of the imaging agent it contains. In certain aspects of the invention, a syringe that contains the imaging agent does not include a rubber or latex tip on the plunger. In some cases a syringe used in methods of the invention, includes a plunger that adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of the imaging agent that the syringe contains. A syringe of the invention may also comprise sodium ascorbate, ethanol, and water, and certain embodiments of the invention include a syringe containing the imaging agent in a solution comprising less than 4% ethanol and less than 50 mg/mL sodium ascorbate in water. A syringe of the invention may be a syringe that is latex free, rubber free, and/or lubricant free. A syringe of the invention may contain the imaging agent in an amount between about 1.5 and about 14 mCi. A syringe of the invention may contain about 20 mCi or less of the imaging agent.

Components of a composition comprising the imaging agent may be selected depending on the mode of administration to the subject. Various modes of administration that effectively deliver imaging agents of the invention to a desired tissue, cell, organ, or bodily fluid will be known to one of ordinary skill in the art. In some embodiments, the imaging agent is administered intravenously (e.g., intravenous bolus injection) using methods known to those of ordinary skill in the art. As used herein, a dose that is "administered to a subject" means an amount of the imaging agent, e.g. the imaging agent that enters the body of the subject. In some embodiments, due to factors such as partial retention of imaging agent such as the imaging agent in a syringe, tubing, needles, catheter, or other equipment used to administer the imaging agent to a subject, the amount of an imaging agent such as the imaging agent that is measured or determined to be in the a syringe or other equipment prepared for administration may be more than the amount in the dose that is administered to the subject. In some embodiments, an injection of an imaging agent is followed by a flushing injection of normal saline, into the subject, using the same tubing, needle, port, etc., used for administration of the imaging agent. Flushing may be performed immediately following administration of the imaging agent, or up to 1 min, 2 min, 3 min, 5 min, or more, after the administration. The volume of saline or other agent for flushing may be up to 5 ml, 6 ml, 7 ml, 8 ml, 9 ml, 10 ml, 15 ml, 20 ml, or more. As will be understood by those of ordinary skill in the art, in embodiments where the imaging agent is administered using a syringe or other container, the true amount of the imaging agent administered to the subject may be corrected for any the imaging agent that remains in the container. For example, the amount of radioactivity remaining in the container, and tubing and needle or delivery instrument that carried the imaging agent from the container and into the subject can be determined after the imaging agent has been administered to the subject and the difference between the starting amount of radioactivity and the amount remaining after administration indicates the amount that was delivered into the subject. In some cases, the container or injection device (e.g., catheter, syringe) may be rinsed with a solution (e.g., saline solution) following administration of the imaging agent.

In some embodiments of the invention, the total amount of the imaging agent administered to a subject over a given period of time, e.g., in one session, is less than or equal to about 50 mCi, less than or equal to 40 mCi, less than or equal to 30 mCi, less than or equal to 20 mCi, less than or equal to 18 mCi, less than or equal to 16 mCi, less than or equal to 15 mCi, less than or equal to 14 mCi, less than or equal to 13 mCi, less than or equal to 12 mCi, less than or equal to 10 mCi, less than or equal to 8 mCi, less than or equal to 6 mCi, less than or equal to 4 mCi, less than or equal to 2 mCi, less than or equal to 1 mCi, less than or equal to 0.5 mCi. The total amount administered may be determined based on a single dose or multiple doses administered to a subject within a given time period of up to 1 minute, 10 minutes, 30 minutes, 1 hour, 2 hours, 6 hours, 12 hours, 24 hours, 48 hours, or more.

Based on radiation dose studies, the desirable maximum dose administered to a subject may be based on determining the amount of the imaging agent which limits the radiation dose to about 5 rem to the critical organ and/or about 1 rem effective dose (ED) or lower, as will be understood by those of ordinary skill in the art. In a particular embodiment, the desirable maximum dose or total amount of the imaging agent administered is less than or equal to about 25 mCi, or less than or equal to about 14 mCi over a period of time of up to 30 min, 1 hour, 2 hours, 6 hours, 12 hours, 24 hours, 48 hours, or more. In some embodiments, the maximum dose of the imaging agent administered to a subject may be less than 3.5 µg per 50 kg of body weight per day. That is, in some embodiments of the invention, the maximum dose of the imaging agent administered to a subject may be less than about 0.07 µg of the imaging agent per kg of body weight per day.

Abbreviations The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| hynic | boc-hydrazinonicotinyl group or 2-[[[5-[carbonyl]-2-pyridinyl]hydrazono]methyl]-benzenesulfonic acid, |
| NMeArg or MeArg | a-N-methyl arginine |
| NMeAsp | a-N-methyl aspartic acid |
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are not used herein:

Ala=alanine Arg=arginine Asn=asparagine Asp=aspartic acid Cys=cysteine Gln=glutamine Glu=glutamic acid Gly=glycine His=histidine Ile=isoleucine Leu=leucine Lys=lysine Met=methionine Nle=norleucine Orn=ornithine Phe=phenylalanine Phg=phenylglycine Pro=proline Sar=sarcosine Ser=serine Thr=threonine Trp=tryptophan Tyr=tyrosine Val=valine.

EXAMPLES

Example 1

We have established the feasibility of in vivo imaging of MMP activation in pigs (Sahul et al. Circ Cardiovasc Imaging 2011, 4:381-391) and dogs (Liu et al. J Nucl Med 2011, 52(3):453-60) post-MI. The data derived in pigs involved surgical occlusion of two marginal branches of the left circumflex artery and resulted in regional activation of MMPs in the inferolateral wall. (Sahul et al. Circ Cardiovasc Imaging 2011, 4:381-391). This surgical model caused significant activation of MMPs in the surgical wound adjacent to both the atria and ventricles of heart, complicating in vivo imaging. The studies in dogs employed percutaneous balloon occlusion of left anterior descending artery, avoided the surgical intervention, and resulted in improved image quality. In these recently published porcine studies with serial SPECT/CT imaging, we demonstrated focal uptake of the MMP-targeted agent $^{99m}$Tc-RP805 within the infarcted lateral wall, which peaked at ~2 weeks post injury, and remained elevated at 4 weeks post occlusion. Early MMP activity at 1 week post-MI predicted late post MI ventricular remodeling (FIG. 1).

Example 2

Heart failure after MI leads to atrial remodeling and fibrosis, thereby increasing vulnerability to AF. The role of atrial MMP activation has not been well studied. We hypothesized that atrial structural remodeling and fibrillation vulnerability occurring early after MI can be noninvasively assessed using targeted molecular imaging of MMP activation.

Methods: In vivo and ex vivo SPECT/CT images were obtained in control pigs (n=7) and in pigs 10 days (n=6) or 4 weeks (n=6) after surgical induction of MI. MI was induced by surgical ligation of two marginal branches of the left circumflex coronary artery. Animals were injected intravenously with a $^{99m}$Tc-labeled radiotracer ($^{99m}$Tc-RP805) targeted to activated MMPs. Hybrid 64-slice SPECT/CT scans were acquired at 2 hours after injection of a $^{99m}$Tc-RP805. X-ray CT imaging with contrast was performed to define coronary anatomy and cardiac chambers.

After sacrifice, hearts were excised and cast in alginate for ex vivo SPECT/CT imaging.

Myocardial $^{99m}$Tc-RP805 retention in the atria and the ventricles was quantified by gamma well counting after sacrifice. AF vulnerability was assessed in subsets of control pigs (n=5) and in pigs 4 weeks post-MI (n=4) using atrial burst pacing for 10 seconds with cycle lengths ranging from 300 to 180 ms.

Figure 2:
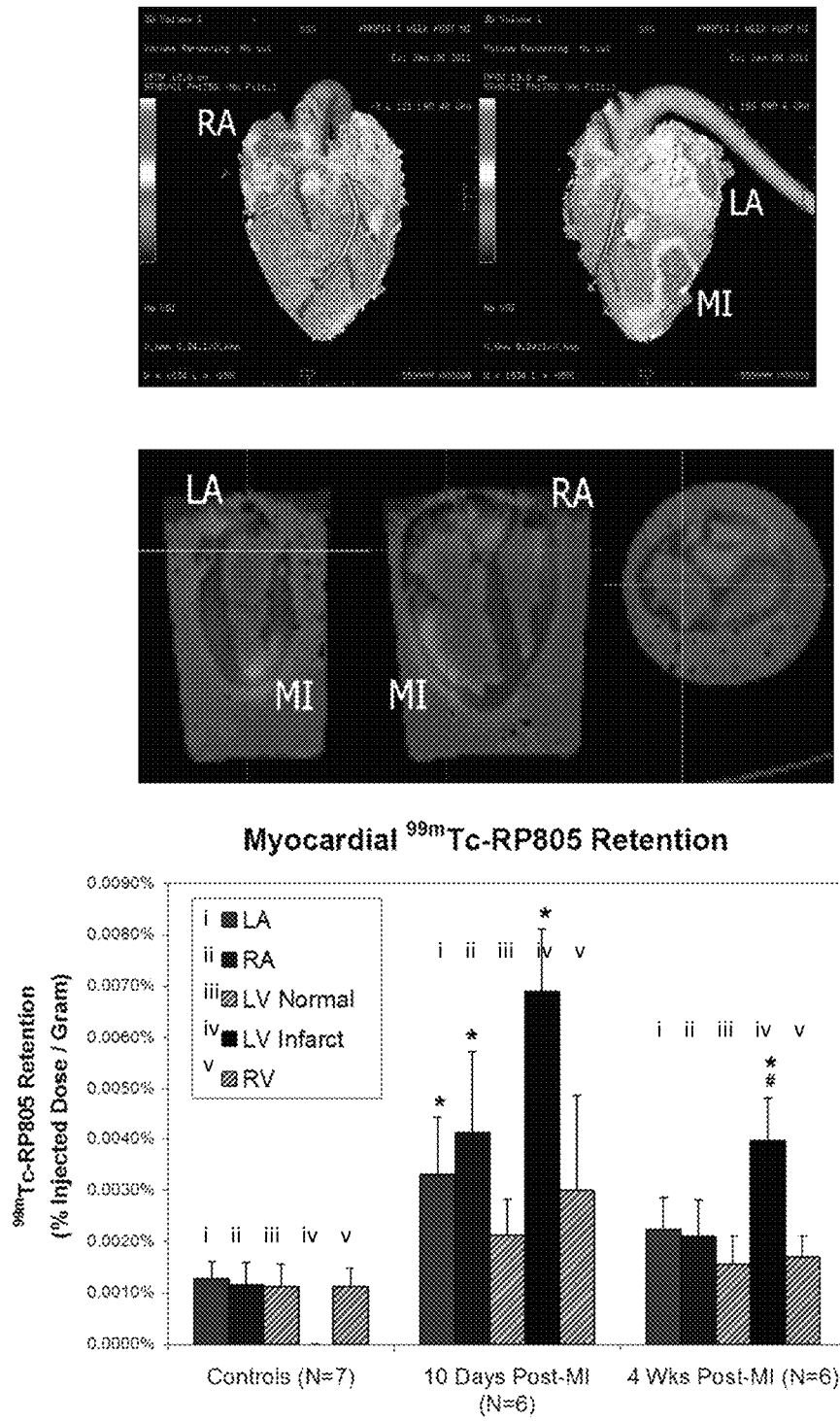
FIG. 2. In vivo (top) and ex vivo (middle) SPECT/CT images were obtained in control pigs (n=7) and in pigs 10 days (n=2). Increased MMP activation is seen in infarct region and in both atria. Graph of myocardial RP805 uptake (% injected dose/g) for control pigs and pigs 10 days and 4 weeks post-MI (bottom). There were significant increases in $^{99m}$Tc-RP805 uptake within both atria and infarct region at 10 days post-MI. At 4 weeks, post-MI infarct region remained significantly elevated (defined as p<0.003 after Bonferonni correction to increase stringency) as did the LA region (p<0.01).

Results: In vivo and ex vivo SPECT/CT imaging demonstrated increased $^{99m}$Tc-RP805 retention in the MI region and both atria compared to control pigs. At 10 days post-MI, a $^{99m}$Tc-RP805 retention (% injected dose/gram) was increased ~6-fold in the MI region and ~3-fold in the left atrium (LA) compared to control regions (p<0.01 each, FIG. 2, bottom panel). At 4 weeks post-MI, $^{99m}$Tc-RP805 retention was increased ~4-fold in the MI region and ~2-fold in the LA compared to control regions (p<0.01 each, FIG. 2, bottom panel). AF was inducible in 4 of 4 pigs at 4 weeks post-MI and 0 of 5 controls (p<0.01). Representative in vivo and ex vivo images at 10 days post-MI are shown in FIG. 2, top and middle panels.

Table 1 shows that AF burden is significantly increased at four weeks post-MI in our post-MI HF model. Following 10 seconds of burst pacing at cycle lengths ranging from 260-180 ms, the duration of AF in post-MI animals was 2.0±1.8 minutes. No AF could be induced in the control group despite pacing down to a cycle length of 180 ms.

TABLE 1

|  | AF duration (sec) | Burst Cycle Length (ms) | p-value |
|---|---|---|---|
| Control (n = 3) | 0.0 | 215 ± 30 |  |
| 4-week HF (n = 4) | 2.0 ± 1.8 | <180 | 0.03 |

Conclusions: MMP-targeted SPECT/CT imaging provides a valuable noninvasive approach for assessment of atrial remodeling and allows early identification of arrhythmogenic substrates prior to the onset of irreversible fibrosis. In vivo imaging of MMP activation has significant clinical implications regarding risk stratification and directing pharmacological and interventional treatments of AF.

Example 3

A cohort of patients post cardioversion are administered an effective amount of the imaging agent of the invention, images of each patient's left atrium are obtained and the uptake of the imaging agent is quantified. A cut point for imaging agent uptake is then established such that the cut point separates the cohort into 2 populations; those above the cut point have recurrent AF while those below the cut point do not.

Based on the cut point levels determined above, future patients are then tested for MMP levels using the methods of the invention and those demonstrating above cut point levels are treated using one or more of the therapies described herein and known in the art for AF, including but not limited to pharmacological rate control therapy, pharmacological rhythm control therapy, ablation, and/or implantable pacer.

Example 4

A cohort of patients with a recent history of myocardial infarction are administered an effective amount of the imaging agent of the invention, images of each patient's left atrium are obtained and the uptake of the imaging agent is quantified. The patients also undergo a resting flurpiridaz F 18 myocardial perfusion study and the summed rest score determined for each patient. Logisitic regression analysis is performed to produce an equation expressing the likelihood of future AF as a function of summed rest score and quantified imaging agent uptake.

Example 5

Part A—Preparation of Imaging Agent 1

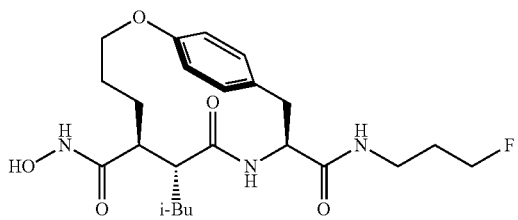

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (J. Med. Chem. 2001, 44, 2636-2660) then transformed into Imaging Agent 1 through the convergent assembly of O-(tetrahydro-2H-pyran-2-yl)hydroxylamine and 3-fluoropropan-1-amine using standard protecting group strategy (Wuts, P. G. M.; Greene, T. W. The Role of Protective Groups in Organic Synthesis. In *Greene's Protective Group in Organic Synthesis, Fourth Edition*; John Wiley & Sons, Inc.: Hoboken, New Jersey, 2007; pp 1-15) and peptide coupling chemical methods (Tsuda, Y; Okada, Y. Solution-Phase Peptide Synthesis. In *Amino Acids, Peptides and Proteins in Organic Chemistry: Building Blocks, Catalysis and Coupling Chemistry, Volume 3*; Hughes, A. B. Ed.; Wiley-VCH Verlag GmbH & Co. KgaA: Weinheim, Germany, 2010; 201-251) commonly known to those skilled in the art.

Part B—Preparation of Imaging Agent 2

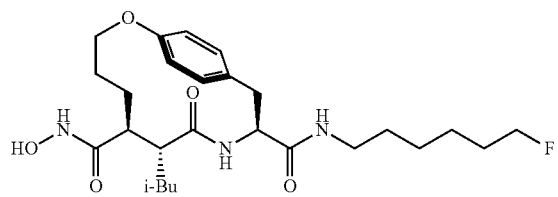

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (J. Med. Chem. 2001, 44, 2636-2660) then transformed into Imaging Agent 2 through the convergent assembly of O-(tetrahydro-2H-pyran-2-yl)hydroxylamine and 6-aminohexan-1-ol using standard protecting group strategy, peptide coupling, and fluorination chemical methods commonly known to those skilled in the art.

Part C—Preparation of Imaging Agent 3

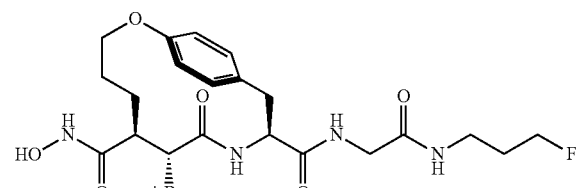

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (J. Med. Chem. 2001, 44, 2636-2660) then transformed into Imaging Agent 3 through the convergent assembly of O-(tetrahydro-2H-pyran-2-yl)hydroxylamine, 2-((tert-butoxycarbonyl)amino)acetic acid and 3-fluoropropan-1-amine using standard protecting group strategy and peptide coupling chemical methods commonly known to those skilled in the art.

Part D—Preparation of Imaging Agent 4

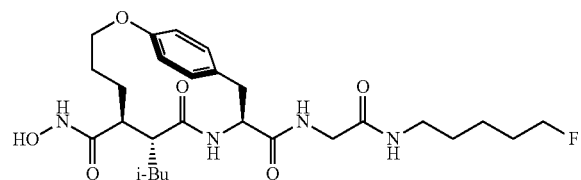

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (*J. Med. Chem.* 2001, 44, 2636-2660) then transformed into Imaging Agent 4 through the convergent assembly of O-(tetrahydro-2H-pyran-2-yl) hydroxylamine, 2-((tert-butoxycarbonyl)amino)acetic acid and 5-aminopentan-1-ol using standard protecting group strategy, peptide coupling, and fluorination chemical methods commonly known to those skilled in the art.

Part E—Preparation of Imaging Agent 5

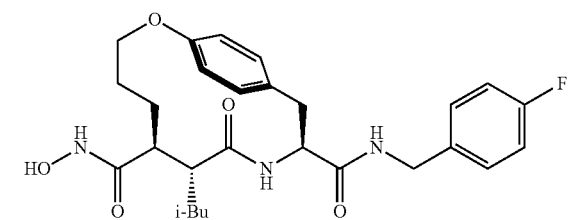

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (*J. Med. Chem.* 2001, 44, 2636-2660) then transformed into Imaging Agent 5 through the convergent assembly of 0-(tetrahydro-2H-pyran-2-yl) hydroxylamine and (4-fluorophenyl)methanamine using standard protecting group strategy and peptide coupling chemical methods commonly known to those skilled in the art.

Part F—Preparation of Imaging Agent 6

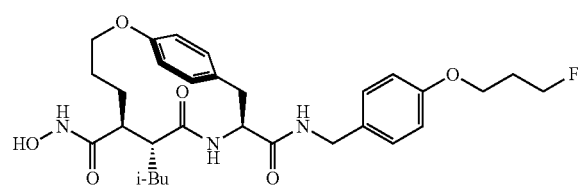

Methyl (3S,7S,6R)-4-aza-7-[(tert-butyl)oxycarbonyl]-6-(2-methylpropyl)-11-oxa-5-oxobicyclo[10.2.2]hexadeca-1(15),12(16),13-triene-3-carboxylate was prepared according to the method of Xue, et al. (*J. Med. Chem.* 2001, 44, 2636-2660) then transformed into Imaging Agent 6 through the convergent assembly of O-(tetrahydro-2H-pyran-2-yl) hydroxylamine, and (4-(3-fluoropropoxy)phenyl)methanamine using standard protecting group strategy and peptide coupling chemical methods commonly known to those skilled in the art. (4-(3-Fluoropropoxy)phenyl)methanamine was prepared from 4-hydroxybenzonitrile and 1-bromo-3-fluoropropane.

Example 6: In-Vitro MMP Inhibition Assay

Individual inhibitors were dissolved in TCN buffer (50 mM Tris-HCl, 10 mM $CaCl_2$, 150 mM NaCl, 0.05% Brij 35 at pH 7.5) at appropriate dilutions then added to the wells of a microtiter plate (10 μL/well) in triplicate. Each well of test agent (and appropriate control wells) was then treated with activated MMP-2 or 9 (10 μL of a 40 nM solution in 50 mM Hepes, 10 mM $CaCl_2$), 1% Brij 35 at pH 7.5; R&D Systems) followed by 30 μL TCN buffer and 150 μL the fluorogenic peptide substrate (Mca-PLGL-Dpa-AR-$NH_2$; R&D Systems). The resulting mixtures were incubated 1 h at 27° C. then analyzed using a FL600 fluorescent plate reader (excitation=310/20; emission=420/50; optics=bottom; sensitivity=225) and KC4 Software.

TABLE 2

| MMP inhibition data | | |
|---|---|---|
| Imaging Agent | MMP-2 | MMP-9 |
| 1 | 5.19 | 3.54 |
| 2 | 31.6 | 20.2 |
| 3 | 4.61 | 2.59 |
| 4 | 15.4 | 15.3 |
| 5 | 0.58 | 0.74 |
| 6 | 2.74 | 2.98 |
| RP805 | 6.50 | 7.40 |

Example 7

Figure 3:
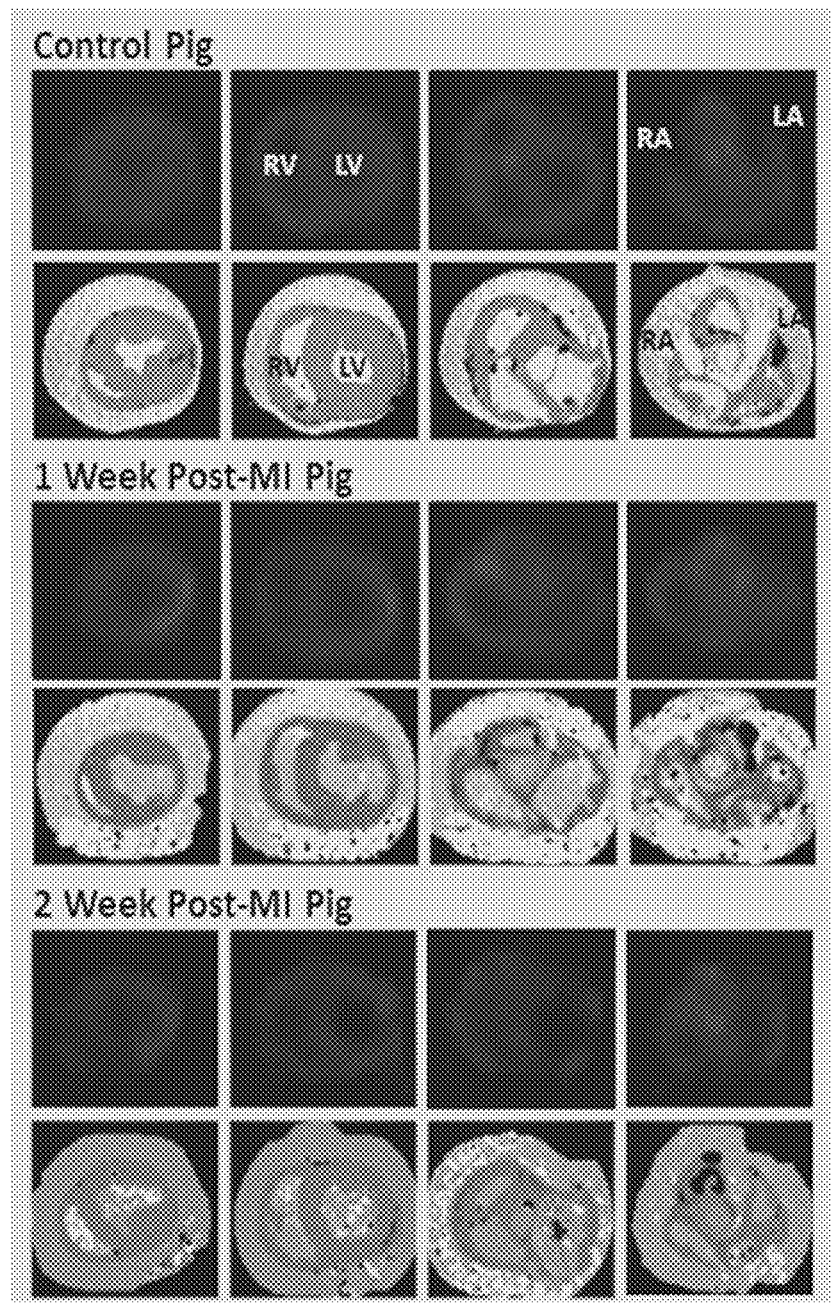
FIG. 3. Representative transaxial slices from ex vivo SPECT images of a control pig heart, and hearts from pigs at 1 and 2 weeks post-MI. The top row of each image contain are targeted $^{99m}$Tc-RP805 images (linear grey scale) matched with corresponding high resolution CT images (gray scale, below). Hearts were filled with alginate mixed with CT contrast to define right and left ventricles (RV & LV) and atria (RA & LA). Uniform uptake is seen in the control heart. Infarcted hearts demonstrate focal $^{99m}$Tc-RP805 in the infarct region and in the atria.

FIG. 3 shows representative transaxial slices from ex vivo SPECT images of a control pig heart, and hearts from pigs at and 2 weeks post-MI. the top row of each image set are targeted $^{99m}$Tc-RP805 images (linear grey scale) matched with corresponding high resolution CT images (gray scale, below). Hearts were filled with alginate mixed with CT contrast to define right and left ventricles (RV & LV) and atria (RA & LA). Uniform uptake is seen in the control heart. Infarcted hearts demonstrate focal $^{99m}$Tc-RP805 in both the infarct region and atria.

Figure 4:
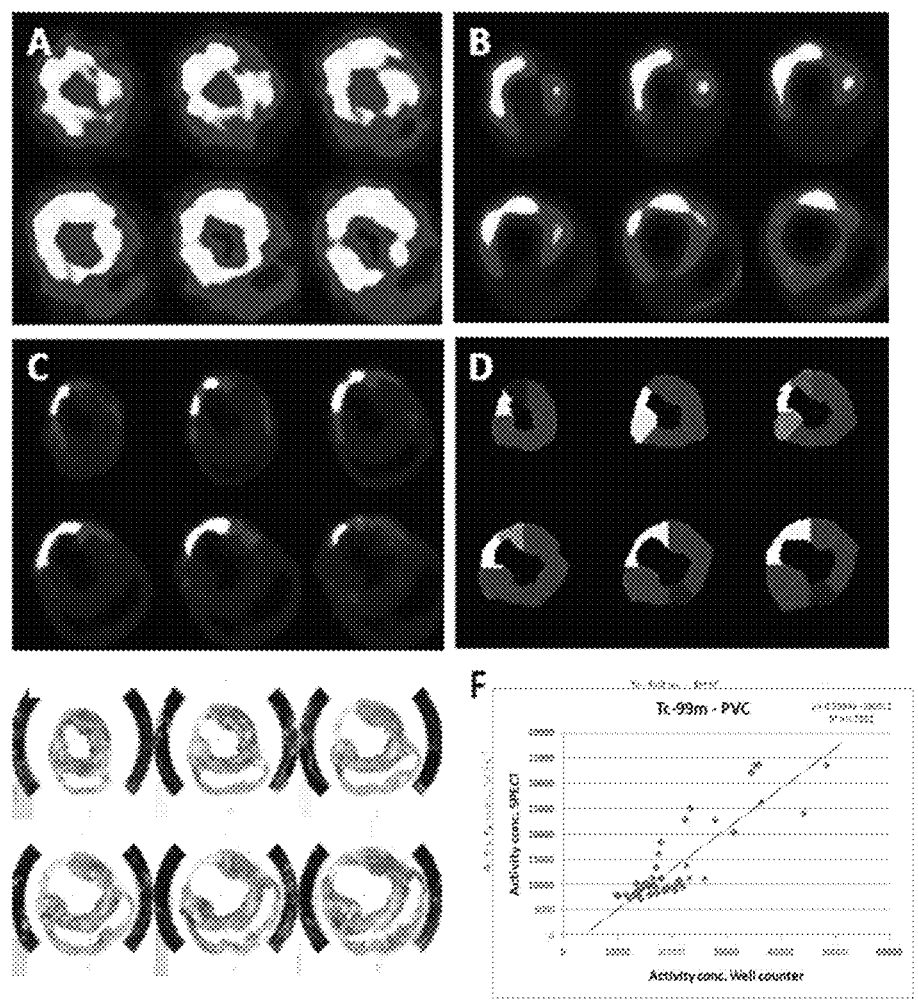
FIG. 4. Results from quantitative analysis of ex vivo $^{99m}$Tc-RP805 SPECT images from a pig heart at 4 weeks post-MI. A. Uncorrected SPECT images, B. SPECT images with resolution recovery, C. SPECT data reconstructed with partial volume correction (PVC), D. Grey-scale $^{99m}$Tc-RP805 activity for 8 radial sectors per slice from gamma well counter, F. Postmortem images of heart demonstrating dense inferolateral scar and marked wall thinning, F. Correlation between measured regional myocardial well-counter activity and SPECT derived activity with PVC.

FIG. 4 shows results from quantitative analysis of ex vivo $^{99m}$Tc-RP805 SPECT images from a pig heart at 4 weeks post-MI. A. Uncorrected SPECT images, B. SPECT images with resolution recovery, C. SPECT data reconstructed with partial volume correction (PVC), D. Grey scale-coded $^{99m}$Tc-RP805 activity for 8 radial sectors per slice from gamma well counter, E. Postmortem images of heart demonstrating dense inferolateral scar and marked wall thinning, F. Correlation between measured regional myocardial well-counter activity and SPECT derived activity with PVC.

Figure 5:
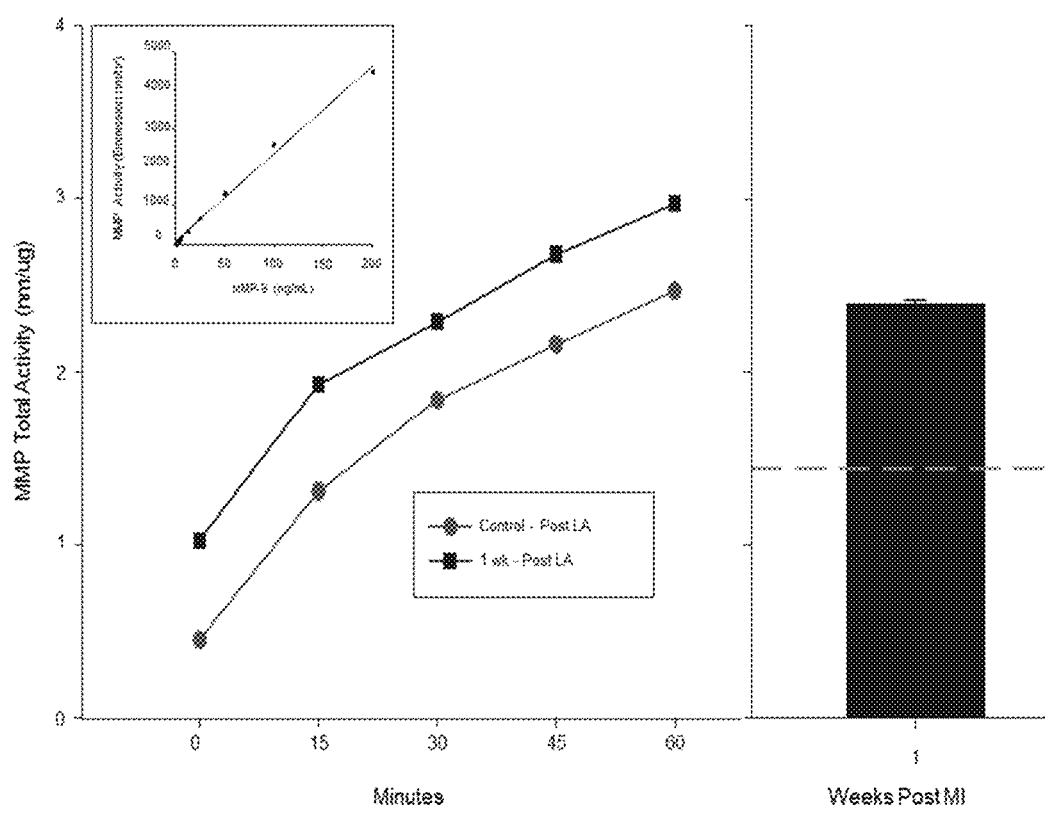
FIG. 5. Plot of the MMP total activity per unit time, according to some embodiments.

FIG. 5 shows a plot of the MMP total activity per unit time, according to some embodiments.

Figure 6:
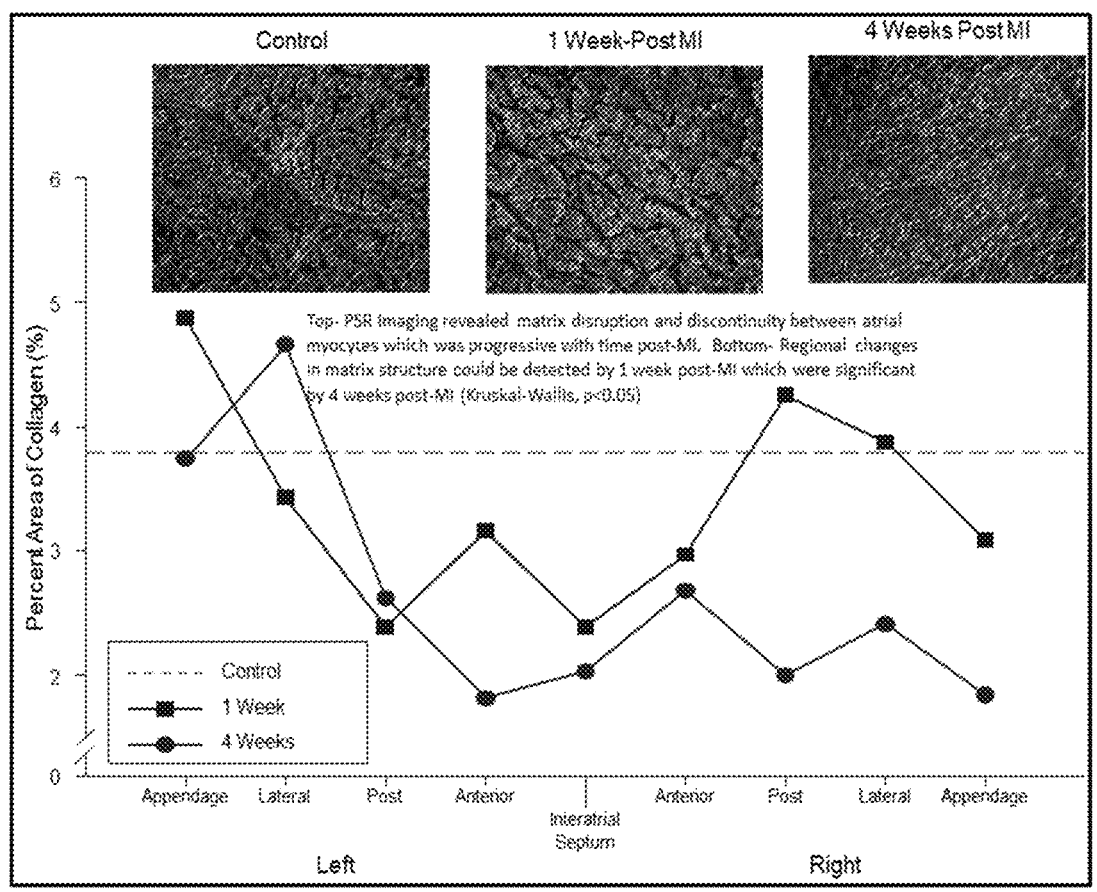
FIG. 6. Plot of the percent area collagen for the left and right regions of the heart. Regional changes in matrix structure could be detected by 1 week post-MI which were significant by 4 weeks post-MI (Kruskal-Wallis, p<0.05). In the inset: PSR Imaging revealed matrix disruption and discontinuity between atrial myocytes which was progressive with time post-MI.

FIG. 6 shows a plot of the percent area collagen for the left and right regions of the heart. Regional changes in matrix structure could be detected by 1 week post-MI which were significant by 4 weeks post-MI (Kruskal-Wallis, p<0.05). In the inset: PSR imaging revealed matrix disruption and discontinuity between atrial myocytes which was progressive with time post-MI.

Example 8

Calcific aortic valve disease (CAVD) is common among the elderly population. Inflammation and matrix remodeling play a central role in the progression of CAVD to symptomatic aortic stenosis. Matrix metalloproteinases (MMPs) are upregulated in CAVD. In vivo imaging of MMP activation may lead to prospective identification of aortic valves that are at high risk for developing stenosis and help track the effect of potential novel therapeutic interventions. This example illustrates use of an MMP-targeted agent for both in vivo imaging and definition of temporal patterns of MMP activation in CAVD.

Methods and results: ApoE$^{-/-}$ mice were fed a high fat diet (HFD) for up to 9 months. Histological analysis of the aortic valve showed considerable thickening of valve leaflets over time. M mode echocardiography demonstrated a reduction in leaflet separation from 3 months to 9 months. Non-contrast high resolution CT established the presence of aortic valve calcification after 9 months of HFD. MMP-targeted microSPECT imaging using $^{99m}$Tc-RP805, a tracer with specificity for activated MMPs, followed by CT angiography showed considerable tracer uptake (in counts per voxel per MBq injected dose) in the aortic valve area at 3, 6 and 9 months. Uptake was maximal after 6 months of HFD (3 m: 0.047±0.002, n=2, 6 m: 0.102±0.013, n=4, 9 m: 0.064±0.004, n=4). Tracer uptake in the aortic valve area was confirmed following ex vivo planar imaging.

Conclusion: MMP-targeted microSPECT/CT imaging can detect aortic valve biology in CAVD in vivo. In this model, protease activation in the aortic valve is maximal at 6 months and declines with progression of CAVD.

Figure 7:
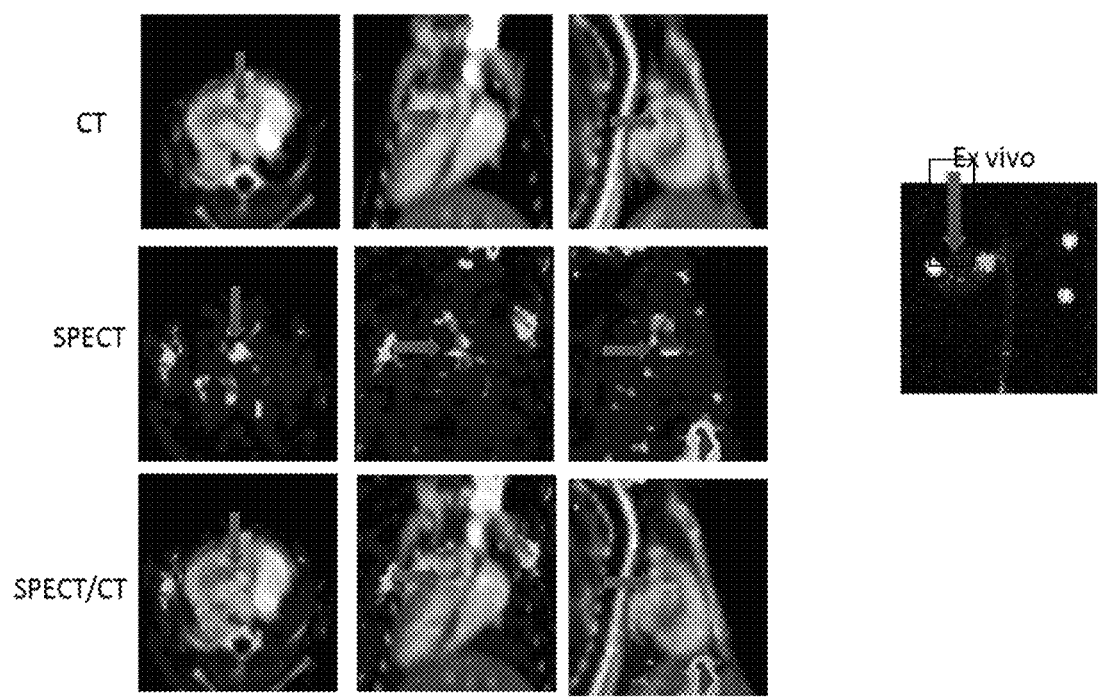
FIG. 7. $^{99m}$Tc-RP805 in vivo microSPECT/CT imaging (left) of MMP activation in an ApoE−/− mouse fed a Western diet for 9 months. Tracer uptake in the aortic valve area is indicated by the arrows. Uptake in the aortic valve was confirmed by ex vivo planar imaging (right) of the explanted heart and aorta.

FIG. 7 shows $^{99m}$Tc-RP805 in vivo microSPECT/CT imaging (left) of MMP activation in an ApoE−/− mouse fed a Western diet for 9 months. Tracer uptake in the aortic valve area is indicated by the arrows. Uptake in the aortic valve was confirmed by ex vivo planar imaging (right) of the explanted heart and aorta.

Figure 8:
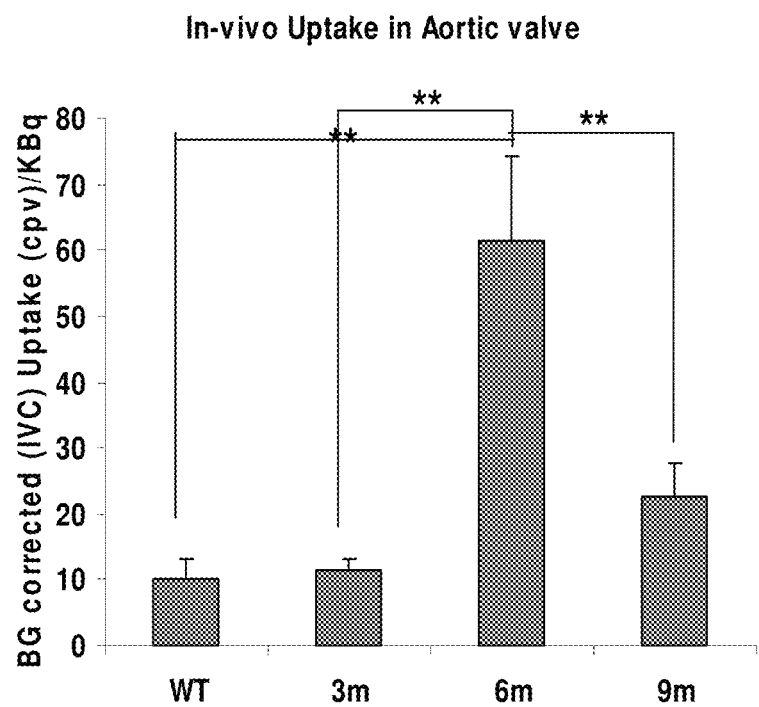
FIG. 8. Plot of in vivo uptake over time of 99mTc-RP805 in the aortic valve over time in ApoE−/− mice fed a Western diet at various timepoints, and related data.

FIG. 8 shows in vivo uptake of $^{99m}$Tc-RP805 in the aortic valve over time in ApoE$^{-/-}$ mice fed a Western diet.

Figure 9:
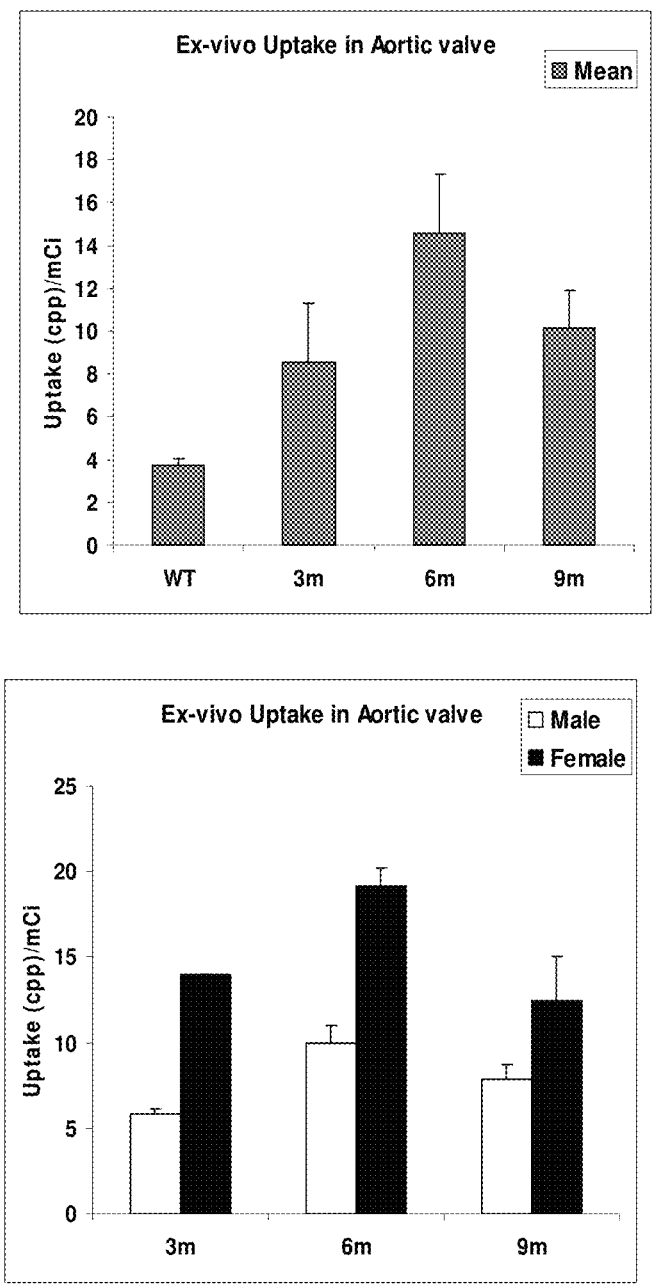
FIG. 9. Plot of ex vivo uptake of $^{99m}$Tc-RP805 in the aortic valve over time in ApoE−/− mice fed a Western diet.

FIG. 9 shows ex vivo uptake of $^{99m}$Tc-RP805 in the aortic valve over time in ApoE$^{-/-}$ mice fed a Western diet.

Figure 10:
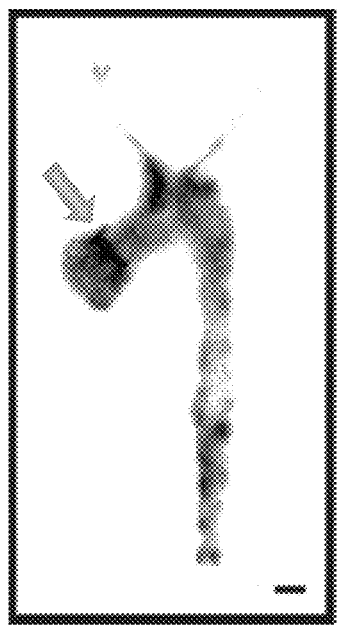
FIG. 10. Autoradiography of the explanted aorta from an ApoE−/− mouse fed a Western diet for three months. Arrows indicate uptake of $^{111}$In-RP782 in the aortic valve area.

FIG. 10 shows autoradiography of the explanted aorta from an ApoE−/− mouse fed a Western diet for three months. Arrows indicate uptake of $^{111}$In-RP782 in the aortic valve area.

Figure 11:
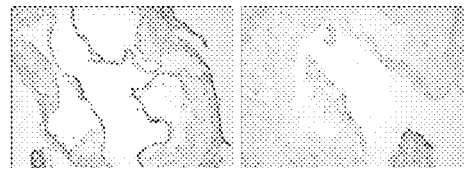
FIG. 11. H&E staining of the aortic valve in ApoE−/− mice fed a Western diet for 4 (left) and 9 months (right) demonstrating marked remodeling of valve leaflets over time.

FIG. 11 shows H&E staining of the aortic valve in ApoE−/− mice fed a Western diet for 4 (left) and 9 months (right) demonstrating marked remodeling of valve leaflets over time.

Figure 12:
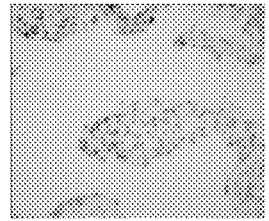
FIG. 12. Immunostaining of F4-80 (dark grey) in the aortic valve from an ApoE−/− mouse fed a Western diet for 6 months demonstrating considerable macrophage infiltration.

FIG. 12 shows immunostaining of F4-80 (dark grey) in the aortic valve from an ApoE−/− mouse fed a Western diet for 6 months demonstrating considerable macrophage infiltration.

Figure 13:
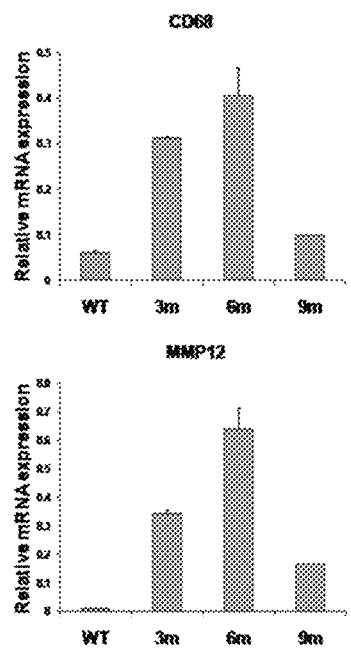
FIG. 13. Plots of aortic valve GAPDH-normalized CD68 (top) and MMP-12 (bottom) mRNA expression quantified by real time RT-PCR in wild type (WT) mice on normal chow and ApoE−/− mice fed a Western diet for 3, 6 or 9 months.

FIG. 13 shows plots of aortic valve GAPDH-normalized CD68 (top) and MMP-12 (bottom) mRNA expression quantified by real time RT-PCR in wild type (WT) mice on normal chow and ApoE−/− mice fed a Western diet for 3, 6 or 9 months.

Figure 14:
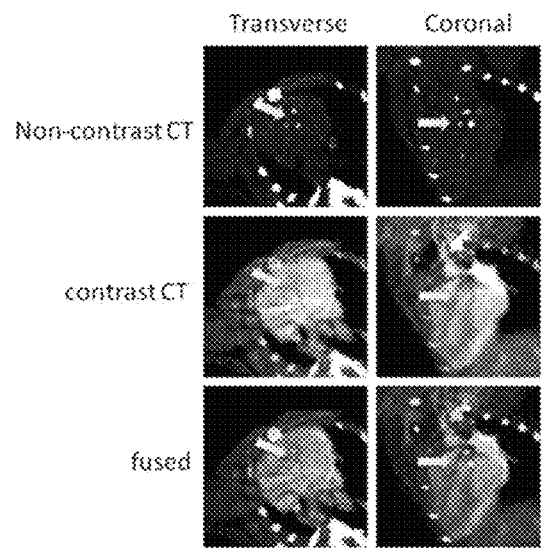
FIG. 14. Grey scale-coded non contrast CT images of an ApoE−/− mouse fed a Western diet for 10 months demonstrating calcification of the aortic valve. Arrows indicate the aortic valve plane.

FIG. 14 shows grey scale-coded non contrast CT images of an ApoE−/− mouse fed a Western diet for 10 months demonstrating calcification of the aortic valve. Arrows indicate the aortic valve plane.

Figure 15:
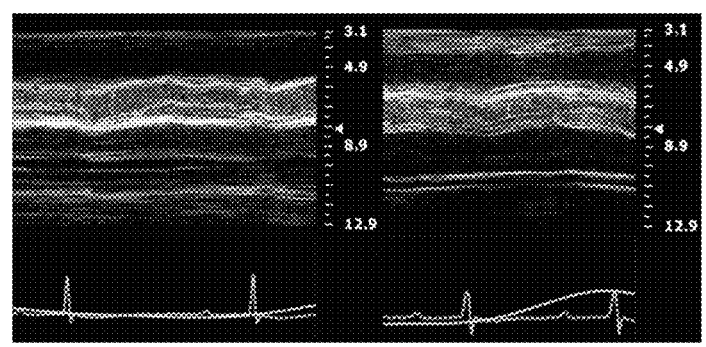
FIG. 15. M mode echocardiographic images of ApoE−/− mice fed a Western diet demonstrating normal systolic separation of aortic valve cusps after 3 months on diet (left) and reduced separation after 9 months (right).

FIG. 15 shows M mode echocardiographic images of ApoE−/− mice fed a Western diet demonstrating normal systolic separation of aortic valve cusps after 3 months on diet (left) and reduced separation after 9 months (right).

Example 9

Atherosclerosis, a major cause of morbidity and mortality in the US, is linked to hyperlipidemia. Pharmacologic treatment of hyperlipidemia is a mainstay of modern treatment for atherosclerotic diseases and is believed to be related at least in part to "stabilizing" effects on plaque biology. This example investigates the effect of anti-lipid therapies on plaque biology through serial imaging of matrix metalloproteinase (MMP) activation in vivo.

Methods: ApoE$^{-/-}$ mice were fed a high fat diet (HFD) for 2 months to induce atherosclerosis. After two months, the mice were randomly assigned to one of 4 groups: HFD, HFD plus simvastatin (Sim), HFD plus fenofibrate (Fen) and high fat withdrawal (HFW). MicroSPECT/CT imaging using $^{99m}$Tc-RP805, a tracer with specificity for activated MMPs was performed after one week and 4 weeks.

Results: Withdrawal of the HFD significantly reduced total cholesterol levels at 1 week (1845.1±41.9 to 492.7±19.4 mg/dL, p=0.001). Neither simvastatin nor fenofibrate had a significant effect on total cholesterol level compared to animals on HFD at one week, but both significantly reduced cholesterol levels by 4 weeks. At 1 week, there was no significant difference in uptake of $^{99m}$Tc-RP805 in the aortic arch between different experimental groups. Uptake (in counts per voxel per mCi injected dose) at 4 weeks however, was significantly higher in the HFD group compared to other three groups (HFD: 4.99±0.27, n=5, Sim: 3.17±0.52, n=6, p<0.02, Fen: 2.23±0.28, n=7, p<0.001, HFW: 1.77±0.22, n=5, p<0.001). $^{99m}$Tc-RP805 uptake in the aortic arch significantly increased from 1 week to 4 weeks in animals on HFD (mean uptake 2.84±0.47 versus 4.99±0.27, p<0.003), but did not occur in the other experimental groups.

Conclusions: MMP-targeted molecular imaging demonstrates an effect of anti-lipid therapies on plaque biology at 4 weeks, but not at 1 week after initiation of therapy.

Example 10: Tissue Biodistribution

Oncomice®, obtained through an in-house breeding program, were anesthetized intramuscularly with 0.1 mL of ketamine/acepromazine (1.8 mL saline, 1.0 mL ketamine, and 0.2 mL acepromazine) prior to dosing and tissue sampling. Individual mice were then injected via the tail vein with an imaging agent of the present invention (0.5-2.0 mCi/kg in 0.1 mL). Mice were euthanized and biodistribution performed at 1 h post-injection. Selected tissues were removed, weighed, and counted on a gamma counter. Results are expressed as the percentage of injected dose per gram tissue (mean±SEM; Table 3).

TABLE 3

Summary of imaging agent distribution in the Oncomouse ®

| | Imaging Agent Distribution (% ID/g) | | |
|---|---|---|---|
| tissue | 2 | 4 | 6 |
| blood | 1.07 ± 0.060 | 0.41 ± 0.099 | 0.88 ± 0.061 |
| heart | 0.95 ± 0.065 | 0.36 ± 0.064 | 0.69 ± 0.073 |
| lung | 0.97 ± 0.121 | 0.45 ± 0.071 | 1.69 ± 0.382 |
| liver | 13.1 ± 2.17 | 23.6 ± 5.19 | 11.3 ± 1.73 |
| spleen | 0.69 ± 0.085 | 0.34 ± 0.057 | 0.81 ± 0.021 |
| kidney | 20.6 ± 3.25 | 14.8 ± 1.79 | 6.66 ± 1.46 |
| bone | 2.02 ± 0.320 | 1.28 ± 0.200 | 2.86 ± 0.124 |
| muscle | 0.50 ± 0.073 | 0.17 ± 0.043 | 0.44 ± 0.049 |
| urine | 71.8 | 7.67 ± 5.00 | 7.21 ± 6.71 |
| tumor | 0.95 ± 0.103 | 1.12 ± 0.204 | 0.73 ± 0.026 |

EQUIVALENTS

Unless defined otherwise, all technical and scientific terms used herein have the same meanings as commonly understood by one of skill in the art to which the disclosed methods and compositions belong.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It must be noted that as used herein and in the appended claims, the singular forms "a," "an," and "the" include plural reference unless the context clearly dictates otherwise. Thus, for example, reference to "an MMP" includes a plurality of such MMPs, reference to "the MMP" is a reference to one or more MMP and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Throughout the description and claims of this specification, the word "comprise" and variations of the word, such as "comprising" and "comprises," means "including but not limited to" and is not intended to exclude, for example, other additives, components, integers or steps.

What is claimed is:

1. A method of evaluating risk of developing atrial fibrillation as a primary event comprising:

administering, to a subject, imaging agent $^{99m}$Tc-RP805:

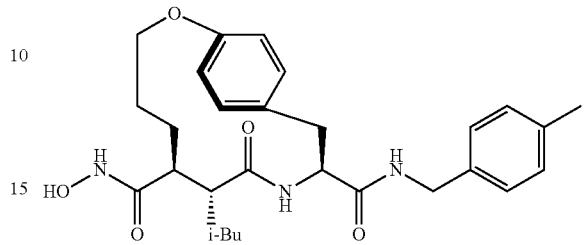

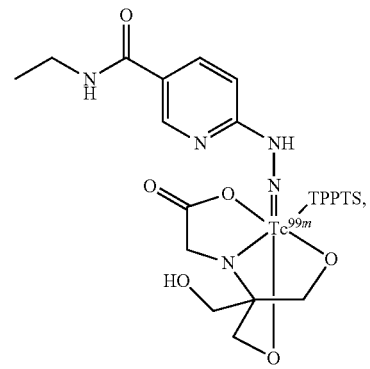

wherein TPPTS is 3,3',3"-phosphanetriyltris(benzenesulfonic acid) trisodium salt, and acquiring an image of the atria or the aortic valve region of the subject, wherein the image indicates an aggregate level of MMP comprising MMP-2, MMP-9 and MMP-14 in the atria or the aortic valve region of the subject, and wherein an aggregate level of MMP in the atria or the aortic valve region of the subject above control is indicative of an increased risk of developing atrial fibrillation.

2. A method for evaluating risk of developing atrial fibrillation recurrence comprising:

administering to a subject previously diagnosed with atrial fibrillation and previously treated for atrial fibrillation, imaging agent $^{99m}$Tc-RP805:

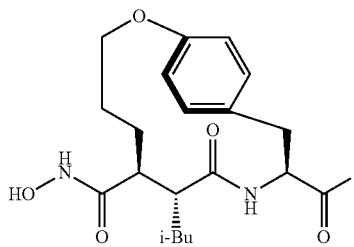

wherein TPPTS is 3,3',3"-Phosphanetriyltris(benzene-sulfonic acid) trisodium salt, and acquiring an image of the atria or the aortic valve region of the subject, wherein the image indicates an aggregate level of MMP comprising MMP-2, MMP-9 and MMP-14 in the atria or the aortic valve region of the subject, and wherein an aggregate level of MMP in the atria or the aortic valve region of the subject above control is indicative of an increased risk of atrial fibrillation recurrence.

3. The method of claim 2, wherein the atrial fibrillation recurrence is atrial fibrillation recurrence following cardioversion therapy.

4. A method for identifying a subject having a history of atrial fibrillation that is likely to respond to treatment with an implantable pacer, pharmacological rate control therapy, pharmacological rhythm control therapy, or ablation therapy, comprising:

administering, to a subject previously diagnosed with atrial fibrillation, imaging agent $^{99m}$Tc-RP805:

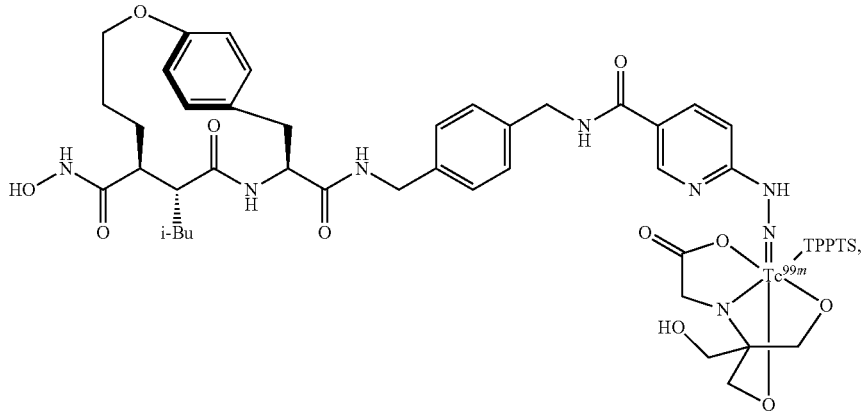

wherein TPPTS is 3,3',3"-Phosphanetriyltris(benzene-sulfonic acid) trisodium salt; and acquiring an image of the atria or the aortic valve region of the subject, wherein the image indicates an aggregate level of MMP comprising MMP-2, MMP-9 and MMP-14 in the atria or the aortic valve region of the subject, and wherein an aggregate level of MMP in the atria or the aortic valve region of the subject above control identifies a subject that is likely to respond to treatment with an implantable pacer, pharmacological rate control therapy, pharmacological rhythm control therapy, or ablation therapy.

5. The method of claim 4, wherein the subject has experienced one atrial fibrillation event.

6. The method of claim 4, wherein the subject has experienced recurrent atrial fibrillation.

7. The method of claim 1, wherein the image of the atria is a left atrial image.

8. The method of claim 1, wherein the subject is a human subject.

9. The method of claim 1, wherein the subject has experienced a myocardial infarction.

10. The method of claim 1, further comprising determining a measure of myocardial perfusion in the subject, wherein determining a measure of myocardial perfusion in the subject comprises administering to the subject a myocardial perfusion imaging agent and obtaining an image of myocardial perfusion.

11. The method of claim 4, wherein the image of the atria is a left atrial image.

12. The method of claim 4, wherein the subject is a human subject.

13. The method of claim 4, wherein the subject does not exhibit the condition of myocardial fibrosis.

14. The method of claim 4, wherein the subject does not exhibit the condition of myocardial remodeling.

15. The method of claim 4, wherein the subject has experienced a myocardial infarction.

16. The method of claim 4, further comprising determining a measure of myocardial perfusion in the subject, wherein determining a measure of myocardial perfusion in the subject comprises administering to the subject a myocardial perfusion imaging agent and obtaining an image of myocardial perfusion.

* * * * *

UNITED STATES PATENT AND TRADEMARK OFFICE
CERTIFICATE OF CORRECTION

PATENT NO. : 11,865,195 B2  
APPLICATION NO. : 16/881182  
DATED : January 9, 2024  
INVENTOR(S) : Albert J. Sinusas et al.

Page 1 of 1

It is certified that error appears in the above-identified patent and that said Letters Patent is hereby corrected as shown below:

On the Title Page

Item (73) Assignees:
"Lantheus Medical Imaging, Inc., North Billerica, MA (US)"

Should read:
-- Lantheus Medical Imaging, Inc., North Billerica, MA (US); Yale University, New Haven, CT (US) --

Signed and Sealed this  
Third Day of June, 2025

Coke Morgan Stewart  
*Acting Director of the United States Patent and Trademark Office*